US012753179B2

(12) United States Patent
Lu et al.

(10) Patent No.: US 12,753,179 B2
(45) Date of Patent: Oct. 6, 2026

(54) FGFR INHIBITOR COMPOUND AND USE THEREOF

(71) Applicant: Medinno Pharmceutical (Xiamen) Co., Ltd., Xiamen City (CN)

(72) Inventors: Liang Lu, Shanghai (CN); Saisai Zhao, Jiyuan (CN); Hai Huang, Zhengzhou (CN); Longzheng Zhang, Xinmi (CN); Jixuan Zhang, Dengfeng (CN); Jiaxin Chen, Shenzhen (CN); Shancun Ling, Shenzhen (CN)

(73) Assignee: SHENZHEN KANGSU PHARMACEUTICAL TECHNOLOGY CO., LTD. (CN)

( * ) Notice: Subject to any disclaimer, the term of this patent is extended or adjusted under 35 U.S.C. 154(b) by 426 days.

(21) Appl. No.: 18/351,756

(22) Filed: Jul. 13, 2023

(65) Prior Publication Data

US 2023/0374025 A1 Nov. 23, 2023

Related U.S. Application Data

(63) Continuation of application No. PCT/CN2022/072149, filed on Jan. 14, 2022.

(51) Int. Cl.
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
CPC ..... C07D 471/04; C07D 487/04; A61P 35/00; A61P 35/02; A61P 1/16; A61P 11/00; A61P 13/12; A61P 17/02; A61P 19/02; A61P 19/08; A61P 3/12
See application file for complete search history.

(56) References Cited

U.S. PATENT DOCUMENTS

2014/0171405 A1 6/2014 Zhuo et al.

FOREIGN PATENT DOCUMENTS

| | | |
|---|---|---|
| CN | 106317023 A | 1/2017 |
| CN | 111606908 A | 9/2020 |
| CN | 113666911 A | 11/2021 |

OTHER PUBLICATIONS

Abraham, Burger's Medicinal Chemistry & Drug Discovery, Sixth Edition, vol. 2: Drug Discovery and Drug Development, Chapter 14, 499-532, 2003 (Year: 2003).*
Haberson et al., Deuterium Medicinal Chemistry: A New Approach to Drug Discovery and Development, Medchem News, No. 2, May 2014 (Year: 2014).*
International Search Report and Written Opinion of the International Searching Authority for International Application No. PCT/CN2022/072149, mailed Apr. 15, 2022.
Stahl, P.H. et al., "Handbook of Pharmaceutical Salts: Properties, Selection and Use," Chemistry International, 24(3), 2002.
The first Office Action issued by the China National Intellectual Property Administration (CNIPA) dated Dec. 28, 2022 for the Chinese Patent Application No. 202210044992.2.
The Notification to Grant Patent Right for Invention issued by the China National Intellectual Property Administration (CNIPA) dated May 31, 2023 for the Chinese Patent Application No. 202210044992.2.

* cited by examiner

*Primary Examiner* — Sarah Pihonak
*Assistant Examiner* — Padmaja S Rao
(74) *Attorney, Agent, or Firm* — MASCHOFF BRENNAN

(57) ABSTRACT

The present disclosure relates to FGFR inhibitor compounds and its use. Specifically, the present disclosure discloses a compound represented by formula (I), isotopically labeled compound thereof, or optical isomer thereof, geometric isomer thereof, a tautomer thereof or a mixture of various isomers, or a pharmaceutically acceptable salt thereof, or a prodrug thereof, or a metabolite thereof. The present disclosure also relates to use of the above compound in medicine.

(I)

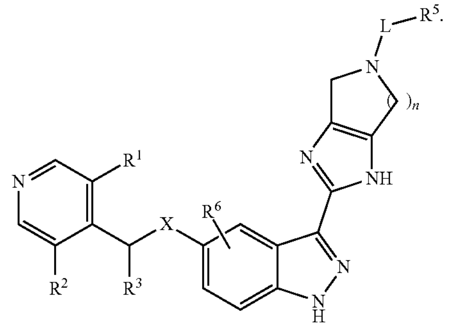

18 Claims, No Drawings

FGFR INHIBITOR COMPOUND AND USE THEREOF

CROSS-REFERENCE TO RELATED APPLICATION

The present application is a continuation of International Application No. PCT/CN2022/072149 filed on Jan. 14, 2022 which claims priority to Chinese Patent Application No. 202110056415.0 filed on Jan. 15, 2021, both of which are incorporated herein by reference in their entireties.

TECHNICAL FIELD

The present disclosure provides a class of novel compounds with pharmacological activity, which can be used to inhibit fibroblast growth factor receptor, FGFR. The present disclosure also relates to a composition comprising the compound, and use of the compound and the composition in the preparation of a medicament for the treatment of FGFR-related diseases or disorders.

BACKGROUND

The fibroblast growth factor receptor (FGFR) family is a class of transmembrane receptor tyrosine kinases (RTK) and includes four members: FGFR1, FGFR2, FGFR3 and FGFR4. FGFRs can be activated by the binding of natural ligands. Activated FGFRs can then activate a variety of downstream signaling pathways including Ras-MAPK, AKT-PI3K and phospholipase C, which are involved in a variety of important physiological processes, such as proliferation, differentiation, cell migration and survival, among others.

Aberrant constitutive activation of FGFRs is found in a variety of tumors. Several inhibitors of FGFRs have been developed for the treatment of various cancers. Preclinical and early clinical trials have demonstrated that multiple FGFR inhibitors are effective in reducing tumor size.

However, one of the major obstacles to the use of FGFR inhibitors in clinical cancer therapy is the acquired resistance against them. This resistance can be acquired through mutations or activation of back-complementary signaling pathways in FGFRs, wherein the mutations on residues known as gatekeepers (referred to as "gatekeeper mutations") is one of the most common pathways of resistance acquisition.

Drug resistance due to gatekeeper mutations in FGFRs has been reported in both preclinical and clinical trials. For example, the V561M mutation in FGFR1 leads to strong resistance to FIIN-1; the V564F mutation in FGFR2 leads to strong resistance to BGJ398; and the V555M mutation in FGFR3 leads to resistance to AZ8010, PD173074 and AZD4547.

It is desirable to develop FGFR inhibitors that still have inhibitory activity against FGFRs carrying gatekeeper mutations to address the acquired resistance caused by gatekeeper mutations. Recent studies have reported several inhibitors that are effective against FGFR gatekeeper mutations, such as FIIN2.

There remains a need for more effective FGFR inhibitors, for example, FGFR inhibitors having higher inhibition rates, targeting a wider variety of FGFRs and FGFR mutations, or having higher selectivity for certain FGFRs and FGFR mutations, among others.

SUMMARY

In a first aspect, the present disclosure provides a compound of Formula (I) as a FGFR inhibitor, that is capable of inhibiting both wild and mutant FGFRs (I)

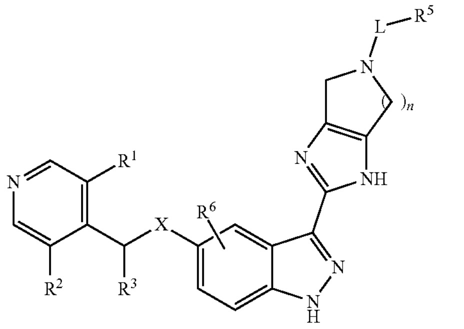

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, wherein $R^1$ and $R^2$ are each independently selected from H, halogen, —CN, OH, —$NO_2$, —$N(R^7)(R^8)$, $C_{1-4}$ alkyl, $C_{1-4}$ haloalkyl, $C_{1-4}$ alkoxy, $C_{3-6}$ alicyclic group, and 4-6 membered heteroalicyclic group; and $R^3$ is selected from H, $C_{1-4}$ alkyl, $C_{1-4}$ haloalkyl, $C_{1-4}$ alkoxy, $C_{3-6}$ alicyclic group, and 4-6 membered heteroalicyclic group; and 1, 2 or 3 $R^6$(s) are present in formula (I), and each $R^6$ is independently selected from H, halogen, —CN, —OH, —$NO_2$, —$N(R^7)(R^8)$, $C_{1-4}$ alkyl, $C_{1-4}$ haloalkyl, $C_{1-4}$ alkoxy, $C_{3-6}$ alicyclic group, and 4-6 membered heteroalicyclic group; and X is O, S or ($NR^4$) in which $R^4$ is selected from H, $C_{1-4}$ alkyl, $C_{1-4}$ haloalkyl, $C_{1-4}$ alkoxy, $C_{3-6}$ alicyclic group, and 4-6 membered heteroalicyclic group; and $R^7$ and $R^8$, at each occurrence, are each independently selected from H, $C_{1-6}$ alkyl, $C_{1-4}$ haloalkyl, and $C_{1-4}$ alkoxy, or $R^7$ and $R^8$ and the atom(s) attached thereto together form a 3-6-membered ring; and n=1, 2 or 3; and L is (C═O), (O═S═O), ((C═O)—$CH_2$) or a bond; and $R^5$ is selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ alicyclic group, 3-10 membered heteroalicyclic group, $C_{6-12}$ bicyclic alicyclic group, 6-12 membered bicyclic heteroalicyclic group, $C_{8-15}$ tricyclic alicyclic group, 8-15 membered tricyclic heteroalicyclic group, $C_{5-8}$ aryl, 5-10 membered heteroaryl, $C_{7-11}$ bicyclic aryl, 7-11 membered bicyclic heteroaryl, —$C_{1-4}$ alkyl-($C_{3-7}$ alicyclic group), —$C_{1-4}$ alkyl-(3-10 membered heteroalicyclic group), —$C_{1-4}$ alkyl-($C_{6-12}$ bicyclic alicyclic group), —$C_{1-4}$ alkyl-(6-12 membered bicyclic heteroalicyclic group), —$C_{1-4}$ alkyl-($C_{8-15}$ tricyclic alicyclic group), —$C_{1-4}$ alkyl-(8-15 membered tricyclic heteroalicyclic group), —$C_{1-4}$ alkyl-($C_{5-8}$ aryl), —$C_{1-4}$ alkyl-(5-10 membered heteroaryl), —$N(R^{10})(R^{11})$, —$N(R^{10})(C(═O)R^{11})$, —$N(R^{10})(C(═O)—OR^{11})$, —$N(R^{12})(C(═O)—N(R^{10})(R^{11}))$, —C(═O)—N($R^{10}$)($R^{11}$), —C(═O)—$R^{12}$, —C(═O)—O$R^{12}$, —OC(═O)$R^{12}$, —N($R^{10}$)(S(═O)$_2$ $R^{11}$), —S(═O)$_2$—N($R^{10}$)($R^{11}$), —S$R^{12}$, and —O$R^{12}$, wherein the —S—$C_{1-4}$ alkyl, $C_{1-6}$ alkyl, $C_{1-6}$ alkoxy, $C_{1-6}$ haloalkoxy, $C_{2-8}$ alkenyl, $C_{2-8}$ alkynyl, $C_{3-7}$ alicyclic group, 3-10 membered heteroalicyclic group, $C_{6-12}$ bicyclic alicyclic group, 6-12 membered bicyclic heteroalicyclic group, $C_{8-15}$ tricyclic alicyclic group, 8-15 membered tricyclic heteroalicyclic group, $C_{5-8}$ aryl, 5-7 membered heteroaryl, $C_{7-11}$ bicycloaryl, 7-11 membered bicyclic heteroaryl, —$C_{1-4}$ alkyl-($C_{3-7}$ alicyclic group), —$C_{1-4}$ alkyl-(3-10 membered heteroalicyclic group), —$C_{1-4}$ alkyl-($C_{6-12}$ bicyclic alicyclic group), —$C_{1-4}$ alkyl-(6-12 membered bicyclic heteroalicyclic group), —$C_{1-4}$ alkyl-($C_{8-15}$ tricyclic alicyclic group), and —$C_{1-4}$ alkyl-(8-15 membered tricyclic heteroalicyclic group) are each optionally substituted with 0, 1, 2, 3 or 4 $R^{5a}$; and $R^{5a}$ is independently selected from halogen, —OH, —$NO_2$, —CN, —$SF_5$, —SH, —S—$C_{1-4}$ alkyl, oxo, $C_{1-4}$ alkyl, $C_{1-4}$ haloalkyl, $C_{1-4}$ alkoxy, $C_{1-4}$ haloalkoxy, $C_{2-8}$ alkenyl, $C_{2-8}$ alkynyl, $C_{3-7}$ alicyclic group, 3-10 membered heteroalicyclic group, $C_{5-8}$ aryl, 5-7 membered heteroaryl, —N($R^{13}$)($R^{14}$), —N($R^{13}$)(C(═O)$R^{14}$), —N($R^{13}$)(C(═O)—O$R^{14}$), —N($R^{15}$)(C(═O)—N($R^{13}$)($R^{14}$)), —C(═O)—N($R^{13}$)($R^{14}$), —C(═O)—$R^{15}$, —C(═O)—O$R^{15}$, —OC(═O)$R^{15}$, —N($R^{13}$)(S(═O)$_2$$R^{14}$), —S(═O)$_2$—N($R^{13}$)($R^{14}$), —S$R^{15}$, and —O$R^{15}$; and $R^{10}$, $R^{11}$, $R^{12}$, $R^{13}$, $R^{14}$ and $R^{15}$, at each occurrence, are each independently selected from H, $C_{1-6}$ alkyl, $C_{1-6}$ haloalkyl, $C_{3-7}$ alicyclic group, 3-10 membered heteroalicyclic group, $C_{5-8}$ aryl, 5-7 membered heteroaryl, $C_{7-11}$ bicycloaryl, 7-11 membered bicyclic heteroaryl, —$C_{1-4}$ alkyl-($C_{3-7}$ alicyclic group), —$C_{1-4}$ alkyl-(3-10 membered heteroalicyclic group), —$C_{1-4}$ alkyl-($C_{6-12}$ bicyclic alicyclic group), —$C_{1-4}$ alkyl-(6-12 membered bicyclic heteroalicyclic group), —$C_{1-4}$ alkyl-($C_{8-15}$ tricyclic alicyclic group), —$C_{1-4}$ alkyl-(8-15 membered tricyclic heteroalicyclic group), —$C_{1-4}$ alkyl-($C_{5-8}$ aryl), —$C_{1-4}$ alkyl-(5-10 membered heteroaryl), wherein each substituent listed in the group is optionally substituted with 0, 1, 2, 3, or 4 substituents each independently selected from a group consisting of: halogen, —OH, —$NH_2$, —NH($CH_3$), —N($CH_3$)$_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ alicyclic group, 3-10 membered heteroalicyclic group, $C_{5-8}$ aryl, 5-7 membered heteroaryl, $C_{7-11}$ bicycloaryl, 7-11 membered bicyclic heteroaryl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy;

or $R^{10}$, $R^{11}$, and the atom(s) attached thereto together form a 3-14-membered ring;

or $R^{13}$, $R^{14}$, and the atom(s) attached thereto together form a 3-14-membered ring.

Unless otherwise indicated, the term "a compound as shown by Formula (I)", "a compound of Formula (I)", "a compound of Formula (II)", "a compound of Formula (III)", "a compound of Formula (IV)" or "a compound according to the present application" also encompasses any optical isomer, geometric isomer, tautomer or a mixture of various isomers of the compound.

The term "optical isomer" refers that when a compound has one or more chiral centers, each chiral center may have an R configuration or an S configuration, and the various isomers thus constituted are known as an optical isomer. Optical isomers comprise all diastereomers, enantiomers, meso forms, racemates or mixtures thereof. For example, optical isomers can be separated by a chiral chromatography or by chiral synthesis.

The term "geometric isomer" refers that when a double bond is present in a compound, the compound may exist as a cis isomer, a trans isomer, an E isomer, or a Z isomer. A geometric isomer comprises a cis isomer, trans isomer, E isomer, Z isomer, or a mixture thereof.

The term "tautomer" refers to an isomer that is formed by rapid movement of an atom at two positions in a single molecule. It will be understood by those skilled in the art that tautomers can be mutually transformed, and in a certain state, may coexist by reaching an equilibrium state.

Unless otherwise indicated, reference to "a compound as shown by Formula (I)", "a compound of Formula (I)", "a compound of Formula (II)", "a compound of Formula (III)", "a compound of Formula (IV)" or "a compound according to the present application" herein also encompasses isotopically-labeled compounds obtained by replacing any atom of the compound with its isotopic atom.

Examples of isotopes suitable for inclusion in the compounds of the invention include isotopes of hydrogen, such as $^{2}$H (D) and $^{3}$H (T), of carbon, such as $^{11}$C, $^{13}$C and $^{14}$C, of chlorine, such as $^{36}$Cl, of fluorine, such as $^{18}$F, of iodine, such as $^{123}$I and $^{125}$I, of nitrogen, such as $^{13}$N and $^{15}$N, of oxygen, such as $^{15}$O, $^{17}$O and $^{18}$O, and of sulphur, such as $^{35}$S.

The isotopically-labelled compounds, for example, those incorporating a radioactive isotope, are useful in drug and/or substrate tissue distribution studies. The radioactive isotopes deuterium, i.e. $^{2}$H, and carbon-14, i.e. $^{14}$C, are particularly useful for this purpose in view of their ease of incorporation and ready means of detection.

Substitution with heavier isotopes such as deuterium, i.e. D, may afford certain therapeutic advantages resulting from greater metabolic stability, for example, increased in vivo half-life or reduced dosage requirements, and hence may be preferred in some circumstances. Thus, in some embodiments, the compounds according to the present application are isotopically labeled compounds, wherein H is optionally replaced by D at each occurrence.

Substitution with positron emitting isotopes, such as $^{11}$C, $^{18}$F, $^{15}$O and $^{13}$N, can be useful in Positron Emission Topography (PET) studies for examining substrate receptor occupancy.

The isotopically-labeled compounds can generally be prepared by conventional techniques known to those skilled in the art or using an appropriate isotopically-labeled reagents in place of the non-labeled reagent previously employed.

The compounds according to the present application may exist in the form of a pharmaceutically acceptable salt.

The term "pharmaceutically acceptable" means that the corresponding compound, vehicle or molecule is suitable for administration to humans. Preferably, the term refers to the use for mammalian, preferably human approved by any national regulatory agency such as CFDA (China), EMEA (Europe), FDA (USA), etc.

The pharmaceutically acceptable salt include acid addition salts and base addition salts thereof. Suitable acid addition salts are formed from acids that form non-toxic salts. Examples include but are not limited to: acetate, adipate, aspartate, benzoate, benzenesulfonate, bicarbonate/carbonate, bisulfate/sulfate, borate, camphor sulfonate, citrate, cyclohexamine sulfonate, ethanedisulfonate, formate, fumarate, glucoheptonate, gluconate, glucuronate, hexafluorophosphate, 2-(4-hydroxybenzyl) benzoate, hydrochloride/chloride, hydrobromide/bromide, hydroiodide/iodide, 2-isethionate, lactate, malate, maleate, malonate, methanesulfonate, methyl sulfate, naphthalate, 2-naphthalenesulfonate, nicotinate, nitrate, orotate, oxalate, palmitate, phosphate/hydrogen phosphate/dihydrogen phosphate, pyroglutamate, glucarate, stearate, salicylate, tannate, tartrate, tosylate and trifluoroacetate. Suitable base addition salts are formed from bases that form non-toxic salts. Examples thereof include, but are not limited to: aluminum, arginine, calcium, choline, diethylamine, diethanolamine, glycine, lysine, magnesium, meglumine, ethanolamine, potassium, sodium, tromethamine, and zinc salts. It is also possible to form half salts of acids and bases, such as hemisulfate and hemicalcium salts. For a review of suitable salts, please refer to Handbook of Pharmaceutical Salts: Properties, Selection and Use by Stahl and Wermuth (Wiley-VCH, 2002). Methods for preparing pharmaceutically acceptable salts of the compounds described herein are known to those skilled in the art.

Moreover, the compounds according to the present application may exist in unsolvated form as well as solvated forms with pharmaceutically acceptable solvents such as water, ethanol and the like. The compounds may exist in one or more crystalline forms, or in an amorphous form. These forms are included within the scope of the invention.

The present application further comprises prodrug of the compounds according to the present application. The "prodrug" refers to a derivative that is converted into a compound according to the present disclosure by a reaction with enzymes, gastric acid, and the like in a living body under physiological conditions, for example, through oxidation, reduction, hydrolysis, and the like catalyzed by enzymes. Thus, some derivatives of the compounds according to the present application may have little or no pharmacological activity on their own, and can be converted into compounds according to the present application with the desired activity when administered to the body or on the body of a patient.

The present application further comprises metabolite of the compounds according to the present application. The "metabolite" refers to all molecules derived from any compound according to the present disclosure in a cell or organism, preferably a human.

As used herein, the term "substituted" means that one or more (preferably 1 to 5, more preferably 1 to 3) hydrogen atoms in a group are independently replaced by a corresponding number of substituents.

As used herein, the term "independently" means that when the number of substituents is more than one, these substituents may be the same or different.

As used herein, the term "optional" or "optionally" means that the event described therein may or may not occur. For example, an "optionally substituted" group means that the group may be unsubstituted or substituted.

The term "halogen" or "halo" refers to —F, —Cl, —Br, or —I.

As used herein, the term "alkyl" refers to saturated aliphatic hydrocarbons, including straight and branched chains. In some embodiments, the alkyl group has 1-8, or 1-6, or 1-4, or 1-3 carbon atoms. For example, the term "$C_{1-8}$ alkyl" refers to a straight or branched chain group of atoms having 1-8 carbon atoms. The term "$C_{1-8}$ alkyl" includes the terms "$C_{1-6}$ alkyl", "$C_{1-3}$ alkyl" and "$C_{1-4}$ alkyl" in its definition. Examples of alkyl groups include, but are not limited to, methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl, and the like. The alkyl group may be optionally substituted with one or more (for example, 1 to 5) suitable substituent(s).

As used herein, the term "alkenyl" refers to an aliphatic hydrocarbon having at least one carbon-carbon double bond, including straight and branched chains having at least one carbon-carbon double bond. In some embodiments, alkenyl groups have 2-8 carbon atoms, 2-6 carbon atoms, 3-6 carbon atoms, or 2-4 carbon atoms. For example, the term "$C_{2-8}$ alkenyl" refers to a linear or branched unsaturated atomic group (having at least one carbon-carbon double bond) having 2-8 carbon atoms. The double bond may or may not be the point of attachment of another group. Alkenyl groups include, but are not limited to, vinyl, 1-propenyl, 2-propenyl, 2-methyl-2-propenyl, butenyl, pentenyl, 3-hexenyl, and the like. Alkenyl groups may be optionally substituted with one or more (for example, 1 to 5) suitable substituent(s). When the compound of formula (I) contains an alkenyl group, the alkenyl group may be present in the pure E form, the pure Z form, or any mixture thereof.

As used herein, the term "alkynyl" refers to an aliphatic hydrocarbon having at least one carbon-carbon triple bond, including straight and branched chains having at least one carbon-carbon triple bond. In some embodiments, an alkynyl group has 2-8 carbon atoms, 2-6 carbon atoms, 3-6 carbon atoms, or 2-4 carbon atoms. For example, the term "$C_{2-8}$ alkynyl" refers to a linear or branched unsaturated atomic group (having at least one carbon-carbon triple bond) having 2-8 carbon atoms. The triple bond may or may not be the point of attachment of another group. Alkynyl groups include, but are not limited to, ethynyl, 1-propynyl, 2-propynyl, 2-methyl-2-propynyl, butynyl, pentynyl, 3-hexynyl, and the like. The alkynyl group may be optionally substituted with one or more (for example, 1 to 5) suitable substituent(s).

As used herein, the term "$C_{3-8}$ alicyclic group" refers to an alicyclic group having 3-8 ring-forming carbon atoms. The term "$C_{3-7}$ alicyclic group" refers to an alicyclic group having 3-7 ring-forming carbon atoms. The term "$C_{3-6}$ alicyclic group" refers to an alicyclic group having 3-6 ring-forming carbon atoms. The alicyclic group may be a monocyclic ring. The definition of alicyclic group also includes an unsaturated non-aromatic alicyclic group. Examples of alicyclic group are, for example, cyclopropyl, cyclobutyl, cyclopentyl, cyclohexyl, cyclohexenyl, cycloheptyl, cyclooctyl, cyclohexadienyl, cyclopentenyl, cycloheptenyl and cyclooctenyl. The alicyclic group may be optionally substituted with one or more suitable substituent(s).

As used herein, the term "$C_{6-12}$ bicyclic alicyclic group" is an alicyclic group containing two rings with 6-12 ring-forming carbon atoms. The bicyclic alicyclic group may be fused or may include a bridged bicyclic alicyclic group system.

As used herein, the term "$C_{8-15}$ membered tricyclic alicyclic group" is an alicyclic group containing three rings with 8-15 ring-forming carbon atoms. The tricyclic alicyclic group may be fused or bridged.

As used herein, the term "n-membered heteroalicyclic group" refers to an alicyclic group having m ring-forming carbon atoms and (n-m) ring-forming heteroatoms, the heteroatoms being selected from O, S and N. For example, the term "4-8-membered heteroalicyclic group" refers to a heteroalicyclic group substituent containing a total of 4 to 8 ring atoms, at least one of which is a heteroatom; the term "4-6-membered heteroalicyclic group" refers to a heteroalicyclic group substituent containing a total of 4 to 6 ring atoms, at least one of which is a heteroatom; and the term "3-10-membered heteroalicyclic group" refers to a heteroalicyclic group substituent containing a total of 3 to 10 ring atoms, at least one of which is a heteroatom. The term "n-membered bicyclic heteroalicyclic group" refers to a bicyclic heteroalicyclic group having m ring-forming carbon atoms and (n-m) ring-forming heteroatoms, the heteroatoms being selected from O, S and N. Examples of heteroalicyclic group includes, but not limited to, azetidinyl, thietidinyl, dihydrofuranyl, dihydrothiophenyl, tetrahydrothienyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyrimidinyl tetrahydrothiopyranyl, tetrahydrothiazinyl, tetrahydrothiadiazinyl, tetrahydrooxazolyl, morpholinyl, oxetanyl, tetrahydrodiazinyl, oxazinyl, oxathiadiazinyl, quinuclidinyl, benzodipyranyl (chromanyl), isobenzodipyranyl (isochromanyl), dihydrobenzodioxinyl, benzodioxolyl, benzoxazinyl, dihydroindolyl, dihydrobenzofuranyl, tetrahydroquinolinyl, isochromanyl, dihydro-1H-isoindolyl, 2-azabicyclo[2.2.1]heptanoyl, 3-azabicyclo[3.1.0]hexyl, 3-azabicyclo[4.1.0]heptyl, oxacycloheptyl, thiacycloheptyl, azacycloheptyl, and the like. The heteroalicyclic group may be optionally substituted with one or more suitable substituent(s).

As used herein, the term "$C_{5-8}$ aryl" refers to an aryl group having an aromatic ring containing 5-8 carbon atoms, for example phenyl.

As used herein, the term "n-membered heteroaryl" refers to a heteroaryl group having m aromatic ring-forming carbon atoms and (n-m) aromatic ring-forming heteroatoms, the heteroatoms being selected from O, S and N. For example, 5-7 membered heteroaryl includes but not limited to furanyl, thienyl, pyrrolyl, thiazolyl, pyrazolyl, imidazolyl, pyridinyl, pyranyl, pyridazinyl, pyrimidinyl, pyrazinyl. The heteroaryl may be optionally substituted with one or more suitable substituent(s).

As used herein, the term "$C_{7-11}$ bicycloaryl" refers to a bicycloaryl group having 7-11 carbon atoms, such as naphthalene, indene and the like. The bicycloaryl may be optionally substituted with one or more suitable substituent(s).

As used herein, the term "n-membered bicycloheteroaryl" refers to a bicycloheteroaryl group having m carbon atoms forming an aromatic bicyclic ring and (n-m) heteroatoms forming an aromatic bicyclic ring, and the heteroatoms are selected from O, S and N. For example, 7-11 membered bicycloheteroaryl includes, but not limited to, quinolinyl, isoquinolinyl, indolyl, purinyl, benzothiazolyl. The bicycloheteroaryl may be optionally substituted with one or more suitable substituent(s).

As used herein, the term "11-15 membered tricyclyl" includes but not limited to acridine and the like. The 11-15 membered tricyclyl may be optionally substituted with one or more suitable substituent(s).

As used herein, the term "haloalkyl" refers to an alkyl group having one or more halogen substituent(s) (up to perhaloalkyl, that is, each hydrogen atom of the alkyl is replaced by a halogen atom). For example, the term "$C_{1-6}$ haloalkyl" refers to a $C_{1-6}$ alkyl group with one or more halogen substituent(s) (up to perhaloalkyl, that is, each hydrogen atom of the alkyl group is replaced by a halogen atom). As another example, the term "$C_{1-4}$ haloalkyl" refers to a $C_{1-4}$ alkyl group with one or more halogen substituent(s) (up to perhaloalkyl, that is, each hydrogen atom of the alkyl group is replaced by a halogen atom); the term "$C_{1-3}$ haloalkyl" refers to a $C_{1-3}$ alkyl group with one or more halogen substituent(s) (up to perhaloalkyl, that is, each hydrogen atom of the alkyl group is replaced by a halogen atom); and the term "$C_{1-2}$ haloalkyl" refers to a $C_{1-2}$ alkyl group (i.e. methyl or ethyl) with one or more halogen substituent(s) (up to perhaloalkyl, that is, each hydrogen atom of the alkyl group is replaced by a halogen atom). As another example, the term "$C_1$ haloalkyl" refers to a methyl group with 1, 2, or 3 halogen substituent(s). Examples of haloalkyl groups include: $CF_3$, $C_2F_5$, $CHF_2$, $CH_2F$, $CH_2CF_3$, $CH_2Cl$, and the like.

As used herein, the term "alkoxy" refers to alkyl with a single bond attached to an oxygen atom. The point of attachment of the alkoxy group to a molecule is through the oxygen atom. Alkoxy can be described as alkyl-O—. The term "$C_{1-6}$ alkoxy" refers to a linear or branched alkoxy group containing 1 to 6 carbon atoms. The term "$C_{1-6}$ alkoxy" includes the term "$C_{1-3}$ alkoxy" in its definition. Alkoxy includes, but not limited to, methoxy, ethoxy, propoxy, isopropoxy, butoxy, hexoxy, and the like. The alkoxy group may be optionally substituted with one or more suitable substituent(s).

As used herein, the term "3-14-membered ring" refers to a saturated or unsaturated ring system with 3-14 ring-forming atoms.

Herein, a numerical range relating to the number of substituents, the number of carbon atoms, or the number of ring members represents an enumeration of all integers in the range, and the range is only a simplified representation thereof. For example: "4 to 6-membered ring" means a 4, 5 or 6-membered ring; "5 to 7-membered ring" means a 5, 6 or 7-membered ring; "7 to 11-membered ring" means a 7, 8, 9, 10 or 11-membered ring; "4 to 8-membered ring" means a 4, 5, 6, 7 or 8-membered ring; "3 to 10-membered ring" means a 3, 4, 5, 6, 7, 8, 9 or 10-membered ring; "3 to 14-membered ring" means a 3, 4, 5, 6, 7, 8, 9, 10, 11, 12, 13 or 14-membered ring; "$C_{1-3}$" means 1 ($C_1$), 2 ($C_2$), or 3 ($C_3$) carbon atoms; "$C_{1-4}$" means 1 ($C_1$), 2 ($C_2$), 3 ($C_3$) or 4 ($C_4$) carbon atoms; "$C_{3-6}$" means 3 ($C_3$), 4 ($C_4$), 5 ($C_5$), or 6 ($C_6$) carbon atoms; "$C_{3-8}$" means 3 ($C_3$), 4 ($C_4$), 5 ($C_5$), 6 ($C_6$), 7 ($C_7$), or 8 ($C_8$) carbon atoms; "$C_{5-7}$" means 5 ($C_5$), 6 ($C_6$), or 7 ($C_7$) carbon atoms; "$C_{7-11}$" means 7 ($C_7$), 8 ($C_8$), 9 ($C_9$), 10 ($C_{10}$), or 11 ($C_{11}$) carbon atoms. Thus, a numerical range associated with the number of substituents, the number of carbon atoms, or the number of ring members also encompasses any one of its subranges, and each subrange is also considered to be disclosed herein.

In formula (I) as described above, $R^1$ is selected from H, halogen, —CN, —OH, —$NO_2$, —$NR^7R^8$, $C_{1-4}$ alkyl, $C_{1-4}$ haloalkyl, $C_{1-4}$ alkoxy, $C_{3-6}$ alicyclic group, and 4-6 membered heteroalicyclic group.

In some embodiments, $R^1$ is H.

In some embodiments, $R^1$ is halogen, e.g., $R^1$ is selected from F, Cl, Br, and I.

In some embodiments, $R^1$ is —CN.

In some embodiments, $R^1$ is —$NO_2$.

In some embodiments, $R^1$ is $C_{1-3}$ alkyl or $C_{1-3}$ haloalkyl, e.g., $R^1$ is selected from methyl, ethyl, propyl, and isopropyl optionally substituted with one or more halogen atoms (e.g., fluorine, chlorine, bromine, iodine).

In some embodiments, $R^1$ is $C_{1-3}$ alkoxy, e.g., $R^1$ is selected from methoxy, ethoxy, propoxy, and isopropoxy.

In some embodiments, $R^1$ is $C_{3-6}$ alicyclic group, e.g., $R^1$ is selected from cyclopropyl, cyclobutyl, cyclopentyl, cyclohexyl, and cyclohexenyl.

In some embodiments, $R^1$ is 4-6 membered heteroalicyclic group, e.g., $R^1$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

In some embodiments, $R^1$ is —$NR^7R^1$, wherein $R^7$ and $R^8$ at each occurrence are each independently selected from: H, $C_{1-3}$ alkyl (e.g., methyl, ethyl, propyl, isopropyl, etc.), $C_{1-3}$ haloalkyl (e.g., methyl, ethyl, propyl, isopropyl substituted with one or more halogen atoms selected from fluorine, chlorine, bromine, iodine), $C_{1-3}$ alkoxy (e.g., methoxy, ethoxy, propoxy, isopropoxy), or $R^7$, $R^8$ and N atom attached thereto together form a 3-6-membered ring (e.g., pyrrole, pyridine, pyrimidine, imidazole, pyrazole, pyrrolidine, hexahydropyridine, etc.).

It should be understood that any of the above embodiments of $R^1$ may be combined with any of the embodiments of $R^2$, $R^3$, $R^5$, $R^6$, X, L and n as described above and below in arbitrary combination.

In formula (I) as described above, $R^2$ is selected from H, halogen, —CN, —OH, —$NO_2$, —$NR^7R^1$, $C_{1-4}$ alkyl, $C_{1-4}$ haloalkyl, $C_{1-4}$ alkoxy, $C_{3-6}$ alicyclic group, and 4-6 membered heteroalicyclic group.

In some embodiments, $R^2$ is H.

In some embodiments, $R^2$ is halogen, e.g., $R^2$ is selected from F, Cl, Br, and I.

In some embodiments, $R^2$ is —CN.

In some embodiments, $R^2$ is —$NO_2$.

In some embodiments, $R^2$ is $C_{1-3}$ alkyl or $C_{1-3}$ haloalkyl, e.g., $R^2$ is selected from methyl, ethyl, propyl, and isopropyl optionally substituted with one or more halogen atoms (e.g., fluorine, chlorine, bromine, iodine).

In some embodiments, $R^2$ is a $C_{1-3}$ alkoxy, e.g., $R^2$ is selected from methoxy, ethoxy, propoxy, and isopropoxy.

In some embodiments, $R^2$ is $C_{3-6}$ alicyclic group, e.g., $R^2$ is selected from cyclopropyl, cyclobutyl, cyclopentyl, cyclohexyl, and cyclohexenyl.

In some embodiments, $R^2$ is 4-6 membered heteroalicyclic group, e.g., $R^2$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

In some embodiments, $R^2$ is —$NR^7R^8$, wherein $R^7$ and $R^8$ at each occurrence are each independently selected from: H, $C_{1-3}$ alkyl (e.g., methyl, ethyl, propyl, isopropyl, etc.), $C_{1-3}$ haloalkyl (e.g., methyl, ethyl, propyl, isopropyl substituted with one or more halogen atoms selected from fluorine, chlorine, bromine, iodine), $C_{1-3}$ alkoxy (e.g., methoxy, ethoxy, propoxy, isopropoxy), or $R^7$, $R^8$ and N atom attached thereto together form a 3-6-membered ring (e.g., pyrrole, pyridine, pyrimidine, imidazole, pyrazole, pyrrolidine, hexahydropyridine, etc.).

It should be understood that any of the above embodiments of $R^2$ may be combined with any of the embodiments of $R^1$, $R^3$, $R^5$, $R^6$, X, L and n as described above and below in arbitrary combination.

In some embodiments, $R^1$ and $R^2$ may be the same. For example, $R^1$ and $R^2$ both are halogen, such as Cl; further, for example, $R^1$ and $R^2$ both are methyl. In a preferred embodiment, $R^1$ and $R^2$ both are Cl. In a preferred embodiment, $R^1$ and $R^2$ both are H.

In other embodiments, $R^1$ and $R^2$ may be different.

In formula (I) as described above, $R^3$ is selected from H, $C_{1-4}$ alkyl, $C_{1-4}$ haloalkyl, $C_1$. 4 alkoxy, $C_{3-6}$ alicyclic group, and 4-6 membered heteroalicyclic group.

In some embodiments, $R^3$ is H.

In some embodiments, $R^3$ is $C_{1-3}$ alkyl or $C_{1-3}$ haloalkyl, e.g., $R^3$ is selected from methyl, ethyl, propyl, and isopropyl optionally substituted with one or more halogen atoms (e.g., fluorine, chlorine, bromine, iodine).

In some embodiments, $R^3$ is a $C_{1-3}$ alkoxy, e.g., $R^3$ is selected from methoxy, ethoxy, propoxy, and isopropoxy.

In some embodiments, $R^3$ is $C_{3-6}$ alicyclic group, e.g., $R^3$ is selected from cyclopropyl, cyclobutyl, cyclopentyl, cyclohexyl, and cyclohexenyl.

In some embodiments, $R^3$ is 4-6 membered heteroalicyclic group, e.g., $R^3$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

In some embodiments, $R^3$ is methyl.

It should be understood that any of the above embodiments of $R^3$ may be combined with any of the embodiments of $R^1$, $R^2$, $R^5$, $R^6$, X, L and n as described above and below in arbitrary combination.

There may be 1, 2, or 3 $R^6$(s) present in formula (I) as described above where each $R^6$ is each independently selected from H, halogen, —CN, —OH, —$NO_2$, —$NR^7R^1$, $C_{1-4}$ alkyl, $C_{1-4}$ haloalkyl, $C_{1-4}$ alkoxy, $C_{3-6}$ alicyclic group, and 4-6 membered heteroalicyclic group in which $R^7$ and $R^8$ at each occurrence are each independently selected from: H, $C_{1-6}$ alkyl, $C_{1-4}$ haloalkyl, $C_{1-4}$ alkoxy, or $R^7$, $R^8$ and N atom attached thereto together form a 3-6-membered ring.

In some preferred embodiments, $R^6$ is H.

In some embodiments, $R^6$ is halogen, e.g., $R^6$ is selected from F, Cl, Br, and I.

In some embodiments, $R^6$ is —CN, —OH or —$NO_2$.

In some embodiments, $R^6$ is $C_{1-3}$ alkyl or $C_{1-3}$ haloalkyl, e.g., $R^6$ is selected from methyl, ethyl, propyl, and isopropyl optionally substituted with one or more halogen atoms (e.g., fluorine, chlorine, bromine, iodine).

In some embodiments, $R^6$ is $C_{1-3}$ alkoxy, e.g., $R^6$ is selected from methoxy, ethoxy, propoxy, and isopropoxy.

In some embodiments, $R^6$ is $C_{3-6}$ alicyclic group, e.g., $R^6$ is selected from cyclopropyl, cyclobutyl, cyclopentyl, cyclohexyl, and cyclohexenyl.

In some embodiments, $R^6$ is 4-6 membered heteroalicyclic group, e.g., $R^6$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

In some embodiments, $R^6$ is —$NR^7R^8$, wherein $R^7$ and $R^8$ at each occurrence are each independently selected from: H, $C_{1-3}$ alkyl (e.g., methyl, ethyl, propyl, isopropyl, etc.), $C_{1-3}$ haloalkyl (e.g., methyl, ethyl, propyl, isopropyl substituted with one or more halogen atoms selected from fluorine, chlorine, bromine, iodine), $C_{1-3}$ alkoxy (e.g., methoxy, ethoxy, propoxy, isopropoxy), or $R^7$, $R^8$ and N atom attached thereto together form a 3-6-membered ring (e.g., pyrrole, pyridine, pyrimidine, imidazole, pyrazole, pyrrolidine, hexahydropyridine, etc.).

In some embodiments, $R^6$ is dimethylamino, diethylamino, methylethylamino.

In some preferred embodiments, one $R^6$ is present.

It should be understood that any of the above embodiments of $R^6$ may be combined with any of the embodiments of $R^1$, $R^2$, $R^3$, $R^5$, X, L and n as described above and below in arbitrary combination.

In formula (I) as described above, X is O, S, or ($NR^4$), wherein $R^4$ is selected from: H, $C_{1-4}$ alkyl, $C_{1-4}$ haloalkyl, $C_{1-4}$ alkoxy, $C_{3-6}$ alicyclic group, and 4-6 membered heteroalicyclic group.

In some embodiments, X is O.

In some embodiments, X is S.

In some embodiments, X is imino, i.e., —(NH)—.

In some embodiments, X is —(N($CH_3$))—.

It should be understood that any of the above embodiments of X can be combined with any of the embodiments of $R^1$, $R^2$, $R^3$, $R^5$, $R^6$, L and n as described above and below in arbitrary combination.

In formula (I) as described above, n is 1, 2, or 3.

In some embodiments, n is 1.

In some embodiments, n is 2.

In some embodiments, n is 3.

It should be understood that any of the above embodiments of n may be combined with any of the embodiments of $R^1$, $R^2$, $R^3$, $R^5$, $R^6$, L, and X as described above and below in arbitrary combination.

In formula (I) as described above, L is (C═O), (O═S═O), ((C═O)—$CH_2$), or a bond.

In some embodiments, L is —(C═O)—.

In some embodiments, L is —(O═S═O)—.

In some embodiments, L is —((C═O)—$CH_2$)—.

In some embodiments, L is a covalent bond.

It should be understood that any of the above embodiments of L can be combined with any of the embodiments of $R^1$, $R^2$, $R^3$, $R^5$, $R^6$, n and X as described above and below in arbitrary combiantion.

In formula (I) as described above, $R^5$ can be any substituent commonly used in organic chemistry, which is not particularly limited.

In some embodiments, $R^5$ is $C_{1-6}$ alkyl. For example, $R^5$ is selected from methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl.

In some embodiments, $R^5$ is $C_{3-7}$ alicyclic group. For example, $R^5$ is selected from cyclopropyl, cyclobutyl, cyclopentyl, cyclohexyl, cyclohexenyl, cycloheptyl, cyclohexadienyl, cyclopentenyl, cycloheptenyl.

In some embodiments, $R^5$ is 3-10 membered heteroalicyclic group. For example, $R^5$ is selected from azetidinyl, thietidinyl, dihydrofuranyl, dihydrothienyl, tetrahydrothienyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiopyranyl, tetrahydrothiazinyl, tetrahydrothiadiazinyl, tetrahydrooxazolyl, morpholinyl, oxetanyl, tetrahydrodiazinyl, oxazinyl, oxathiadiazinyl, quinuclidinyl, benzodipyranyl, isobenzodipyranyl, dihydrobenzodioxinyl, benzodioxopentenyl, benzoxazinyl, dihydroindolyl, dihydrobenzofuranyl, tetrahydroquinolinyl, isochromanyl, dihydro-1H-isoindolyl, oxepanyl, thiepanyl, and azepanyl.

In some embodiments, $R^5$ is H, halogen, —OH, —$NO_2$, —CN, —$SF_5$, or —SH.

In some embodiments, $R^5$ is selected from —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl.

In some embodiments, $R^5$ is selected from $C_{5-8}$ aryl (e.g., phenyl), 5-10-membered heteroaryl (e.g., furanyl, thienyl, pyrrolyl, thiazolyl, pyrazolyl, imidazolyl, pyridinyl, pyranyl, pyridazinyl, pyrimidinyl, pyrazinyl, etc.), —$C_{1-4}$ alkyl-($C_{5-8}$ aryl), —$C_{1-4}$ alkyl-(5-10-membered heteroaryl).

In some embodiments, $R^5$ is selected from —N($R^{10}$)($R^{11}$), —N($R^{10}$)(C(═O)$R^{11}$), —N($R^{10}$)(C(═O)—O$R^{11}$), —N($R^{12}$)(C(═O)—N($R^{10}$)($R^{11}$)), —C(═O)—N($R^{10}$)($R^{11}$), —C(═O)—$R^{12}$, —C(═O)—O$R^{12}$, —OC(═O)$R^{12}$, —N($R^{10}$)(S(═O)$_2R^{11}$), —S(═O)$_2$—N($R^{10}$)($R^{11}$), —S$R^{12}$, and —O$R^{12}$, wherein $R^{10}$, $R^{11}$, and $R^{12}$ at each occurrence are each independently selected from: H, $C_{1-6}$ alkyl, $C_{1-6}$ haloalkyl, $C_{3-7}$ alicyclic group, 3-10-membered heteroalicyclic group, $C_{5-8}$ aryl, 5-7-membered heteroaryl, $C_{7-11}$ bicyclic aryl, 7-11-membered bicyclic heteroaryl, —$C_{1-4}$ alkyl-($C_{3-7}$ alicyclic group), —$C_{1-4}$ alkyl-(3-10-membered heteroalicyclic group), —$C_{1-4}$ alkyl-($C_{6-12}$ bicyclic alicyclic group), —$C_{1-4}$ alkyl-(6-12-membered bicyclic heteroalicyclic group), —$C_{1-4}$ alkyl-($C_{8-15}$ tricyclic alicyclic group), —$C_{1-4}$ alkyl-(8-15-membered tricyclic heteroalicyclic group), —$C_{1-4}$ alkyl-($C_{5-8}$ aryl), and —$C_{1-4}$ alkyl-(5-10-membered heteroaryl), wherein each substitute within the group is optionally substituted with 0, 1, 2, 3, or 4 substituents each independently selected from the following groups: halogen, —OH, —$NH_2$, —NH($CH_3$), —N($CH_3$)$_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ alicyclic group, 3-10-membered heteroalicyclic group, $C_{5-8}$ aryl, 5-7-membered heteroaryl, $C_{7-11}$ bicyclic aryl, 7-11-membered bicyclic heteroaryl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy, and $C_{1-4}$ haloalkoxy; or $R^{10}$, $R^{11}$, and the atom(s) attached thereto together form a 3-14-membered ring.

Any exemplary groups enumerated above for $R^5$ are to be understood as being optionally substituted; i.e., where appropriate, any of the groups given above for $R^5$ may be optionally substituted with 0, 1, 2, 3 or 4 $R^{5a}$(s), and $R^{5a}$ is independently selected from halogen, —OH, —$NO_2$, —CN, —$SF_5$, —SH, —S—$C_{1-4}$ alkyl, oxo, $C_{1-4}$ alkyl, $C_{1-4}$ haloalkyl, $C_{1-4}$ alkoxy, $C_{1-4}$ haloalkoxy, $C_{2-8}$ alkenyl, $C_{2-8}$ alkynyl, $C_{3-7}$ alicyclic group, 3-10-membered heteroalicyclic group, $C_{5-8}$ aryl, 5-7-membered heteroaryl, —N($R^{13}$)($R^{14}$), —N($R^{13}$)(C(═O)$R^{14}$), —N($R^{13}$)(C(═O)—O$R^{14}$), —N($R^{15}$)(C(═O)—N($R^{13}$)($R^{14}$)), —C(═O)—N($R^{13}$)($R^{14}$), —C(═O)—$R^{15}$, —C(═O)—O$R^{15}$, —OC(═O)$R^{15}$, —N($R^{13}$)(S(═O)$_2R^{14}$), —S(═O)$_2$—N($R^{13}$)($R^{14}$), —S$R^{15}$, and —O$R^{15}$, where $R^{13}$, $R^{14}$, and $R^{15}$ at each occurrence are each independently selected from: H, $C_{1-6}$ alkyl, $C_{1-6}$ haloalkyl, $C_{3-7}$ alicyclic group, 3-10-membered heteroalicyclic group, $C_{5-8}$ aryl, 5-7-membered heteroaryl, $C_{7-11}$ bicyclic aryl, 7-11-membered bicyclic heteroaryl, —$C_{1-4}$ alkyl-($C_{3-7}$ alicyclic group), —$C_{1-4}$ alkyl-(3-10-membered heteroalicylic group), —$C_{1-4}$ alkyl-($C_{6-12}$ bicyclic alicyclic group), —$C_{1-4}$ alkyl-(6-12-membered bicyclic heteroalicyclic group), —$C_{1-4}$ alkyl-($C_{8-15}$ tricyclic alicylic group), —$C_{1-4}$ alkyl-(8-15-membered tricyclic heteroalicyclic group), —$C_{1-4}$ alkyl-($C_{5-8}$ aryl), and —$C_{1-4}$ alkyl-(5-10-membered heteroaryl), wherein each substituent within the group is optionally substituted with 0, 1, 2, 3 or 4 substituents each independently selected from the group consisting of: halogen, —OH, —$NH_2$, —NH($CH_3$), —N($CH_3$)$_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ alicyclic group, 3-10-membered alicyclic group, $C_{5-8}$ aryl, 5-7-membered heteroaryl, $C_{7-11}$ bicyclic aryl, 7-11-membered bicyclic heteroaryl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy, and $C_{1-4}$ haloalkoxy; or $R^{13}$, $R^{14}$, and the atom(s) attached thereto together form a 3-14-membered ring.

In some preferred embodiments, $R^5$ is selected from methyl, ethyl, propyl, isopropyl, and cyclobutyl groups. The methyl, ethyl, propyl, isopropyl or cyclobutyl group may optionally be substituted with 0, 1 or 2 substituents each independently selected from a group consisting of: methyl, ethyl, cyclopentyl, cyclopropyl, —CN, —OH, morpholinyl, piperidinyl, and these substituents may further optionally be substituted with 0, 1 or 2 substituents each independently selected from a group consisting of: methyl, ethyl, cyclopentyl, cyclopropyl, —CN, and —OH. For example, in some preferred embodiments, $R^5$ is selected from (1-hydroxycyclopropyl)ethyl, 3-hydroxycyclobutyl, 2-cyanoethyl, 2-hydroxyethyl, 2-cyano-1-cyclopentyl ethyl, 1-cyanopropane, 2-morpholinoethyl, ethyl, and (1-methylpiperidin-4-yl)methyl.

In some preferred embodiments, $R^5$ is selected from halogen, such as F.

In some preferred embodiments, $R^5$ is selected from piperazinyl, morpholinyl, pyrrolidinyl, piperidinyl and azetidinyl, the piperazinyl, pyrrolidinyl, piperidinyl and azetidinyl being optionally substituted with 0, 1 or 2 substituents each independently selected from a group consisting of: methyl, ethyl, cyclopentyl, cyclopropyl, —CN, and —OH. In some preferred embodiments, $R^5$ is selected from methyl, ethyl, propyl, isopropyl, and cyclobutyl groups, in which said methyl, ethyl, propyl, isopropyl or cyclobutyl groups may optionally be substituted with 0, 1 or 2 substituents each independently selected from a group consisting of: methyl, ethyl, cyclopentyl, cyclopropyl, —CN, —OH, morpholinyl, and piperidinyl, and these substituents are further optionally substituted with 0, 1 or 2 substituents each independently selected from a group consisting of: methyl, ethyl, cyclopentyl, cyclopropyl, —CN, and —OH.

In some preferred embodiments, $R^5$ is selected from piperazinyl, morpholinyl, pyrrolidinyl, piperidinyl, and azetidinyl. For example, in some preferred embodiments, $R^5$ is selected from 3,5-dimethylpiperazinyl, morpholinyl, 3-hydroxypyrrolidinyl, 4-methylpiperazinyl, 4-ethylpiperazinyl, 4-hydroxypiperidinyl, 1-methylpiperidinyl, 1-ethylpiperidin-4-yl, 1-methylazetidin-3-yl.

In some preferred embodiments, $R^5$ is selected from H, methyl, ethyl, n-propyl, isopropyl, butyl, methoxy, ethoxy, hydroxy, cyclopropyl, cyclobutyl, cyclopentyl, cyclohexyl, morpholinomethyl, hydroxycyclobutyl, hydroxycyclohexyl, cyanoethoxy, cyanomethyl, pyridin-3-yl, 1-methyl-1H-pyrazol-4-yl, 1-methyl-1H-pyrazol-3-yl, 4-methylpiperazin-1-yl, 1-methylpiperidin-4-yl, morpholinyl, pyrrolidin-3-yl, 3-hydroxypyrrolidin-1-yl, and 3-cyanopyrrolidin-1-yl.

In some other preferred embodiments, $R^5$ is selected from ($C_{1-4}$ alkyl) amino or ($C_{1-4}$ alkyl)$_2$ amino (e.g., methylamino, dimethylamino), ($C_{1-4}$ alkyl)pyrazolyl (e.g., 1-methyl-1H-pyrazol-4-yl), ($C_{1-4}$ alkyl)pyrrolidinyl (e.g., 1-methylpyrrolidin-3-yl), ($C_{1-4}$ alkyl)piperidinyl (e.g., 1-methylpiperidin-4-yl, 1-methylpiperidin-3-yl, 1-methylpiperidin-2-yl), pyrrolidinyl or substituted pyrrolidinyl (e.g., pyrrolidin-1-yl, pyrrolidin-3-yl, 3-hydroxypyrrolidin-1-yl, 3-cyanopyrrolidin-1-yl, pyrrolidin-2-yl, 1-methylpyrrolidin-2-yl, 1-(methylsulfonyl)pyrrolidin-3-yl), piperidinyl (e.g., piperidin-2-yl, piperidin-1-yl), halopyrrolidinyl or cyanopyrrolidinyl (e.g., 3-fluoropyrrolidin-1-yl, 3-cyanopyrrolidin-1-yl), azetidinyl (e.g., azetidin-1-yl), haloazetidinyl or hydroxylazetidinyl (e.g., 3-hydroxy-azetidin-1-yl or 3-fluoro-azetidin-1-yl), amino $C_{1-4}$ alkyl (e.g., (dimethylamino)ethyl and (dimethylamino)methyl).

It should be understood that any of the above embodiments of $R^5$ may be combined with any of the embodiments of $R^1$, $R^2$, $R^3$, $R^6$, X, L and n as described above and below in arbitrary combination.

In some embodiments, the compounds described in the present application are compounds selected from formula (II) or formula (III), or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof:

(II)

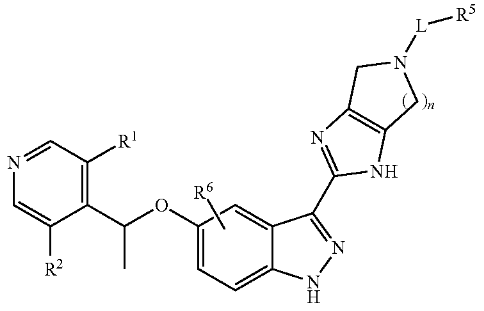

(III)

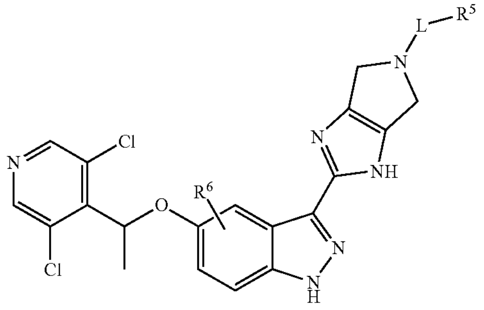

(IV)

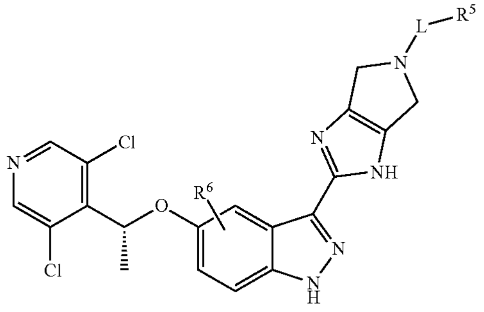

where $R^1$, $R^2$, $R^6$, $R^5$, L and n are all defined as for compounds of formula (I).

The embodiments and preferred options for $R^1$, $R^2$, $R^6$, $R^5$, L and n given above for formula (I) are equally applicable to formula (II), formula (III), and formula (IV).

In some specific embodiments, the compounds of the present application are selected from the compounds shown in the respective examples.

In some embodiments, the compounds according to the present application are selected from:

(2-(5-(1-(3,5-dichloropyridin-4-yl)ethoxy)-1H-indazol-3-yl)-4,6-dihydropyrrolo[3,4-d]imidazol-5(1H)-yl)(4-methylpiperazin-1-yl)ketone;

5-(1-(3,5-dichloropyridin-4-yl)ethoxy)-3-(5-((1-methylpiperidin-4-yl)methyl)-1,4,5,6-tetrahydropyrrolo[3,4-d]imidazol-2-yl)-1H-indazole;

5-(1-(3,5-dichloropyridin-4-yl)ethoxy)-3-(5-(1-methylpiperidin-4-yl)-1,4,5,6-tetrahydropyrrolo[3,4-d]imidazol-2-yl)-1H-indazole;

2-(5-(1-(3,5-dichloropyridin-4-yl)ethoxy)-1H-indazol-3-yl)-5-(1-methylpiperidin-4-yl)-4,5,6,7-tetrahydro-3H-imidazo[4,5-c]pyridine;

(2-(5-(1-(3,5-dichloropyridin-4-yl)ethoxy)-1H-indazol-3-yl)-3,4,6,7-tetrahydro-5H-imidazo[4,5-c]pyridin-5-yl)(4-methylpiperazin-1-yl)ketone;

(2-(5-(1-(3,5-dichloropyridin-4-yl)ethoxy)-1H-indazol-3-yl)-4,6-dihydropyrrolo[3,4-d]imidazol-5(1H)-yl)(1-methylpiperidin-4-yl)ketone;

5-(1-(3,5-dichloropyridin-4-yl)ethoxy)-3-(5-(pyridin-3-ylsulfonyl)-1,4,5,6-tetrahydropyrrolo[3,4-d]imidazol-2-yl)-1H-indazole;

(2-(5-(1-(3,5-dichloropyridin-4-yl)ethoxy)-1H-indazol-3-yl)-4,6-dihydropyrrolo[3,4-d]imidazol-5(1H)-yl)(morpholinyl)ketone;

(2-(5-(1-(3,5-dichloropyridin-4-yl)ethoxy)-1H-indazol-3-yl)-4,6-dihydropyrrolo[3,4-d]imidazol-5(1H)-yl)((R)-pyrrolidin-3-yl)ketone;

(2-(5-(1-(3,5-dichloropyridin-4-yl)ethoxy)-1H-indazol-3-yl)-4,6-dihydropyrrolo[3,4-d]imidazol-5(1H)-yl)((S)-3-hydroxypyrrolidin-1-yl)ketone;

5-(1-(3,5-dichloropyridin-4-yl)ethoxy)-3-(5-methyl-1,4,5,6-tetrahydropyrrolo[3,4-d]imidazol-2-yl)-1H-indazole;

4-(2-(2-(5-(1-(3,5-dichloropyridin-4-yl)ethoxy)-1H-indazol-3-yl)-4,6-dihydropyrrolo[3,4-d]imidazol-5(1H)-yl) ethyl)morpholine;

1-(2-(5-(1-(3,5-dichloropyridin-4-yl)ethoxy)-1H-indazol-3-yl)-4,6-dihydropyrrolo[3,4-d]imidazol-5(1H)-yl)-2-morpholinoethan-1-one;

1-(2-(5-(1-(3,5-dichloropyridin-4-yl)ethoxy)-1H-indazol-3-yl)-4,6-dihydropyrrolo[3,4-d]imidazol-5(1H)-yl)-2-(dimethylamino)ethan-1-one;

2-(2-(5-(1-(3,5-dichloropyridin-4-yl)ethoxy)-1H-indazol-3-yl)-4,6-dihydropyrrolo[3,4-d]imidazol-5(1H)-yl)ethan-1-ol;

5-(1-(3,5-dichloropyridin-4-yl)ethoxy)-3-(5-(methylsulfonyl)-1,4,5,6-tetrahydropyrrolo[3,4-d]imidazol-2-yl)-1H-indazole;

(R)-5-(1-(3,5-dichloropyridin-4-yl)ethoxy)-3-(5-(methylsulfonyl)-1,4,5,6-tetrahydropyrrolo[3,4-d]imidazol-2-yl)-1H-indazole;

Methyl 2-(5-(1-(3,5-dichloropyridin-4-yl)ethoxy)-1H-indazol-3-yl)-4,6-dihydropyrrolo[3,4-d]imidazole-5(1H)-carboxylate;

Methyl (R)-2-(5-(1-(3,5-dichloropyridin-4-yl)ethoxy)-1H-indazol-3-yl)-4,6-dihydropyrrolo [3,4-d]imidazole-5 (1H)-carboxylate;

5-(1-(3,5-dichloropyridin-4-yl)ethoxy)-3-(5-((1-methyl-1H-pyrazol-4-yl)sulfonyl)-1,4,5,6-tetrahydropyrrolo[3,4-d] imidazol-2-yl)-1H-indazole;

5-(1-(3,5-dichloropyridin-4-yl)ethoxy)-3-(1,4,5,6-tetrahydropyrrolo[3,4-d]imidazol-2-yl)-1H-indazole;

5-(1-(3,5-dichloropyridin-4-yl)ethoxy)-3-(5-((1-methyl-1H-pyrazol-3-yl)sulfonyl)-1,4,5,6-tetrahydropyrrolo[3,4-d] imidazol-2-yl)-1H-indazole;

3-(2-(5-(1-(3,5-dichloropyridin-4-yl)ethoxy)-1H-indazol-3-yl)-4,6-dihydropyrrolo[3,4-d]imidazol-5(1H)-yl)cyclobutan-1-ol;

4-(2-(5-(1-(3,5-dichloropyridin-4-yl)ethoxy)-1H-indazol-3-yl)-4, 6-dihydropyrrolo[3,4-d]imidazol-5(1H)-yl)cyclohexan-1-ol;

Ethyl 2-(5-(1-(3,5-dichloropyridin-4-yl)ethoxy)-1H-indazol-3-yl)-4,6-dihydropyrrolo [3,4-d]imidazole-5(1H)-carboxylate;

2-Cyanoethyl 2-(5-(1-(3,5-dichloropyridin-4-yl)ethoxy)-1H-indazol-3-yl)-4,6-dihydropyrrolo[3,4-d]imidazole-5 (1H)-carboxylate;

Cyclopropyl (2-(5-(1-(3,5-dichloropyridin-4-yl)ethoxy)-1H-indazol-3-yl)-4,6-dihydropyrrolo[3,4-d]imidazol-5 (1H)-yl)ketone;

(2-(5-(1-(3,5-dichloropyridin-4-yl)ethoxy)-1H-indazol-3-yl)-4,6-dihydropyrrolo[3,4-d]imidazol-5(1H)-yl)(3-hydroxycyclobutyl)ketone;

3-(2-(5-(5-(1-(3,5-dichloropyridin-4-yl)ethoxy)-1H-indazol-3-yl)-4,6-dihydropyrrolo [3,4-d]imidazol-5(1H)-yl)-3-oxopropane-carbonitrile;

5-(1-(3,5-dichloropyridin-4-yl)ethoxy)-3-(5-(ethylsulfonyl)-1,4,5,6-tetrahydropyrrolo[3,4-d]imidazol-2-yl)-1H-indazole;

3-(5-(cyclopropylsulfonyl)-1,4,5,6-tetrahydropyrrolo[3,4-d] imidazol-2-yl)-5-(1-(3,5-dichloropyridin-4-yl)ethoxy)-1H-indazole;

5-(1-(3,5-dichloropyridin-4-yl)ethoxy)-3-(5-(isopropylsulfonyl)-1,4,5,6-tetrahydropyrrolo[3,4-d]imidazol-2-yl)-1H-indazole;

1-(2-(5-(1-(3,5-dichloropyridin-4-yl)ethoxy)-1H-indazol-3-yl)-4,6-dihydropyrrolo[3,4-d]imidazol-5(1H)-yl)-2-(3-hydroxypyrrolidin-1-yl)ethan-1-one;

1-(2-(2-(5-(1-(3,5-dichloropyridin-4-yl)ethoxy)-1H-indazol-3-yl)-4,6-dihydropyrrolo [3,4-d]imidazol-5(1H)-yl)-2-oxoethyl)pyrrolidine-3-carbonitrile;

(R)-2-(5-(1-(3,5-dichloropyridin-4-yl)ethoxy)-1H-indazol-3-yl)-N-methyl-4,6-dihydropyrrolo[3,4-d]imidazole-5 (1H)-carboxamide;

(R)-2-(5-(1-(3,5-dichloropyridin-4-yl)ethoxy)-1H-indazol-3-yl)-N,N-dimethyl-4,6-dihydropyrrolo[3,4-d]imidazole-5(1H)-carboxamide;

(R)-2-(5-(1-(3,5-dichloropyridin-4-yl)ethoxy)-1H-indazol-3-yl)-N-(1-methyl-1H-pyrazol-4-yl)-4,6-dihydropyrrolo [3,4-d]imidazole-5(1H)-carboxamide;

5-((R)-1-(3,5-dichloropyridin-4-yl)ethoxy)-3-(5-(1-methylpyrrolidin-3-yl)-1,4,5,6-tetrahydropyrrolo[3, 4-d]imidazol-2-yl)-1H-indazole;

5-((R)-1-(3,5-dichloropyridin-4-yl)ethoxy)-3-(5-(1-(1-methylpiperidin-4-yl)ethyl)-1,4,5,6-tetrahydropyrrolo[3, 4-d]imidazol-2-yl)-1H-indazole;

5-((R)-1-(3,5-dichloropyridin-4-yl)ethoxy)-3-(5-(1-methylpiperidin-3-yl)-1,4,5,6-tetrahydropyrrolo[3,4-d]imidazol-2-yl)-1H-indazole;

5-((R)-1-(3,5-dichloropyridin-4-yl)ethoxy)-3-(5-(1-(methylsulfonyl)pyrrolidin-3-yl)-1,4,5,6-tetrahydropyrrolo[3, 4-d]imidazol-2-yl)-1H-indazole;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(pyrrolidin-1-yl)ethan-1-one;

1-(2-(5-((R)-1-(3,5-dichloropyridin-4-yl)ethoxy)-1H-indazol-3-yl)-4,6-dihydropyrrolo[3,4-d]imidazol-5(1H)-yl)-2-((R)-3-hydroxypyrrolidin-1-yl)ethan-1-one;

1-(2-(5-((R)-1-(3,5-dichloropyridin-4-yl)ethoxy)-1H-indazol-3-yl)-4,6-dihydropyrrolo[3,4-d]imidazol-5(1H)-yl)-2-((S)-3-hydroxypyrrolidin-1-yl)ethan-1-one;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(dimethylamino)ethan-1-one;

3-(5-(L-prolyl)-1,4,5,6-tetrahydropyrrolo[3,4-d]imidazol-2-yl)-5-((R)-1-(3,5-dichloropyridin-4-yl)ethoxy)-1H-indazole;

5-((R)-1-(3,5-dichloropyridin-4-yl)ethoxy)-3-(5-(methyl-L-prolyl)-1,4,5,6-tetrahydropyrrolo[3,4-d]imidazol-2-yl)-1H indazole;

(2-(5-((R)-1-(3,5-dichloropyridin-4-yl)ethoxy)-1H-indazol-3-yl)-4,6-dihydropyrrolo[3,4-d]imidazol-5(1H)-yl)((S)-piperidin-2-yl)ketone;

(2-(5-((R)-1-(3,5-dichloropyridin-4-yl)ethoxy)-1H-indazol-3-yl)-4,6-dihydropyrrolo[3,4-d]imidazol-5(1H)-yl)((S)-1-methylpiperidin-2-yl)ketone;

1-(2-(5-((R)-1-(3,5-dichloropyridin-4-yl)ethoxy)-1H-indazol-3-yl)-4,6-dihydropyrrolo[3,4-d]imidazol-5(1H)-yl)-2-(3-fluoropyrrolidin-1-yl)ethan-1-one;

1-(2-(2-(5-((R)-1-(3,5-dichloropyridin-4-yl)ethoxy)-1H-indazol-3-yl)-4,6-dihydropyrrolo[3,4-d]imidazol-5(1H)-yl)-2-oxyethyl)pyrrolidine-3-carbonitrile;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(piperidin-1-yl)ethan-1-one;

(R)-2-(azetidin-1-yl)-1-(2-(5-(1-(3,5-dichloropyridin-4-yl)ethoxy)-1H-indazol-3-yl)-4,6-dihydropyrrolo[3,4-d]imidazol-5(1H)-yl)ethan-1-one;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(3-hydroxyazetidin-1-yl)ethan-1-one;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(3-fluoroazetidin-1-yl)ethan-1-one;

2-(dimethylamino)ethyl (R)-2-(5-(1-(3,5-dichloropyridin-4-yl)ethoxy)-1H-indazol-3-yl)-4,6-dihydropyrrolo[3,4-d]imidazole-5(1H)-carboxylate;

1-methylpyrrolidin-3-yl 2-(5-((R)-1-(3,5-dichloropyridin-4-yl)ethoxy)-1H-indazol-3-yl)-4,6-dihydropyrrolo[3,4-d]imidazole-5(1H)-carboxylate.

The compounds according to the present application can be synthesized via conventional organic synthesis methods according to their specific structures by those skilled in the art.

For example, compounds of formula (I) can be prepared by the method shown in synthetic route (X) below.

Synthetic route (X)

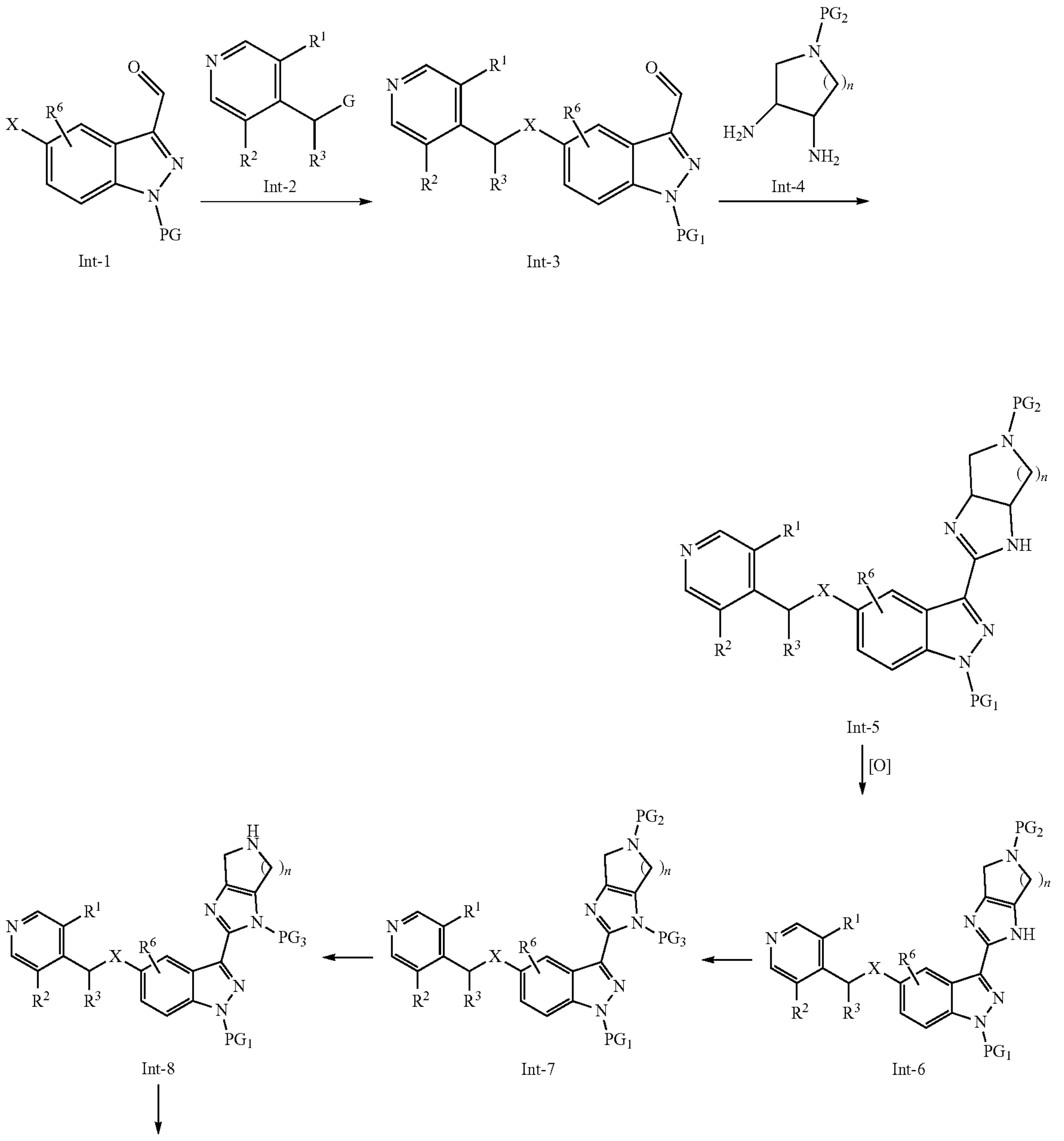

Int-1 Int-3 Int-5 Int-6 Int-7 Int-8

-continued

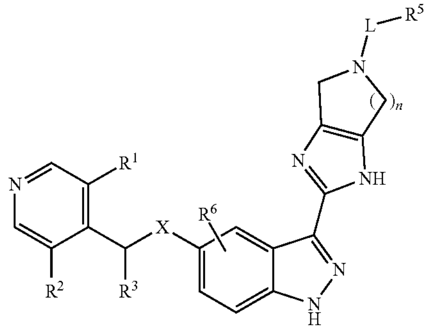

(I)

In the above synthetic route (X), G in an intermediate Int-2 is selected from halogen, hydroxyl, methylsulfonyl (OMs), p-toluenesulfonyl (OTs), and the like. $PG_1$, $PG_2$, and $PG_3$ are an amino protecting group such as tetrahydropyran (THP), benzyl (Bn), p-methoxybenzyl (PMB), SEM, Boc and the like. When G is halogen, OMs, or OTs, the SN2 coupling reaction between intermediates Int-1 and Int-2 under a basic condition can produce an intermediate Int-3. When G is OH, the intermediate Int-3 can be obtained by the Mitsunobu reaction between Int-1 and Int-2. The condensation reaction between intermediate Int-3 and intermediate Int-4 produces a compound Int-5. Under oxidizing conditions (such as, but not limited to, Swern oxidation or IBX oxidation), the Int-5 is converted to an intermediate Int-6. Via a protecting group conversion, the intermediate Int-6 can be converted to an Int-8. Under typical reaction conditions for generating amide (such as, but not limited to, in the presence of DIPEA/HATU), or reaction conditions for generating sulfonamide, or reaction conditions for generating urea, or SN2 coupling reaction conditions, or reaction conditions for generating carbamate, the Int-8 can be reacted with a suitable starting material and then the protecting group is removed to give a target compound of formula (I).

In addition, a person skilled in the art can refer to the synthetic routes of specific compounds shown in Examples of the present application and make appropriate adjustments to the raw materials and reaction conditions to obtain synthesis methods of other compounds.

The compounds according to the present application can inhibit activities of FGFR. For example, the compounds according to the present application can be used to selectively inhibit activities of FGFR1 and/or FGFR2 and/or FGFR3 and/or FGFR4 and/or their mutants (e.g., gatekeeper mutants such as FGFR1 V561M mutant, FGFR2 V564F mutant, FGFR3 V555M mutant, FGFR3 K650E mutant, etc.) in cells or in individuals or patients requiring inhibition of FGFR, which is achieved by administering an inhibitory amount of a compound according to the present application to the cells, individuals or patients.

In some embodiments, the compounds according to the present application have excellent inhibitory activity against FGFR1, FGFR2, FGFR3, and their gatekeeper mutants (e.g., the FGFR1 V561M mutant, the FGFR2 V564F mutant, and the FGFR3 V555M mutant of FGFR).

The term "gatekeeper mutation" as used herein has the meaning commonly known in the art, which is a mutation that prevents drug binding and can lead to the development of drug resistance. The gatekeeper mutants of FGFRs comprise, but not limited to, FGFR1 V561M, FGFR2 V564F, FGFR2 V564I, FGFR2 N550K, FGFR2 V565I, FGFR3 V555M, FGFR4 V550L, FGFR4 V550M, FGFR4 V555M, FGFR4 V555L and others.

In a second aspect, the present application provides a pharmaceutical composition comprising a compound according to the present application, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, as described above, and one or more pharmaceutically acceptable carriers, adjuvants, or excipients.

The pharmaceutical compositions according to the present application can be prepared in a manner well known in the pharmaceutical field and can be administered by a variety of routes, depending on whether topical or systemic treatment is desired and depending on the site to be treated. Administration can be topical (including ophthalmic and to mucous membranes, including intranasal, vaginal, and rectal delivery), pulmonary (e.g., by inhalation or by blowing in a powder or aerosol, including through aerosol dispensers; intratracheal, intranasal, epidermal, and transdermal), ocular, transoral, or parenteral. Methods for ocular delivery may include topical administration (eye drops), subconjunctival, periocular or intravitreal injection or introduction via a balloon catheter or ophthalmic insert surgically placed in the conjunctival sac. Parenteral administration includes intravenous, intra-arterial, subcutaneous, intraperitoneal, or intramuscular injection or infusion; or intracranial (e.g., intrathecal or intracerebroventricular) administration. Parenteral administration can be in the form of a single push dose, or can be, for example, via a continuous perfusion pump. Pharmaceutical compositions and formulations for topical administration may include transdermal patches, ointments, lotions, creams, gels, drops, suppositories, sprays, liquids, and powders.

If a solid carrier is used, the dosage may be tableted, or placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the dosage may be in the form of a syrup, emulsion, paste, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The medicament are prepared by conventional techniques appropriate to the desired preparation containing appropriate amounts of the active ingredient, that is, the compound according to the invention.

Medicament dosage suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate.

The medicament may also contain excipients such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylatedisostearyl alcohols, polyoxyethylene sorbitol and sorbitan esters, microcrystalline cellulose, meta-aluminum hydroxide, bentonite, agar-agar and tragacanth, or mixtures of these substances, and the like.

Dosage forms for topical administration of a compound of the invention include paste, powders, sprays, and inhalants. The active component is admixed under sterile conditions with a physiologically acceptable carrier and any preservatives, buffers, or propellants as may be required.

The amount of the compound according to the present application in the pharmaceutical composition and dosage form can be appropriately determined by those skilled in the art as needed. For example, the compound according to the present application can be present in the pharmaceutical composition or dosage form in a therapeutically effective amount.

In a third aspect, the present application provides use of the compounds according to the present application, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, as described above, or the pharmaceutical composition as described above, in the preparation of drugs for the treatment of diseases or conditions associated with FGFR.

The present application also provides a method of treating diseases or conditions associated with FGFR, said method comprising administering to a patient in need thereof a therapeutically effective amount of a compound according to the present application, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, as described above, or the pharmaceutical composition as described above. Said patient is preferably a mammal, more preferably a human patient. The route of administration may be oral, topical (including, but not limited to, topical application, spraying, and the like), parenteral (including subcutaneous, intramuscular, cortical and intravenous) administration, bronchial administration, or nasal administration, etc.

In some embodiments, said disease or condition associated with FGFR is a cancer. The compound according to the present application may be used, for example, to inhibit proliferation, metastasis, and the like of cancer cells.

Exemplary cancers include bladder cancer, breast cancer, cervical cancer, colorectal cancer, small bowel cancer, colon cancer, rectal cancer, anal cancer, endometrial cancer, head and neck cancer (e.g., cancers of larynx, laryngopharynx, nasopharynx, oropharynx, lips, and mouth), kidney cancer, liver cancer (e.g., hepatocellular carcinoma, bile duct cell carcinoma), lung cancer (e.g., adenocarcinoma, small cell lung cancer, and non-small cell lung cancer, small cell cancer and non-small cell cancer, bronchial cancer, bronchial adenoma, pleural pneumoblastoma), ovarian cancer, prostate cancer, testicular cancer, uterine cancer, esophageal cancer, gallbladder cancer, pancreatic cancer (e.g., exocrine pancreatic cancer), thyroid cancer, parathyroid cancer, skin cancer (e.g., squamous cell carcinoma, Kaposi's sarcoma, Merkel cell skin cancer), and brain cancer (e.g., stellate cell tumor, neural tube embryonal cell tumor, ventricular meningioma, neuroectodermal tumor, pineal gland tumor).

Additional exemplary cancers include hematopoietic malignancies such as leukemia or lymphoma, multiple myeloma, chronic lymphocytic lymphoma, adult T-cell leukemia, B-cell lymphoma, cutaneous T-cell lymphoma, acute myelogenous leukemia, Hodgkin or non-Hodgkin lymphoma, myeloproliferative neoplasms (e.g., true erythroblastosis, primary thrombocythemia, and primary myelofibrosis), Waldenstrom's macroglobulinemia, hairy cell lymphoma, chronic myelogenous lymphoma, acute lymphoblastic lymphoma, AIDS-related lymphoma, and Burkitt's lymphoma.

Additional exemplary cancers include eye tumors, glioblastoma, melanoma, rhabdomyosarcoma, lymphosarcoma, and osteosarcoma.

In some preferred embodiments, said diseases or conditions associated with FGFR are selected from hepatocellular carcinoma, breast cancer, bladder cancer, colorectal cancer, melanoma, mesothelioma, lung cancer, prostate cancer, membrane adenocarcinoma, testicular cancer, thyroid cancer, squamous cell carcinoma, glioblastoma, neuroblastoma, uterine cancer, and rhabdomyosarcoma.

In some other embodiments, said diseases or conditions associated with FGFR are selected from skeletal disorders and chondrocyte disorders, such skeletal disorders and chondrocyte disorders including, but not limited to, chondrodysplasia, hypochondrogenesis, dwarfism, lethal chondrodysplasia (TD) (clinical forms TD I and TD II), Apert syndrome, Crouzon syndrome, Jackson-Weiss syndrome, Beare-Stevenson cutis gyrate syndrome, Pfeiffer syndrome, and cranial suture closure premature syndrome.

In other embodiments, said diseases or conditions associated with FGFR are hypophosphatemic disorder, said hypophosphatemic disorder including, for example, X-linked hypophosphatemic rickets, autosomal recessive hypophosphatemic rickets, autosomal dominant hypophosphatemic rickets, and tumor-induced osteromalacia.

In some other embodiments, said diseases or conditions associated with FGFR are selected from fibrotic diseases. Exemplary fibrotic diseases include cirrhosis, glomerulonephritis, pulmonary fibrosis, systemic fibrosis, rheumatoid arthritis, and wound healing.

In some embodiments, said diseases or conditions associated with FGFR are diseases and conditions that are resistant to FGFR inhibitors that do not target gatekeeper mutatants of FGFR due to gatekeeper mutations in FGFR.

The present application is further described and illustrated below in connection with specific examples.

EXAMPLES

The following examples set forth herein are for illustrative purposes only, to exemplify aspects of the invention and the manner in which they are to be carried out, and are not intended to limit in any way the scope of protection as claimed.

Unless otherwise stated, all reactants were obtained from commercial sources. The instruments and equipment used in the synthesis experiments and product analysis are all conventional instruments and equipment normally used in organic synthesis.

Example 1: (2-(5-(1-(3,5-dichloropyridin-4-yl)ethoxy)-1H-indazol-3-yl)-4,6-dihydropyrrolo[3,4-d]imidazol-5(1H)-yl)(4-methylpiperazin-1-yl)ketone

1

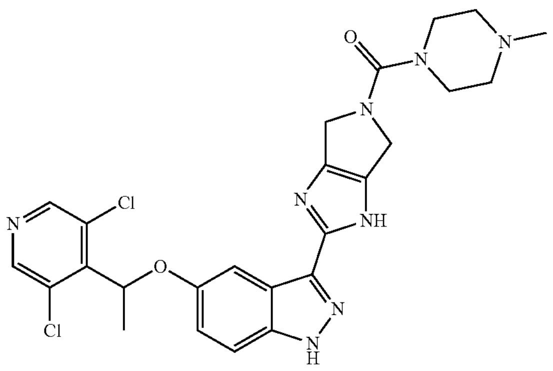

Synthetic Route of Compound 1

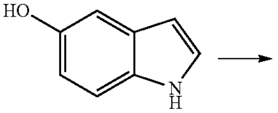

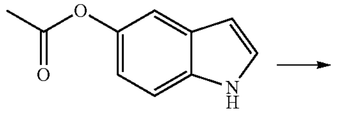

1-1

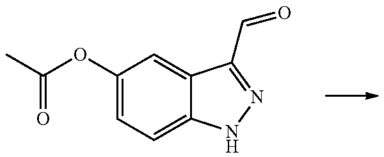

1-2

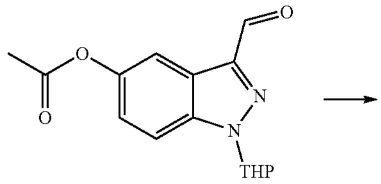

1-3

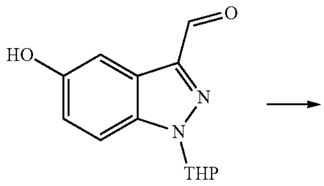

1-4

-continued

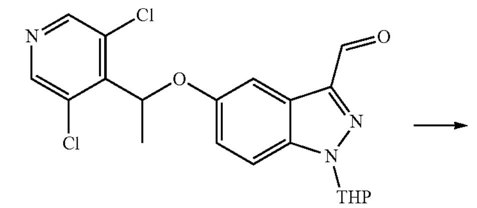

1-5

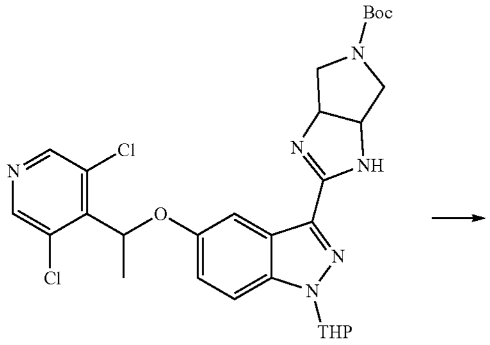

1-6

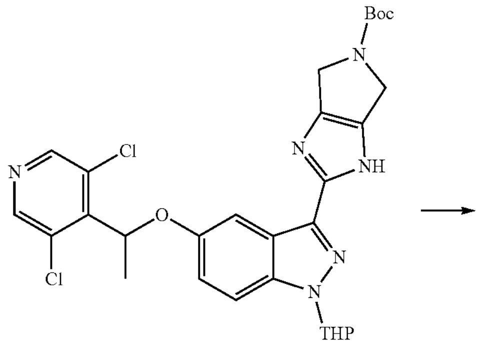

1-7

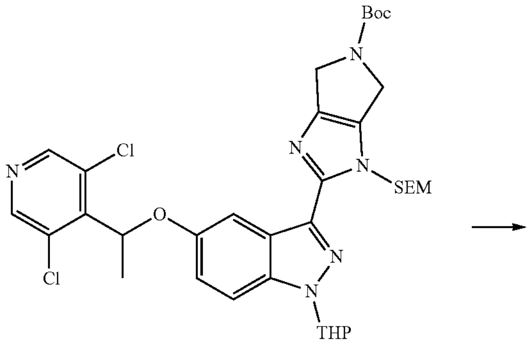

1-8

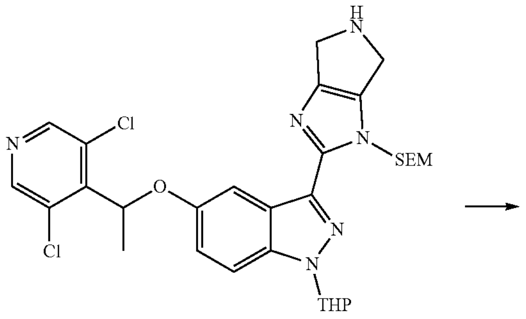

1-9

-continued

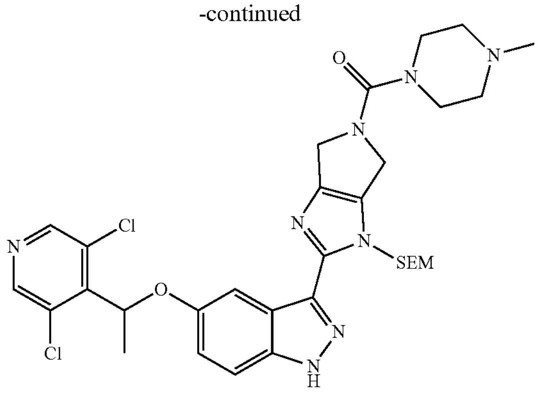

1

Synthesis Method

Synthesis of Intermediate 1-1: 1H-indole-5-acetate 5-hydroxyindole (240.0 mg, 1.80 mmol) was dissolved in 20 ml of pyridine, to which acetic anhydride (202.4 mg, 1.98 mmol) was added dropwise and the resulting mixture was stirred for 16 h at room temperature. Water was added to the reaction solution, and the resulting mixture was extracted twice with ethyl acetate. The resulting organic phases were combined, washed with saturated saline, dried over anhydrous sodium sulfate, and concentrated to afford 276.6 mg of the crude intermediate 1-1 with a yield of 87.4%.

Synthesis of Intermediate 1-2: 3-formyl-1H-indazole-5-acetate

Sodium nitrite (157.5 mg, 2.28 mmol) was dissolved in 10 ml of water, to which 10 ml of DMF was added, and 3M HCl (0.7 ml, 2.05 mmol) was added dropwise at 0 degree. The resulting mixture was stirred for 10 min. To the reaction solution, 1H-indole-5-acetate (50.0 mg, 0.29 mmol) in DMF (10 ml) was added and reacted for 3 h at room temperature. Water was added to the reaction solution, and the resulting mixture was extracted twice with ethyl acetate. The resulting organic phases were combined, washed with saturated saline, dried over anhydrous sodium sulfate, concentrated and purified by silica gel column to give 37.6 mg of Intermediates 1-2 with a yield of 63.5%.

$^1$H NMR (400 MHz, $CDCl_3$) δ 10.25 (s, 1H), 8.01 (s, 1H), 7.49 (d, J=9.0 Hz, 1H), 7.21 (d, J=9.0 Hz, 1H), 2.36 (s, 3H).

Synthesis of Intermediate 1-3: 3-formyl-1-(tetrahydro-2H-pyran-2-yl)-1H-indazole-5-acetate 1-2 (190.0 mg, 0.93 mmol) was dissolved in 20 ml of DCM, to which p-toluenesulfonic acid (177.0 mg, 0.93 mmol) was added, and the mixture was stirred for 2 min. To the reaction solution, 3,4-dihydro-2H-pyran (117.4 mg, 1.40 mmol) in DCM (3 ml) was added and the reaction was carried out at room temperature for 1 h. Water was added to the reaction solution, and the resulting mixture was extracted twice with DCM. The resulting organic phases were combined, washed with saturated sodium bicarbonate solution and saturated saline, dried over anhydrous sodium sulfate, concentrated and purified by silica gel column to give 160.2 mg of Intermediate 1-3 with a yield of 59.6%.

Synthesis of Intermediate 1-4: 5-hydroxy-1-(tetrahydro-2H-pyran-2-yl)-1H-indazole-3-carbaldehyde 1-3 (160.2 mg, 0.56 mmol) was dissolved in 20 ml of methanol, to which potassium carbonate (115.1 mg, 0.83 mmol) was added. The reaction was carried out at room temperature for 30 min. The reaction solution was filtered and the filtrate was concentrated to afford 130.5 mg of crude intermediate 1-4 with a yield of 95.1%.

Synthesis of Intermediate 1-5: 5-(1-(3,5-dichloropyridin-4-yl)ethoxy)-1-(tetrahydro-2H-pyran-2-yl)-1H-indazole-3-carbaldehyde 1-(3,5-dichloropyridin-4-yl)ethan-1-ol (93.6 mg, 0.49 mmol) and triethylamine (148.6 mg, 1.47 mmol) were dissolved in 20 ml DCM, to which methanesulfonyl chloride (57.3 mg, 0.50 mmol) was added dropwise at 0° C. The reaction was carried out for 1 h at room temperature. The reaction solution was quenched with water, and extracted twice with dichloromethane, and the organic phases were combined, washed with saturated saline, dried over anhydrous sodium sulfate and concentrated. The intermediate 1-4 (100.0 mg, 0.41 mmol) and the concentrate were dissolved in 20 ml DMF, to which cesium carbonate (264.6 mg, 0.82 mmol) was added, and the reaction was carried out at 60 degrees for 16 hours. To the reaction solution water was added and the resulting mixture was extracted with ethyl acetate twice. The resulting organic phases were combined, washed with saturated saline, dried over anhydrous sodium sulfate, concentrated and purified by silica gel column to give 64.3 mg of Intermediate 1-5 with a yield of 37.5%.

$^1$H NMR (400 MHz, $CDCl_3$) δ 10.16 (s, 1H), 8.42 (s, 2H), 7.59-7.53 (m, 2H), 7.18-7.15 (m, 1H), 6.11 (q, J=6.7 Hz, 1H), 5.77-5.72 (m, 1H), 4.01-3.94 (m, 1H), 3.77-3.70 (m, 1H), 2.54-2.46 (m, 1H), 2.22-2.06 (m, 2H), 1.81 (d, J=6.7 Hz, 3H), 1.76-1.68 (m, 3H).

Synthesis of Intermediate 1-6: tert-butyl 2-(5-(1-(3,5-dichloropyridin-4-yl)ethoxy)-1-(tetrahydro-2H-pyran-2-yl)-1H-indazol-3-yl)-3a,4,6,6a-tetrahydropyrrolo[3,4-d]imidazole-5(1H)-carboxylate 1-5 (100.0 mg, 0.24 mmol) was dissolved in 10 ml of tert-butanol, to which tert-butyl 3,4-diaminopyrrolidine-1-carboxylate (59.8 mg, 0.24 mmol), iodine (90.6 mg, 0.36 mmol), and potassium carbonate (98.6 mg, 0.71 mmol) were added. The reaction was carried out at 70° C. for 3 hours. After the reaction was completed, the reaction was lowered to room temperature, and quenched by adding 5% aqueous sodium thiosulfate. The resulting mixture was extracted with EA, and the organic phase was washed with saturated saline, dried over anhydrous sodium sulfate, concentrated and purified by silica gel column to give 105 mg of Intermediate 1-6 in a yield of 73.4%.

$^1$H NMR (400 MHz, $CDCl_3$) δ 8.40 (s, 2H), 7.66 (s, 1H), 7.47-7.44 (m, 1H), 7.13-7.10 (m, 1H), 6.11 (q, J=6.8 Hz, 1H), 5.66-5.61 (m, 1H), 4.77-4.48 (m, 2H), 4.02-3.94 (m, 1H), 3.74-3.59 (m, 5H), 2.52-2.43 (m, 1H), 2.04-2.00 (m, 2H), 1.79 (d, J=6.8 Hz, 3H), 1.75-1.68 (m, 3H), 1.45 (s, 9H).

Synthesis of Intermediate 1-7: tert-butyl 2-(5-(1-(3,5-dichloropyridin-4-yl)ethoxy)-1-(tetrahydro-2H-pyran-2-yl)-1H-indazol-3-yl)-4,6-dihydropyrrolo[3,4-d]imidazole-5(1H)-carboxylate 1-6 (40.0 mg, 0.07 mmol) was dissolved in 10 ml DMSO, to which IBX (37.2 mg, 0.13 mmol) was added. The reaction was carried out for 3 h at 50° C. After the reaction was completed, the reaction was lowered to room temperature, and quenched with water. The resulting mixture was extracted with EA, and the organic phase was washed with saturated saline, dried over anhydrous sodium sulfate, concentrated and purified by silica gel column to give Intermediate 1-7 22 mg in a yield of 55.2%.

$^1$H NMR (400 MHz, $CDCl_3$) δ 8.38 (d, J=7.2 Hz, 2H), 7.81 (s, 1H), 7.44-7.41 (m, 1H), 7.15-7.13 (m, 1H), 6.14 (q, J=6.7 Hz, 1H), 5.63-5.60 (m, 1H), 4.57-4.48 (m, 4H), 4.07-3.99 (m, 1H), 3.75-3.69 (m, 1H), 2.55-2.44 (m, 1H), 2.04-1.98 (m, 2H), 1.80 (d, J=6.7 Hz, 3H), 1.76-1.69 (m, 3H), 1.62 (s, 9H).

Synthetic Intermediate 1-8: Tert-butyl 2-(5-(1-(3,5-dichloropyridin-4-yl)ethoxy)-1-(tetrahydro-2H-pyran-2-yl)-1H-indazol-3-yl)-1-((2-(trimethylsilyl)ethoxy) methyl)-4,6-dihydropyrrolo[3,4-d]imidazole-5(1H)-carboxylate 1-7 (22.0 mg, 0.04 mmol) was dissolved in 5 ml THF, and was lowered to 0° C., to which NaH (60%) (1.9 mg, 0.05 mmol) was added. The resulting mixture was stirred for 15 mim, to which SEMCl (6.7 mg, 0.04 mmol) was added. After the addition was complete, the reaction mixture was warmed to room temperature with stirring. After the reaction was complete, the reaction was quenched with water. The resulting mixture was extracted with EA. The organic phase was washed with saturated saline, dried over anhydrous sodium sulfate, concentrated and purified by silica gel column to give Intermediate 1-8 18 mg in a yield of 67.2%.

Synthesis of Intermediate 1-9: 5-(1-(3,5-dichloropyridin-4-yl)ethoxy)-1-(tetrahydro-2H-pyran-2-yl)-3-(1-(((2-(trimethylmethylsilyl)ethoxy)methyl)-1,4,5,6-tetrahydropyrrolo[3,4-d]imidazol-2-yl)-1H-indazole 1-8 (200.0 mg, 0.27 mmol) was dissolved in 20 ml DCM, to which $ZnBr_2$ (246.9 mg, 1.10 mmol) was added. The resulting mixture was stirred at room temperature. After the reaction was completed, the reaction was quenched with water. The resulting mixture was extracted with DCM, and the organic phase was washed with saturated saline, dried over anhydrous sodium sulfate and concentrated to give Intermediates 1-9 140 mg in a yield of 81.1%.

Synthesis of Compound 1: (2-(5-(1-(3,5-dichloropyridin-4-yl)ethoxy)-1H-indazol-3-yl)-4,6-dihydropyrrolo[3,4-d]imidazol-5(1H)-yl)(4-methyl piperazin-1-yl)ketone 1-9 (30.0 mg, 0.05 mmol) and triphosgene (14.1 mg, 0.048 mmol) were dissolved in 5 ml of DCM and was cooled to 0° C., to which TEA (9.6 mg, 0.10 mmol) was added. The reaction was carried out for 1 h. N-methylpiperazine (4.8 mg, 0.05 mmol) was added to the system and warmed to room temperature with stirring. After the reaction was completed, the system was quenched with water. The resulting mixture was extracted with DCM. The organic phases were combined, washed with saturated saline and concentrated. The concentrate was dissolved in 4 ml of methanol, to which 2 ml of concentrated hydrochloric acid was added. The reaction was carried out at 50 degrees for 5 h. The reaction mixture was concentrated, dissolved in 5 ml of methanol, to which 0.5 ml of ammonia was added. The resulting mixture was concentrated, and purified by a preparative plate to obtain the final product of 9.0 mg, in a yield of 34.6%.

$^1$H NMR (400 MHz, MeOD) δ 8.43 (s, 2H), 7.63 (d, J=2.4 Hz, 1H), 7.43 (d, J=9.1 Hz, 1H), 7.16-7.13 (m, 1H), 6.17 (q, J=6.7 Hz, 1H), 4.65 (s, 4H), 3.46 (t, J=5.0 Hz, 4H), 2.64 (t, J=4.0 Hz, 4H), 2.42 (s, 3H), 1.81 (d, J=6.7 Hz, 3H).

Example 2: 5-(1-(3,5-dichloropyridin-4-yl)ethoxy)-3-(5-((1-methyl piperidin-4-yl)methyl)-1,4,5,6-tetrahydropyrrolo[3,4-d]imidazol-2-yl)-1H-indazole

2

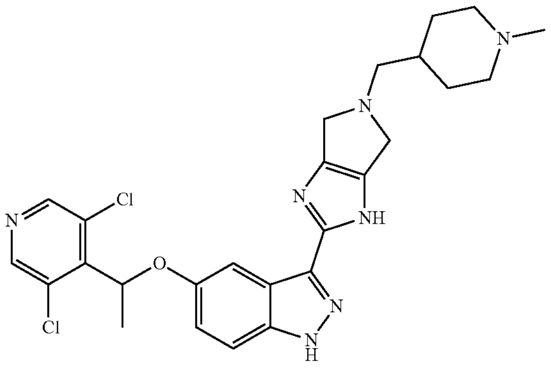

Synthetic Route of Compound 2

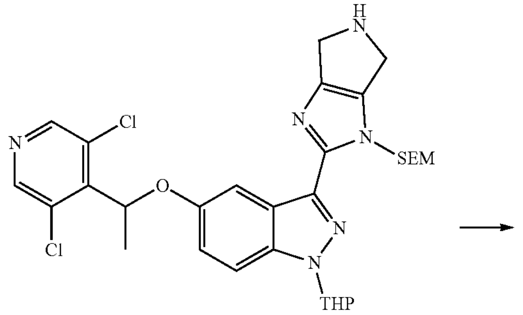

1-9

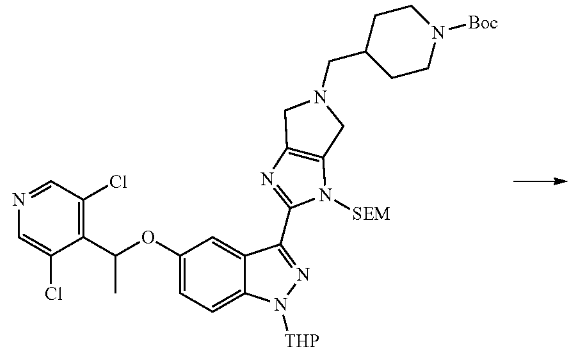

2-1

-continued

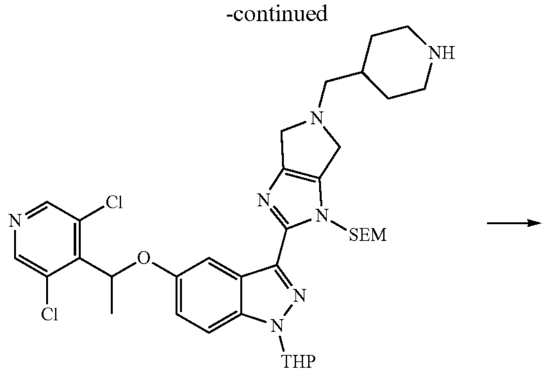

2-2

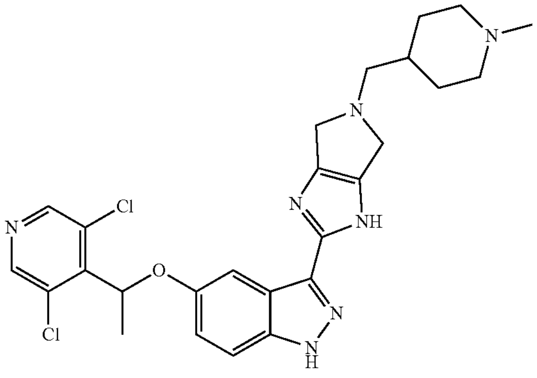

2

Synthesis Method

Synthesis of Intermediate 2-1: tert butyl 4-((2-(5-(5-(1-(3,5-dichloropyridin-4-yl)ethoxy)-1-(tetrahydro-2H-pyran-2-yl)-1H-indazol-3-yl)-1-(((2-(trimethylsilyl) ethoxy) methyl)-4,6-dihydropyrrolo[3,4-d]imidazol-5(1H)-yl)methyl)piperidine-1-carboxylate 1-9 (100.0 mg, 0.16 mmol) and 1-Boc-4-bromomethylpiperidine (53.0 mg, 0.19 mmol) were dissolved in 10 ml DMF, and cesium carbonate (103.5 mg, 0.32 mmol) was added to the system. The reaction was heated to 80 degrees. After the reaction was completed, the reaction was quenched with water. The resulting mixture was extracted with EA, and the organic phases were combined, washed with saturated saline, concentrated and puried by a column chromatography to obtain a product of 63.2 mg, in a yield of 48.1%.

Synthesis of Intermediate 2-2: 5-(1-(3,5-dichloropyridin-4-yl)ethoxy)-3-(5-(piperidin-4-ylmethyl)-1-((2-(trimethylsilyl)ethoxy)methyl)-1,4,5,6-tetrahydropyrrolo[3,4-d]imidazol-2-yl)-1-(tetrahydro-2H-pyran-2-yl)-1H-indazole Intermediate 2-1 (63.0 mg, 0.08 mmol) and zinc bromide (53.0 mg, 0.31 mmol) were dissolved in 10 ml of DCM and the reaction was carried out at room temperature. After the reaction was completed, the reaction was quenched with saturated aqueous sodium bicarbonate. The resulting mixture was extracted with DCM. The organic phases were combined, washed with saturated saline and concentrated to give 42.0 mg, in a yield of 76%.

Synthesis of Compound 2: 5-(1-(3,5-dichloropyridin-4-yl)ethoxy)-3-(5-(1-methylpiperidin-4-yl)-1,4,5,6-tetrahydropyrrolo[3,4-d]imidazol-2-yl)-1H-indazole Intermediate 2-2 (42.0 mg, 0.06 mmol) and 30% aqueous formaldehyde solution (5.0 mg, 0.17 mmol) were dissolved in 5 ml DCM and was cooled to 0° C., to which sodium triacetylborohydride (73.1 mg, 0.35 mmol) was added. After the reaction was completed, it was quenched with water. The resulting mixture was extracted with DCM, and the organic phases were combined, washed with saturated saline and concentrated. The concentrate was dissolved in 4 ml of methanol, to which 2 ml of concentrated hydrochloric acid was added, it was allowed to react at 50 degrees for 5 h, and then concentrated. The concentrate was dissolved in 5 ml of methanol, to which 0.5 ml of ammonia was added, and then the resulting mixture was concentrated, and purified by a preparative plate to obtain the final product of 5.2 mg, in a yield of 17.1%.

$^1$H NMR (400 MHz, MeOD) δ 8.46 (s, 2H), 7.65 (d, J=2.4 Hz, 1H), 7.45 (d, J=9.1 Hz, 1H), 7.18-7.16 (m, 1H), 6.19 (q, J=6.7 Hz, 1H), 4.67-4.56 (m, 4H), 4.14 (d, J=5.7 Hz, 2H), 3.42-3.34 (m, 2H), 2.84-2.76 (m, 2H), 2.78 (s, 3H), 2.04-1.96 (m, 4H), 1.83 (d, J=6.7 Hz, 3H), 1.64-1.58 (m, 1H).

Example 3: 5-(1-(3,5-dichloropyridin-4-yl)ethoxy)-3-(5-(1-methylpiperidin-4-yl)-1,4,5,6-tetrahydropyrrolo[3,4-d]imidazol-2-yl)-1H-indazole

3

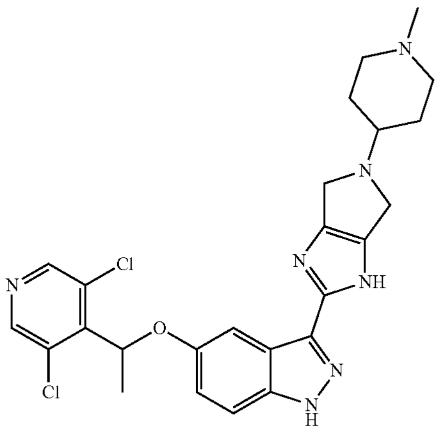

Synthetic Route of Compound 3

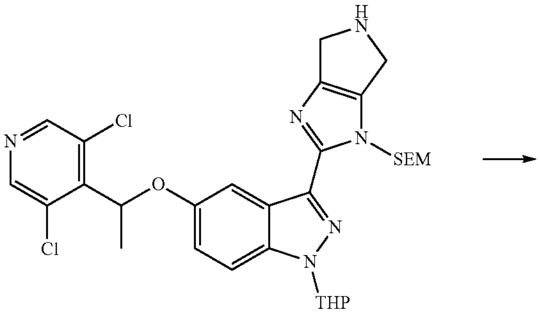

1-9

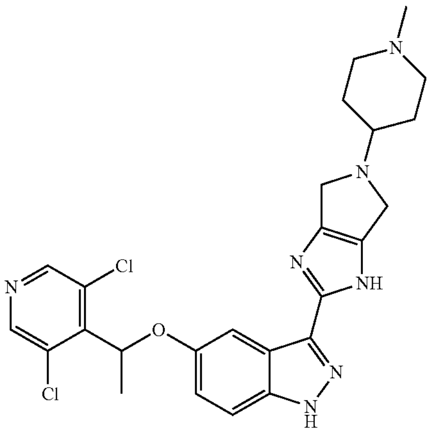

3

Synthesis Method

Synthesis of Compound 3: 5-(1-(3,5-dichloropyridin-4-yl)ethoxy)-3-(5-(1-methylpiperidin-4-yl)-1,4,5,6-tetrahydropyrrolo[3,4-d]imidazol-2-yl)-1H-indazole 1-9 (40.0 mg, 0.06 mmol) and N-methyl-4-piperidone (9.3 mg, 0.08 mmol) were dissolved in 5 ml of 1,2-dichloroethane and cooled to 0° C., to which sodium triacetylborohydride (26.8 mg, 0.13 mmol) was added. After the reaction was completed, it was allowed to quench with water. The resulting mixture was extracted with DCM, and the organic phases were combined, washed with saturated saline and concentrated. The concentrate was dissolved in 4 ml of methanol, to which 2 ml of concentrated hydrochloric acid was added, and it was allowed to react at 50 degrees for 5 h. The reaction mixture was concentrated, the concentrate was dissolved in 5 ml of methanol, to which 0.5 ml of ammonia was added, and then the resulting mixture was concentrated, and purified by preparatio plates to obtain the final product 8.3 mg, in a yield of 25.5%.

$^1$H NMR (400 MHz, MeOD) δ 8.42 (s, 2H), 7.63 (d, J=2.4 Hz, 1H), 7.42 (d, J=9.0 Hz, 1H), 7.15-7.12 (m, 1H), 6.17 (q, J=6.7 Hz, 1H), 3.95 (s, 4H), 3.21-3.11 (m, 2H), 2.84-2.75 (m, 1H), 2.52 (s, 3H), 2.48-2.45 (m, 2H), 2.11-2.08 (m, 2H), 1.80 (d, J=6.7 Hz, 3H), 1.76-1.73 (m, 2H).

Example 4: 2-(5-(1-(3,5-dichloropyridin-4-yl)ethoxy)-1H-indazol-3-yl)-5-(1-methylpiperidin-4-yl)-4,5,6,7-tetrahydro-3H-imidazo[4,5-c]pyridine

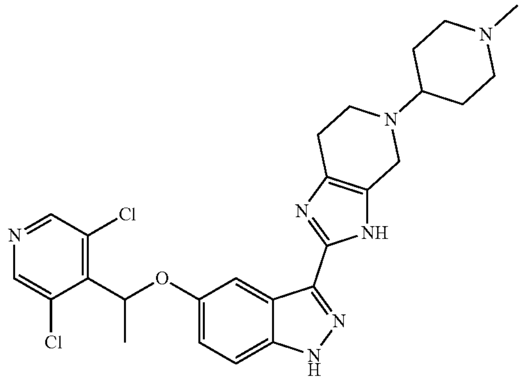

4

Synthetic Route of Compound 4

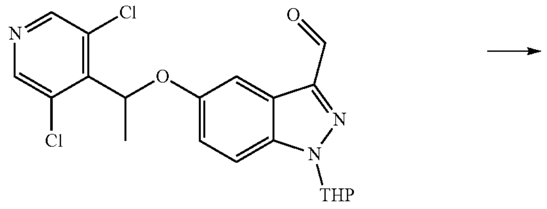

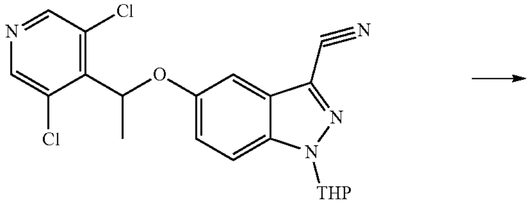

4-1

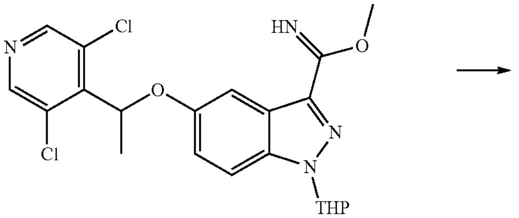

4-2

-continued

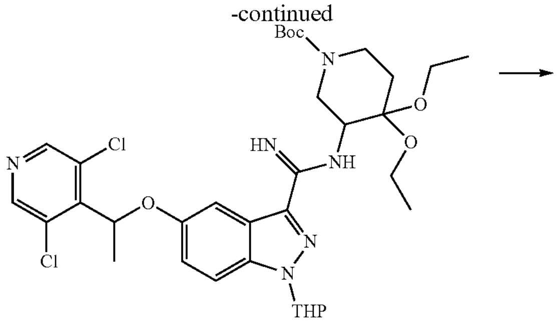

4-3

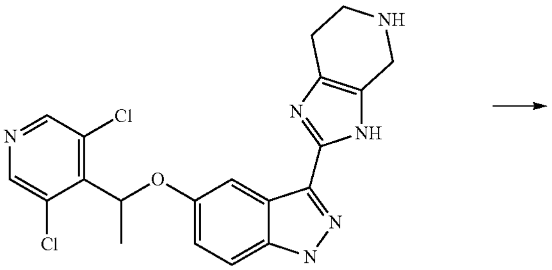

4-4

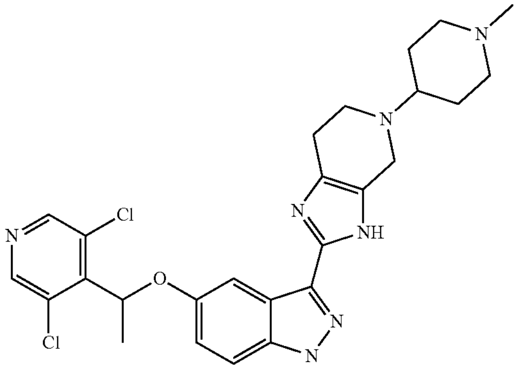

4

Synthesis Method

Synthesis of Intermediate 4-1: 5-(1-(3,5-dichloropyridin-4-yl)ethoxy)-1-(tetrahydro-2H-pyran-2-yl)-1H-indazole-3-carbonitrile 5-(1-(3,5-dichloropyridin-4-yl)ethoxy)-1-(tetrahydro-2H-pyran-2-yl)-1H-indazole-3-carbaldehyde (245.0 mg, 0.58 mmol) and triethylamine (147.5 mg, 1.46 mmol) were dissolved in 10 ml of acetonitrile, to which hydroxylamine hydrochloride (60.8 mg, 0.87 mmol) was added. The reaction was carried out at 60° C. for 3 hours. The reaction solution was cooled to room temperature and triethylamine (471.9 mg, 4.66 mmol) and acetic anhydride (238.0 mg, 2.33 mmol) were added to the reaction solution. It was allowed to react at 80 degrees for 16 hours. To the reaction solution, water was added and the resulting mixture was extracted with dichloromethane twice. The organic phases were combined, washed with saturated saline, dried over anhydrous sodium sulfate, concentrated and purified by silica gel column to give Intermediate 4-1 240.6 mg in a yield of 98.7%.

$^1$H NMR (400 MHz, $CDCl_3$) δ 8.37 (d, J=6.8 Hz, 2H), 7.82 (s, 1H), 7.46 (d, J=9.2 Hz, 1H), 7.15 (d, J=9.2 Hz, 1H), 6.11 (q, J=6.7 Hz, 1H), 5.83-5.79 (m, 1H), 4.01-3.93 (m, 1H), 3.78-3.66 (m, 1H), 2.58-2.44 (m, 2H), 2.18-1.99 (m, 2H), 1.81 (d, J=6.7 Hz, 3H), 1.73-1.65 (m, 2H).

Synthesis of Intermediate 4-2: 5-(1-(3,5-dichloropyridin-4-yl)ethoxy)-1-(tetrahydro-2H-pyran-2-yl)-1H-indazole-3-carbamate Intermediate 4-1 (240.0 mg, 0.58 mmol) was dissolved in 10 ml of methanol and sodium methanol (93.2 mg, 1.73 mmol) was added to the reaction solution. It was allowed to react at room temperature for 16 hours. The reaction solution was concentrated to remove methanol. To the concentrate, water was added and the resulting mixture was extracted twice with ethyl acetate. The organic phases were combined, washed with saturated saline, dried over anhydrous sodium sulfate, and concentrated to obtain Intermediate 4-2 crude product 220 mg in a yield of 85.1%.

$^1$H NMR (400 MHz, $CDCl_3$) δ 8.42 (s, 2H), 7.50-7.47 (m, 1H), 7.22 (s, 1H), 7.14-7.11 (m, 1H), 6.04 (q, J=6.8 Hz, 1H), 5.73-5.64 (m, 1H), 4.02 (s, 3H), 3.99-3.94 (m, 1H), 3.75-3.66 (m, 1H), 2.58-2.46 (m, 1H), 2.18-2.10 (m, 1H), 1.81 (d, J=6.8 Hz, 3H), 1.76-1.63 (m, 4H).

Synthesis of Intermediate 4-3: tert-butyl 3-(5-(1-(3,5-dichloropyridin-4-yl)ethoxy)-1-(tetrahydro-2H-pyran-2-yl)-1H-indazole-3-carboximido)-4,4-diethoxypiperidine-1-carboxylate Intermediate 4-2 (100.0 mg, 0.22 mmol) and tert-butyl 3-amino-4,4-diethoxypiperidine-1-carboxylate (70.6 mg, 0.24 mmol) were dissolved in 10 ml of ethanol, and acetic acid (26.7 mg, 0.44 mmol) was added to the reaction solution. The reaction was carried out at 50 degrees for 16 h. The reaction solution was concentrated to remove ethanol. The residue was dissolved in an appropriate amount of toluene and concentrated to obtain Intermediate 4-3 crude product 211 mg in a yield of 134.4%.

Synthesis of Intermediate 4-4: 2-(5-(1-(3,5-dichloropyridin-4-yl)ethoxy)-1H-indazol-3-yl)-4,5,6,7-tetrahydro-3H-imidazo[4,5-c]pyridine Intermediate 4-3 (157.0 mg, 0.22 mmol) was dissolved in 10 ml of ethanol, 5 ml of concentrated hydrochloric acid was added to the reaction solution. The reaction was carried out at 40 degrees for 16 hours. The reaction mixture was concentrated, dissolved in 5 ml of methanol, to which 0.5 ml of ammonia was added, and then concentrated, and purified on silica gel column to give Intermediate 4-4 60.3 mg, in a yield of 62.8%.

$^1$H NMR (400 MHz, DMSO) δ 13.12 (s, 1H), 12.48 (s, 1H), 8.58 (s, 2H), 7.61 (s, 1H), 7.45 (d, J=9.0 Hz, 1H), 7.09 (dd, J=9.0 Hz, J=2.5 Hz, 1H), 6.01 (q, J=6.5 Hz, 1H), 3.88 (s, 2H), 3.06 (t, J=5.9 Hz, 2H), 2.79 (t, J=5.5 Hz, 2H), 1.75 (d, J=6.6 Hz, 3H).

Synthesis of Compound 4: 2-(5-(1-(3,5-dichloropyridin-4-yl)ethoxy)-1H-indazol-3-yl)-5-(1-methylpiperidin-4-yl)-4,5,6,7-tetrahydro-3H-imidazo[4,5-c]pyridine Intermediate 4-4 (10.0 mg, 0.02 mmol) was dissolved in 5 ml NMP, to which 0.1 ml acetic acid was added, it was allowed to stir at 55 degrees for 10 min. The reaction mixture was cooled to room temperature, and 1-methylpiperidin-4-one (4.0 mg, 0.03 mmol) was added. It was allowed to react at room temperature for 16 h. Sodium triacetoxyborohydride (7.4 mg, 0.03 mmol) was added. It was allowed to react at room temperature for 2 h and the pH was adjusted by adding 0.5 ml of ammonia, to which water was added. The resulting mixture was extracted twice with ethyl acetate, and the organic phases was combined, washed with saturated saline, dried over anhydrous sodium sulfate, concentrated, and purified by preparation plate to obtain the final product of 3.6 mg in yield of 29.3%.

$^1$H NMR (400 MHz, MeOD) δ 8.45 (s, 2H), 7.61 (s, 1H), 7.43 (d, J=9.0 Hz, 1H), 7.15 (dd, J=9.1, J=2.4 Hz, 1H), 6.18 (q, J=6.7 Hz, 1H), 3.81 (s, 2H), 3.12 (d, J=12.1 Hz, 2H), 3.03 (t, J=5.7 Hz, 2H), 2.83 (t, J=5.8 Hz, 2H), 2.75-2.69 (m, 1H), 2.42 (s, 3H), 2.30 (t, J=12.1 Hz, 2H), 2.07 (d, J=12.5 Hz, 2H), 1.84-1.76 (m, 5H).

Example 5: (2-(5-(1-(3,5-dichloropyridin-4-yl)ethoxy)-1H-indazol-3-yl)-3,4,6,7-tetrahydro-5H-imidazo[4,5-c]pyridin-5-yl)(4-methylpiperazin-1-yl)ketone

5

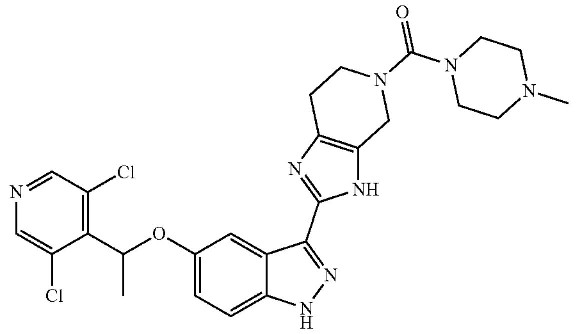

Synthetic Route of Compound 5

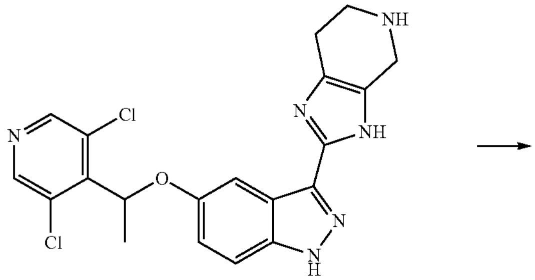

4-4

-continued

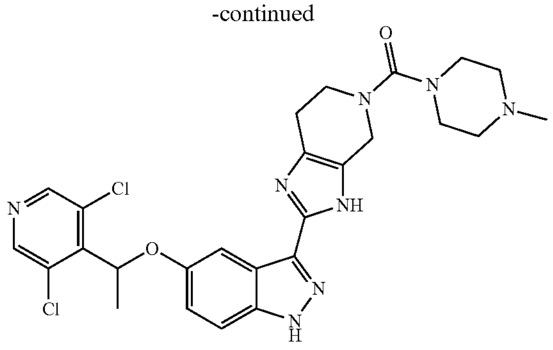

5

Synthesis Method

Synthesis of Compound 5: (2-(5-(1-(3,5-dichloropyridin-4-yl)ethoxy)-1H-indazol-3-yl)-3,4,6,7-tetrahydro-5H-imidazo[4,5-c]pyridin-5-yl)(4-methylpiperazin-1-yl) ketone Triphosgene (13.8 mg, 0.05 mmol) was dissolved in 5 ml of anhydrous dichloromethane and a solution of Intermediate 4-4 (20.0 mg, 0.05 mmol) in dichloromethane (2 ml) was added dropwise at 0 degree, followed by slow dropwise addition of anhydrous triethylamine (138.3 mg, 0.47 mmol) at room temperature for 10 min with stirring. It was monitored by TLC for disappearance of the material. 1-methyl piperazine (7.0 mg, 0.07 mmol) in dichloromethane (2 ml) was added, which was stirred for 2 h at room temperature. The reaction was quenched with water. The resulting mixture was extracted twice with dichloromethane, and the organic phases were combined, washed with saturated saline, dried over anhydrous sodium sulfate, concentrated, and purified on silica gel column to give the final product of 10.3 mg in a yield of 38.6%.

$^1$H NMR (400 MHz, MeOH) δ 8.43 (s, 2H), 7.60 (d, J=2.3 Hz, 1H), 7.41 (d, J=9.1 Hz, 1H), 7.13 (dd, J=9.1, J=2.4 Hz, 1H), 6.16 (q, J=6.7 Hz, 1H), 4.44 (s, 2H), 3.64 (t, J=5.7 Hz, 2H), 3.40 (t, J=4.9 Hz, 4H), 2.84 (t, J=5.7 Hz, 2H), 2.58 (t, J=4.9 Hz, 4H), 2.38 (s, 3H), 1.81 (d, J=6.7 Hz, 3H).

Example 6: (2-(5-(1-(3,5-dichloropyridin-4-yl)ethoxy)-1H-indazol-3-yl)-4,6-dihydropyrrolo[3,4-d]imidazol-5(1H)-yl)(1-methylpiperidin-4-yl)ketone

6

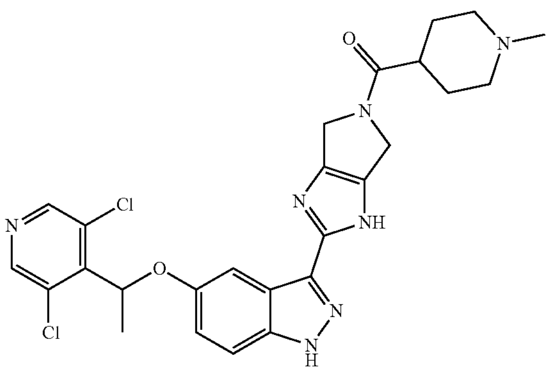

Synthetic Route of Compound 6

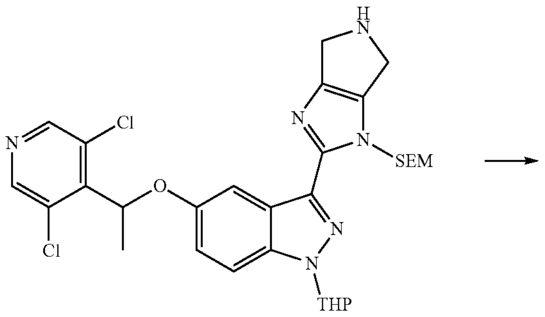

1-9

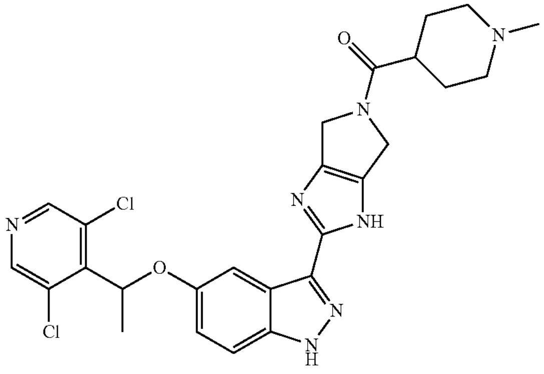

6

Synthesis Method

Synthesis of Compound 6: (2-(5-(1-(3,5-dichloropyridin-4-yl)ethoxy)-1H-indazol-3-yl)-4,6-dihydropyrrolo[3,4-d]imidazol-5(1H)-yl)(1-methylpiperidin-4-yl)ketone 1-9 (30.0 mg, 0.05 mmol), 1-methylpiperidine-4-carboxylic acid (8.2 mg, 0.06 mmol) and HATU (21.7 mg, 0.06 mmol) were dissolved in 5 ml DMF, to which DIPEA (9.2 mg, 0.07 mmol) was added dropwise. The resulting mixture was stirred at room temperature for 3 h. Water was added to the reaction solution and the resulting mixture was extracted twice with ethyl acetate. The organic phases were combined, washed with saturated saline, dried over anhydrous sodium sulfate, and concentrated. The concentrate was dissolved in 6 ml of methanol, to which 3 ml of concentrated hydrochloric acid was added. It was allowed to react at 50 degrees for 6 h. The reaction mixture was concentrated, dissolved in 5 ml of methanol, to which 0.5 ml of ammonia was added, further concentrated, and purified by a preparative plate to obtain the final product of 6.2 mg, in a yield of 24.1%.

$^1$H NMR (400 MHz, MeOH) δ 8.46 (s, 2H), 7.66 (d, J=2.3 Hz, 1H), 7.45 (d, J=9.0 Hz, 1H), 7.17 (dd, J=9.1, J=2.4 Hz, 1H), 6.19 (q, J=6.6 Hz, 1H), 4.84 (s, 2H), 4.62 (s, 2H), 3.11-3.07 (m, 2H), 2.75-2.65 (m, 1H), 2.41 (s, 3H), 2.35-2.27 (m, 2H), 1.98-1.90 (m, 4H), 1.83 (d, J=6.7 Hz, 3H).

Example 7: 5-(1-(3,5-dichloropyridin-4-yl)ethoxy)-3-(5-(pyridin-3-ylsulfonyl)-1,4,5,6-tetrahydropyrrolo[3,4-d]imidazol-2-yl)-1H-indazole

7

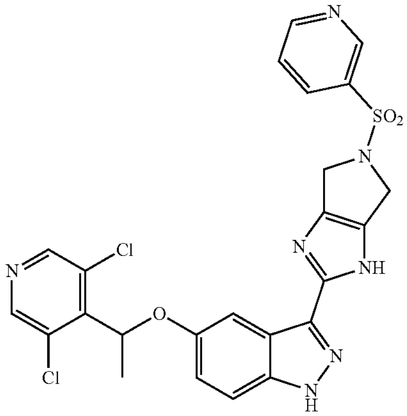

Synthetic Route of Compound 7

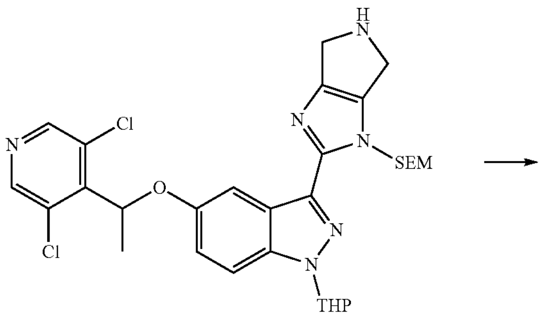

1-9

-continued

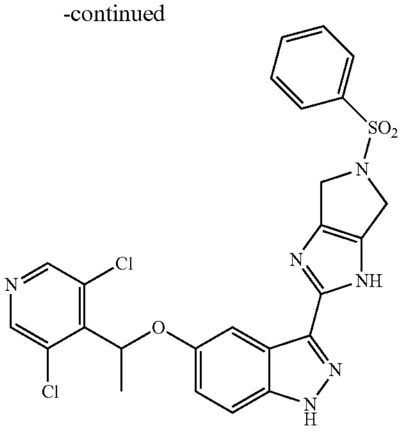

7

Synthesis Method

Synthesis of Compound 7: 5-(1-(3,5-dichloropyridin-4-yl)ethoxy)-3-(5-(pyridin-3-ylsulfonyl)-1,4,5,6-tetrahydropyrrolo[3,4-d]imidazol-2-yl)-1H-indazole 1-9 (30.0 mg, 0.05 mmol), and TEA (15.2 mg, 0.15 mmol) were dissolved in 5 ml DCM, and 3-sulfonylpyridine (13.3 mg, 0.08 mmol) was added dropwise at 0° C. The resulting mixture was stirred for half an hour. Water was added to the reaction solution. The resulting mixture was extracted twice with dichloromethane, and the organic phases were combined, washed with saturated saline, dried over anhydrous sodium sulfate, and concentrated. The concentrate was dissolved in 6 ml of methanol, to which 3 ml of concentrated hydrochloric acid was added. It was allowed to react for 3 h at 50° C. The resulting mixture was concentrated, dissolved in 5 ml of methanol, to which 0.5 ml of ammonia was added, then further concentrated, and puried by a preparative plate to obtain the final product 10.2 mg, in a yield of 37.7%. LC-MS m/z (ESI) of $[M+H]^+$ for $C_{24}H_{20}C_{l2}N_7O_3S$ calculated as: 556.1 and measured as: 556.1.

Example 8: (2-(5-(1-(3,5-dichloropyridin-4-yl)ethoxy)-1H-indazol-3-yl)-4,6-dihydropyrrolo[3,4-d]imidazol-5(1H)-yl)(morpholinyl)ketone

8

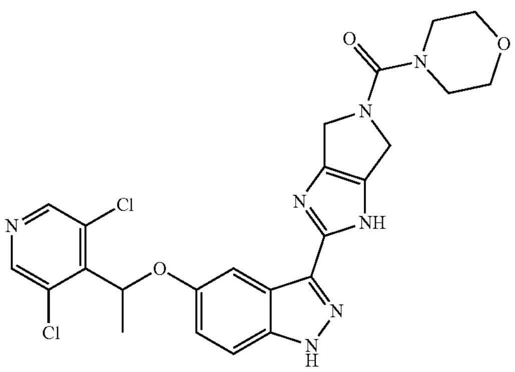

Synthetic Route of Compound 8

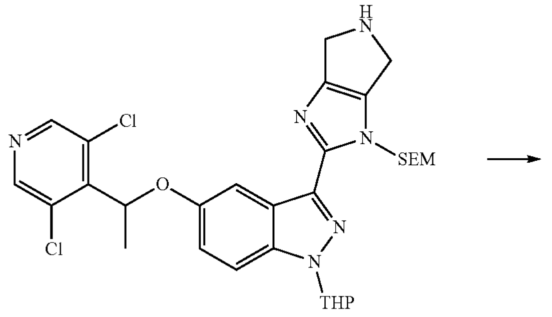

1-9

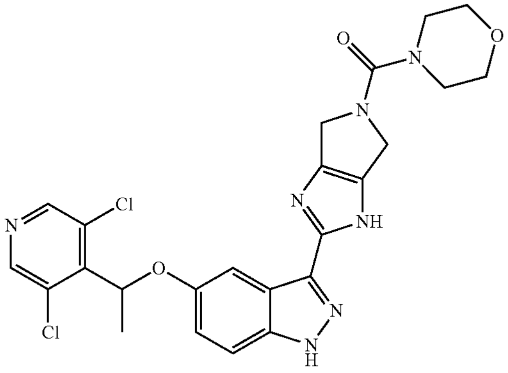

8

Synthesis Method

Synthesis of compound 8: (2-(5-(1-(3,5-dichloropyridin-4-yl)ethoxy)-1H-indazol-3-yl)-4,6-dihydropyrrolo[3,4-d]imidazol-5(1H)-yl)(morpholinyl)ketone 1-9 (46.0 mg, 0.07 mmol) was dissolved in 10 ml of dichloromethane, to which triphosgene (21.7 mg, 0.07 mmol) was added. The system was cooled to 0° C., and triethylamine (14.8 mg, 0.15 mmol) was added dropwise. It was allowed to react for 0.5 h. To the system, morpholine (6.37 mg, 0.07 mmol) was added and then it was warmed to room temperature. After the reaction was completed, it was quenched with water. The resulting mixture was extracted with DCM, and the organic phase were combined, washed with saturated saline and concentrated. The concentrate was dissolved in 4 ml of methanol, to which 2 ml of concentrated hydrochloric acid was added. It was allowed to react at 50 degrees for 5 h. The reaction mixture was concentrated, dissolved in 5 ml of methanol, to which 0.5 ml of ammonia was added, further concentrated, and purified by a preparative plate to obtain the final product of 10.2 mg, in a yield of 26.4%.

$^1$H NMR (400 MHz, DMSO) δ 13.10 (s, 1H), 12.56 (s, 1H), 8.57 (s, 2H), 7.68 (d, J=2.4 Hz, 1H), 7.46 (d, J=9.0 Hz, 1H), 7.11-7.08 (m, 1H), 6.04 (q, J=6.6 Hz, 1H), 4.58-4.51 (m, 4H), 3.66-3.64 (m, 4H), 3.31-3.26 (m, 4H), 1.76 (d, J=6.7 Hz, 3H).

Example 9: (2-(5-(1-(3,5-dichloropyridin-4-yl)ethoxy)-1H-indazol-3-yl)-4,6-dihydropyrrolo[3,4-d]imidazol-5(1H)-yl)((R)-pyrrolidin-3-yl)ketone

9

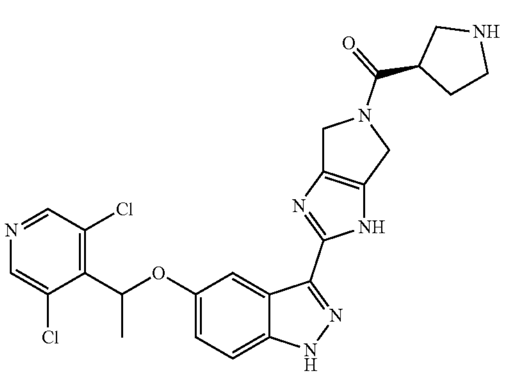

Synthetic Route of Compound 9

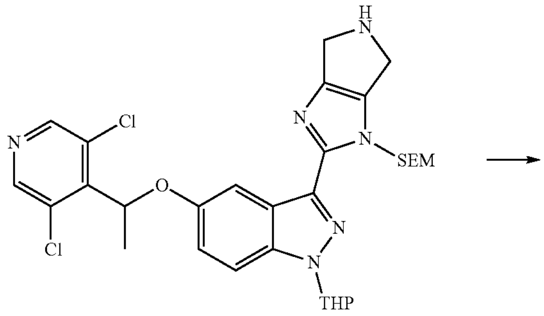

1-9

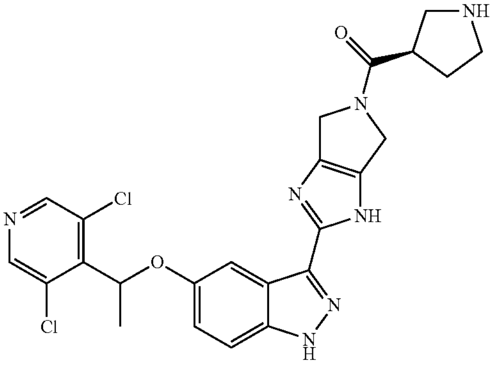

9

Synthesis Method

Synthesis of Compound 9: (2-(5-(1-(3,5-dichloropyridin-4-yl)ethoxy)-1H-indazol-3-yl)-4,6-dihydropyrrolo[3,4-d]imidazol-5(1H)-yl)((R)-pyrrolidin-3-yl)ketone 1-9 (40.0 mg, 0.06 mmol) was dissolved in 10 ml of DMF, to which (R)-1-BOC-pyrrolidine-3-carboxylic acid (13.8 mg, 0.06 mmol), HATU (24.3 mg, 0.06 mmol) was added and DIPEA (9.9 mg, 0.08 mmol) was added dropwise. The reaction was carried out at room temperature. After the reaction was completed, it was quenched with water. The resulting mixture was extracted with EA, and the organic phases were combined, washed with saturated saline and concentrated. The concentrate was dissolved in 4 ml of methanol, to which 2 ml of concentrated hydrochloric acid was added. It was allowed to react at 50 degrees for 5 h. The reaction mixture was concentrated, dissolved in 5 ml of methanol, to which 0.5 ml of ammonia was added, further concentrated, and purified by a preparative plate to obtain the final product of 11.2 mg, in a yield of 34.2%.

$^1$H NMR (400 MHz, MeOD) δ 8.46 (s, 2H), 7.66 (d, J=2.4 Hz, 1H), 7.46 (d, J=9.0 Hz, 1H), 7.19-7.16 (m, 1H), 6.19 (q, J=6.7 Hz, 1H), 4.80-4.59 (m, 4H), 3.71-3.66 (m, 2H), 3.50-3.43 (m, 3H), 2.06-2.04 (m, 2H), 1.84 (d, J=6.7 Hz, 3H).

Example 10: (2-(5-(1-(3,5-dichloropyridin-4-yl)ethoxy)-1H-indazol-3-yl)-4,6-dihydropyrrolo[3,4-d]imidazol-5(1H)-yl)((S)-3-hydroxypyrrolidin-1-yl)ketone

10

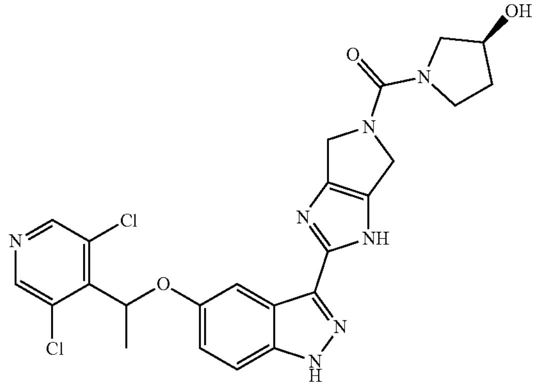

Synthetic Route of Compound 10

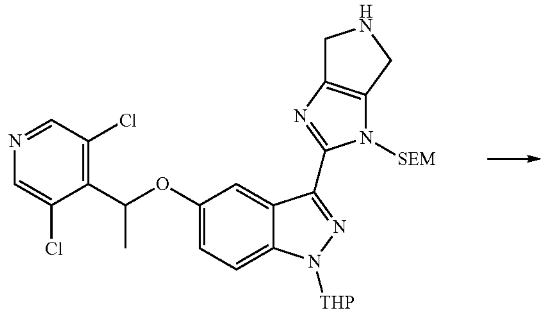

1-9

-continued

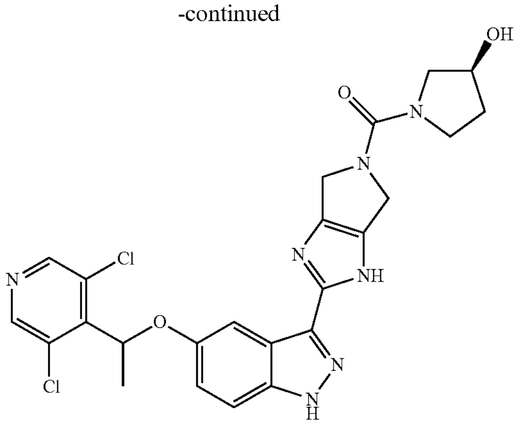

10

Synthesis Method

Synthesis of Compound 10: (2-(5-(1-(3,5-dichloropyridin-4-yl)ethoxy)-1H-indazol-3-yl)-4,6-dihydropyrrolo[3,4-d]imidazol-5(1H)-yl)((S)-3-hydroxypyrrolidin-1-yl)ketone Triphosgene (14.1 mg, 0.05 mmol) was dissolved in 5 ml of anhydrous dichloromethane, to which a solution of Intermediate 1-9 (30.0 mg, 0.05 mmol) in dichloromethane (2 ml) was added dropwise at 0 degree, followed by slow dropwise addition of anhydrous triethylamine (48.2 mg, 0.47 mmol). The mixture was stirred at room temperature for 10 min and it was monitored by TLC for disappearance of the material. A solution of (S)-Pyrrolidine-3-ol (6.2 mg, 0.07 mmol) in dichloromethane (2 ml) was added, the mixture was stirred at room temperature for 2 h. The reaction was quenched with water. The resulting mixture was extracted twice with dichloromethane, and the organic phases were combined, washed with saturated saline, dried over anhydrous sodium sulfate, and concentrated. The concentrate was dissolved in 6 ml methanol, to which 3 ml concentrated hydrochloric acid was added, and it was allowed to react at 50 degrees for 6 h. The reaction mixture was concentrated, dissolved in 5 ml methanol, to which 0.5 ml of ammonia was added, further concentrated, and purified by a preparative plate, to obtain the final product of 6.5 mg, in a yield of 25.8%.

$^1$H NMR (400 MHz, MeOH) δ 8.43 (d, J=1.4 Hz, 2H), 7.64 (d, J=2.4 Hz, 1H), 7.42 (d, J=9.1 Hz, 1H), 7.14 (dd, J=9.0, J=2.4 Hz, 1H), 6.17 (q, J=6.6 Hz, 1H), 4.79-4.76 (m, 2H), 4.57-4.54 (m, 2H), 4.44-4.42 (m, 1H), 3.77-3.67 (m, 2H), 3.60-3.55 (m, 1H), 3.44-3.41 (m, 1H), 2.07-1.92 (m, 2H), 1.81 (d, J=6.7 Hz, 3H).

Example 11: 5-(1-(3, 5-dichloropyridin-4-yl) ethoxy)-3-(5-methyl-1,4,5,6-tetrahydropyrrolo[3,4-d]imidazol-2-yl)-1H-indazole

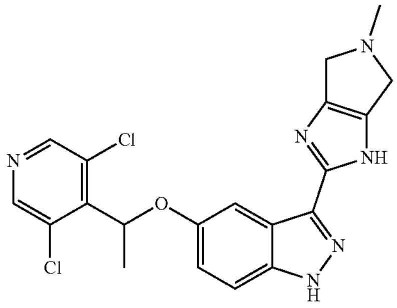

11

Synthetic Route of Compound 11

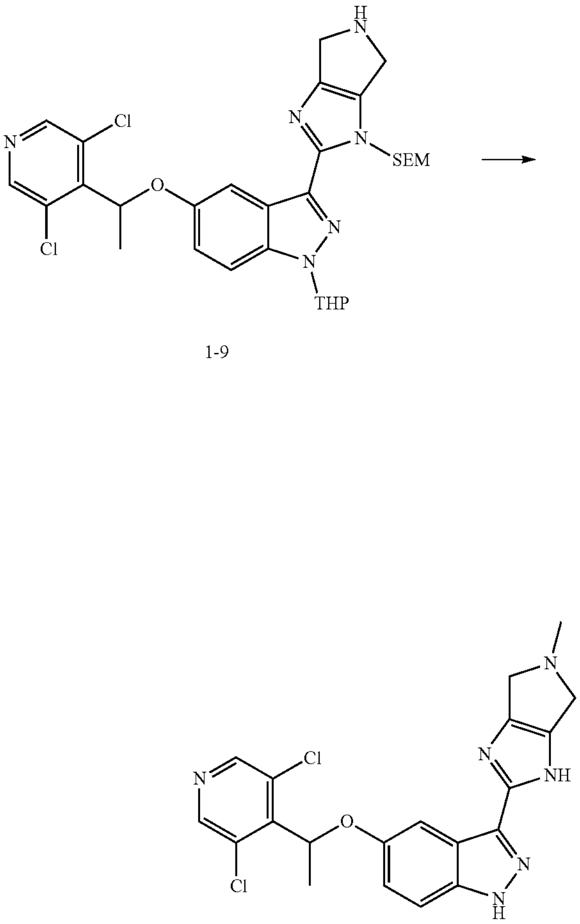

1-9

11

Synthesis Method

Synthesis of Compound 11: 5-(1-(3, 5-dichloropyridin-4-yl)ethoxy)-3-(5-methyl-1,4,5,6-tetrahydropyrrolo[3,4-d]imidazol-2-yl)-1H-indazole Intermediate 1-9 (30.0 mg, 0.05 mmol) was dissolved in 5 ml of dichloromethane, to which aqueous formaldehyde (0.01 ml, 0.14 mmol) was added. The reaction mixture was stirred for 20 min at room temperature. Sodium triacetylborohydride (60.8 mg, 0.29 mmol) was added. It was allowed to react for 2 h at room temperature. Water was added to the reaction solution, the resulting mixture was extracted twice with dichloromethane, and the organic phases were combined, washed with saturated saline, and dried over sodium sulfate. The concentroated crude product was dissolved in 2 ml of methanol and 1 ml of concentrated hydrochloric acid, it was allowed to react at 50 degrees for 6 h. The reaction mixture was concentrated, dissolved in 3 ml of methanol, to which 0.5 ml of ammonia was added, further concentrated, and purified by a preparative plate to obtain the final product of 3.6 mg in a total yield of 17.6% in two steps.

$^1$H NMR (400 MHz, MeOD) δ 8.44 (s, 2H), 7.64 (d, J=4.0 Hz, 1H), 7.45 (d, J=12.0 Hz, 1H), 7.16 (dd, J=4.0 Hz, J=8.0 Hz, 1H), 6.20 (dd, J=8.0 Hz, J=16.0 Hz, 1H), 3.96 (s, 4H), 2.75 (s, 3H), 1.83 (d, J=4.0 Hz, 3H).

Example 12: 4-(2-(2-(2-(5-(1-(3,5-dichloropyridin-4-yl)ethoxy)-1H-indazol-3-yl)-4,6-dihydropyrrolo[3,4-d]imidazol-5(1H)-yl)ethyl)morpholine

12

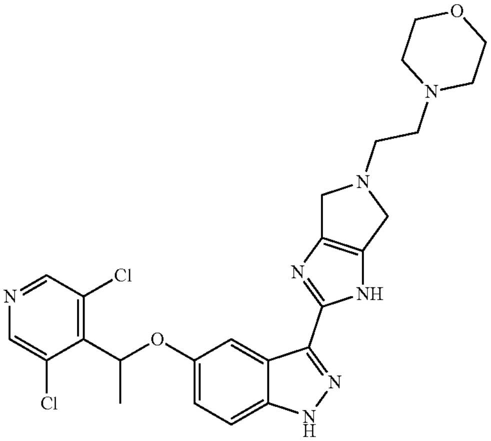

Synthetic Route of Compound 12

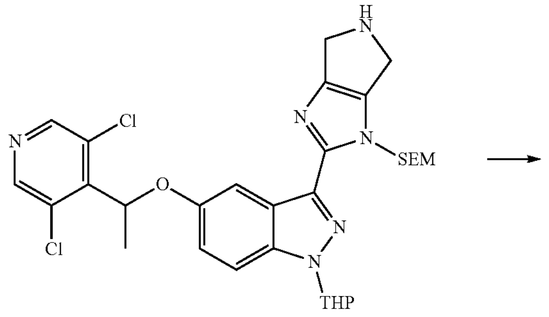

1-9

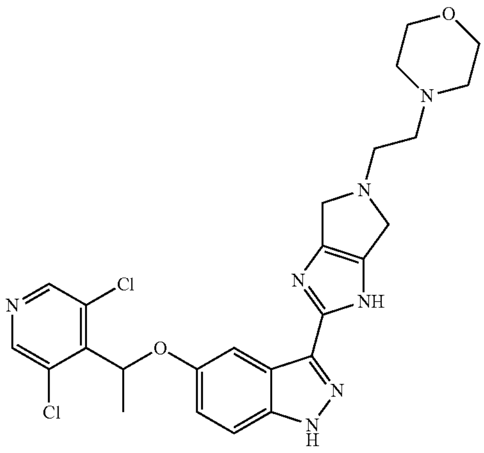

12

Synthesis Method

Synthesis of Compound 12: 4-(2-(2-(2-(5-(1-(3,5-dichloropyridin-4-yl)ethoxy)-1H-indazol-3-yl)-4,6-dihydropyrrolo[3,4-d]imidazole-5(1H)-yl)ethyl) morpholine 1-9 (100.0 mg, 0.16 mmol) and 4-(2-bromoethyl)morpholine hydrobromide (52.4 mg, 0.19 mmol) were dissolved in 10 ml of anhydrous DMF, and cesium carbonate (103.5 mg, 0.32 mmol) was added to the system and the resulting mixture was stirred at 100 degrees for 3 h. After the reaction was completed, water was added and the resulting mixture was extracted twice with ethyl acetate, and the organic phases were combined and washed with saturated saline, dried with anhydrous sodium sulfate, and concentrated. The concentrate was dissolved in 4 ml of methanol, to which 2 ml of concentrated hydrochloric acid was added. It was allowed to react at 50 degrees for 6 h. The reaction mixture was concentrated, dissolved in 5 ml of methanol, to which 0.5 ml of ammonia was added, further concentrated, and purified by a preparative plate to obtain the final product of 4.5 mg in a yield of 5.3%.

$^1$H NMR (400 MHz, MeOH) δ 8.43 (d, J=1.4 Hz, 2H), 7.64 (d, J=2.4 Hz, 1H), 7.44 (d, J=9.1 Hz, 1H), 7.15 (dd, J=9.0, J=2.4 Hz, 1H), 6.19 (q, J=6.6 Hz, 1H), 4.04 (s, 4H), 3.76 (t, J=4.7 Hz, 4H), 3.18-3.10 (m, 2H), 2.71-2.67 (m, 2H), 2.62-2.60 (m, 4H), 1.83 (d, J=6.6 Hz, 3H).

Example 13: 1-(2-(5-(1-(3,5-dichloropyridin-4-yl) ethoxy)-1H-indazol-3-yl)-4,6-dihydropyrrolo[3,4-d] imidazol-5(1H)-yl)-2-morpholinoethan-1-one

13

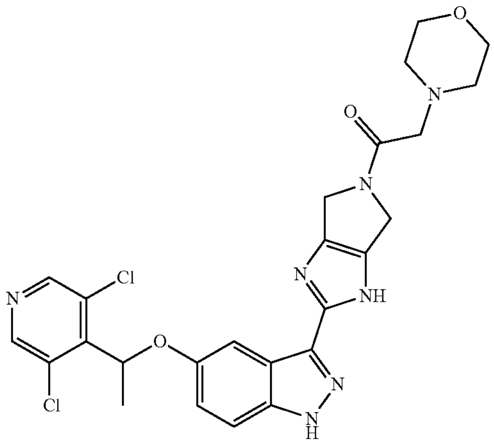

Synthetic Route of Compound 13

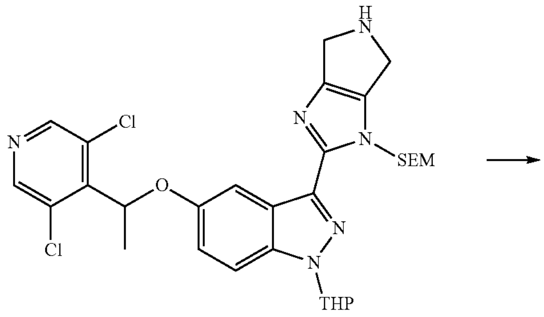

1-9

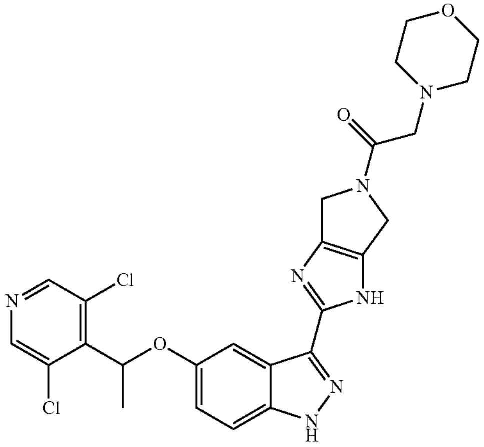

13

Synthesis Method

Synthesis of Compound 13: 1-(2-(5-(1-(3,5-dichloropyridin-4-yl)ethoxy)-1H-indazol-3-yl)-4,6-dihydropyrrolo[3,4-d]imidazol-5(1H)-yl)-2-morpholinoethan-1-one 1-9 (30.0 mg, 0.05 mmol) was dissolved in 10 ml of DMF and 4-morpholineacetic acid (6.9 mg, 0.05 mmol), HATU (21.7 mg, 0.06 mmol) and DIPEA (12.3 mg, 0.10 mmol) were added to the system and it was allowed to react for 2 h at room temperature. The reaction was quenched with water, the resulting mixture was extracted with EA, and the organic phases were combined, washed with saturated saline and concentrated. The concentrate was dissolved in 4 ml of methanol, to which 2 ml of concentrated hydrochloric acid was added. It was allowed to react at 50 degrees for 5 h. The reaction mixture was concentrated, dissolved in 5 ml of methanol, to which 0.5 ml of ammonia was added, further concentrated, and purified by a preparative plate to obtain the final product of 4.2 mg, in a yield of 16.3%.

$^1$H NMR (400 MHz, DMSO) δ 13.12 (s, 1H), 12.63 (s, 1H), 8.58 (s, 2H), 7.68 (d, J=2.4 Hz, 1H), 7.46 (d, J=9.0 Hz, 1H), 7.11-7.08 (m, 1H), 6.04 (q, J=6.7 Hz, 1H), 4.81-4.43 (m, 4H), 3.63-3.61 (m, 4H), 3.25 (s, 2H), 2.67-2.56 (m, 4H), 1.77 (d, J=6.7 Hz, 3H).

Example 14: 1-(2-(5-(1-(3,5-dichloropyridin-4-yl)ethoxy)-1H-indazol-3-yl)-4,6-dihydropyrrolo[3,4-d]imidazol-5(1H)-yl)-2-(dimethylamino)ethan-1-one

14

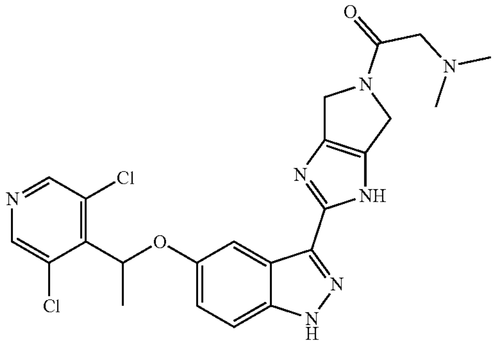

Synthetic Route of Compound 14

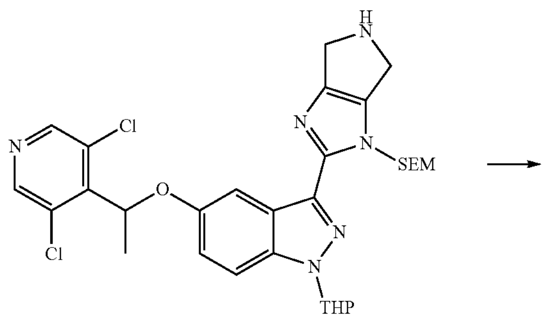

1-9

-continued

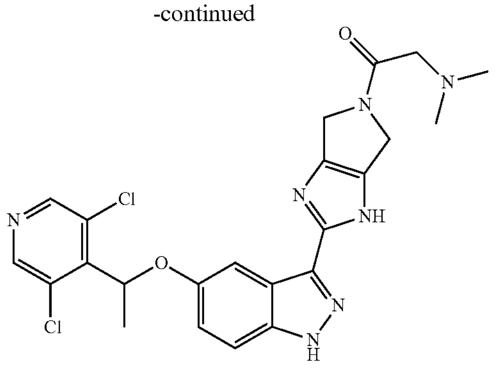

14

Synthesis Method

Synthesis of Compound 14: 1-(2-(5-(1-(3,5-dichloropyridin-4-yl)ethoxy)-1H-indazol-3-yl)-4,6-dihydropyrrolo[3,4-d]imidazol-5(1H)-yl)-2-(dimethylamino)ethyl-1-one 1-9 (50.0 mg, 0.079 mmol) was dissolved in 10 ml of DMF, to the system N,N-dimethylglycine (9.8 mg, 0.095 mmol), HATU (36.2 mg, 0.095 mmol) was added and DIPEA (20.5 mg, 0.159 mmol) was added dropwise and the reaction was carried out at room temperature. After the reaction was completed, it was quenched with water, the resulting mixture was extracted with EA, and the organic phases were combined, washed with saturated saline and concentrated. The concentrate was dissolved in 4 ml of methanol, to which 2 ml of concentrated hydrochloric acid was added. It was allowed to react at 50 degrees for 5 h. The reaction mixture was concentrated, dissolved in 5 ml of methanol, to which 0.5 ml of ammonia was added, further concentrated, and purified by a preparative plate to obtain the final product of 15.0 mg, in a yield 37.8%.

$^1$H NMR (400 MHz, DMSO) δ 8.58 (s, 2H), 7.68 (s, 1H), 7.46 (d, J=9.0 Hz, 1H), 7.11-7.08 (m, 1H), 6.04 (q, J=6.7 Hz, 1H), 4.77-4.45 (m, 4H), 3.22-3.17 (m, 2H), 2.28 (d, J=11.0 Hz, 6H), 1.76 (d, J=6.7 Hz, 3H).

Example 15: 2-(2-(5-(1-(3,5-dichloropyridin-4-yl)ethoxy)-1H-indazol-3-yl)-4,6-dihydropyrrolo[3,4-d]imidazol-5(1H)-yl)ethan-1-ol

15

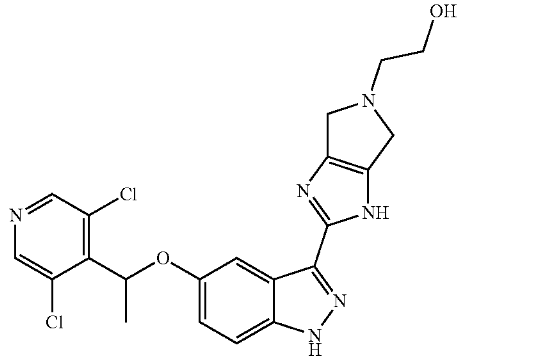

Synthetic Route of Compound 15

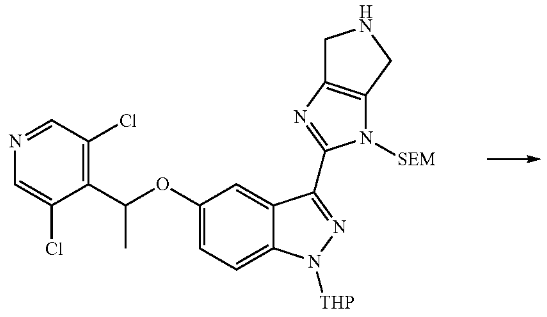

1-9

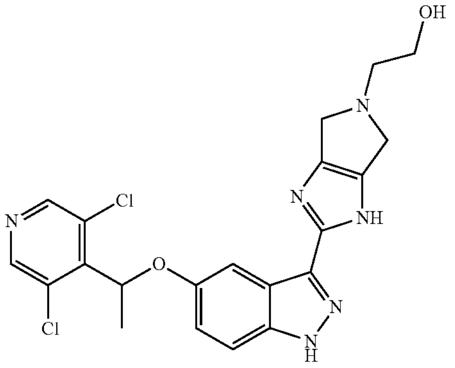

15

Synthesis Method

Synthesis of Compound 15: 2-(2-(5-(1-(3,5-dichloropyridin-4-yl)ethoxy)-1H-indazol-3-yl)-4,6-dihydropyrrolo[3,4-d]imidazol-5(1H)-yl)ethan-1-ol 1-9 (30.0 mg, 0.05 mmol) was dissolved in 10 ml of DMF, to the system (2-bromoethoxy)tert-butyldimethylsilane (17.1 mg, 0.07 mmol), and cesium carbonate (46.6 mg, 0.14 mmol) were added, and the reaction mixture was heated to 80° C. and it was allowed to react for 3 h. The reaction was quenched with water, the resulting mixture was extracted with EA, and the organic phases were combined, washed with saturated saline and concentrated. The concentrate was dissolved in 4 ml of methanol, to which 2 ml of concentrated hydrochloric acid was added. It was allowed to react at 50 degrees for 5 hours. The reaction mixture was concentrated, dissolved in 5 ml of methanol, to which 0.5 ml of ammonia was added, further concentrated, and purified by a preparative plate to obtain the final product of 10.2 mg, in a yield of 46.3%.

$^1$H NMR (400 MHz, MeOH) δ 8.46 (s, 2H), 7.63 (d, J=2.4 Hz, 1H), 7.47 (d, J=9.1 Hz, 1H), 7.19-7.07 (m, 1H), 6.17 (q, J=6.7 Hz, 1H), 4.76-4.58 (m, 4H), 3.99 (t, J=5.2 Hz, 2H), 3.69 (t, J=5.2 Hz, 2H), 1.84 (d, J=6.7 Hz, 3H).

Example 16: 5-(1-(3,5-dichloropyridin-4-yl)ethoxy)-3-(5-(methylsulfonyl)-1,4,5,6-tetrahydropyrrolo[3,4-d]imidazol-2-yl)-1H-indazole

16

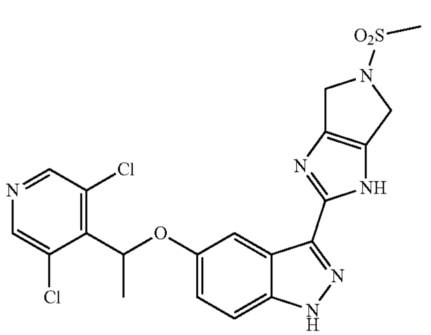

Synthetic Route of Compound 16

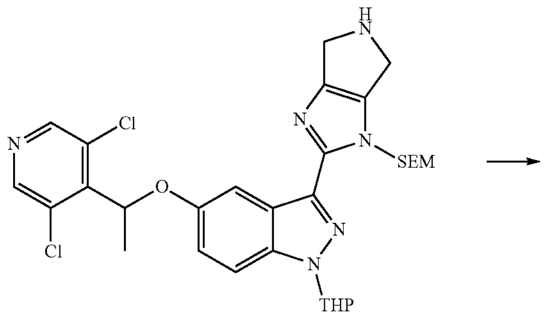

1-9

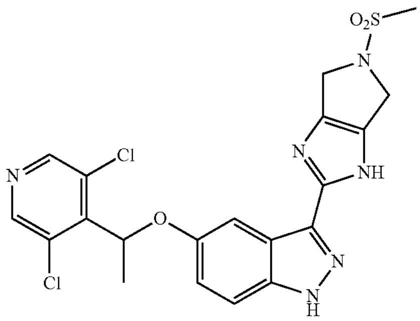

16

Synthesis Method

Synthesis of Compound 16: 5-(1-(3,5-dichloropyridin-4-yl)ethoxy)-3-(5-(methylsulfonyl)-1,4,5,6-tetrahydropyrrolo[3,4-d]imidazol-2-yl)-1H-indazole 1-9 (40.0 mg, 0.06 mmol) was dissolved in 10 ml of DCM, methanesulfonyl chloride (8.7 mg, 0.08 mmol), and triethylamine (7.7 mg, 0.08 mmol) were added to the system and the reaction was carried out at room temperature for 1 h. The reaction was quenched with water, the resulting mixture was extracted with DCM, and the organic phases were combined, washed with saturated saline and concentrated. The concentrate was dissolved in 4 ml of methanol, to which 2 ml of concentrated hydrochloric acid was added. It was allowed to react at 50 degrees for 5 h. The reaction mixture was concentrated, dissolved in 5 ml of methanol, to which 0.5 ml of ammonia was added, further concentrated, and purified by a preparative plate to obtain the final product of 10.3 mg, in a yield of 33.0%.

$^1$H NMR (400 MHz, DMSO) δ 13.13 (s, 1H), 12.68 (s, 1H), 8.59 (s, 2H), 7.66 (d, J=2.4 Hz, 1H), 7.47 (d, J=9.0 Hz, 1H), 7.11-7.09 (m, 1H), 6.03 (q, J=6.6 Hz, 1H), 4.50-4.46 (m, 4H), 3.06 (s, 3H), 1.76 (d, J=6.6 Hz, 3H).

Example 16a: (R)-5-(1-(3,5-dichloropyridin-4-yl)ethoxy)-3-(5-(methylsulfonyl)-1,4,5,6-tetrahydropyrrolo[3,4-d]imidazol-2-yl)-1H-indazole 16a

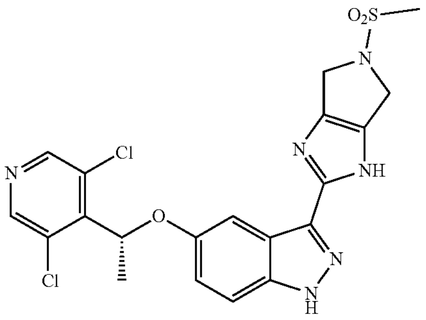

Example 16a was prepared according to the synthetic route of Example 16 using suitable starting materials. lC-MS m/z (ESI) [M+H]+ was calculated for $C_{20}H_{19}Cl_2N_6O_3S$ as: 493.0; measured as: 493.1.

Example 17: Methyl 2-(5-(1-(3,5-dichloropyridin-4-yl)ethoxy)-1H-indazol-3-yl)-4,6-dihydropyrrolo[3,4-d]imidazole-5(1H)-carboxylate

17

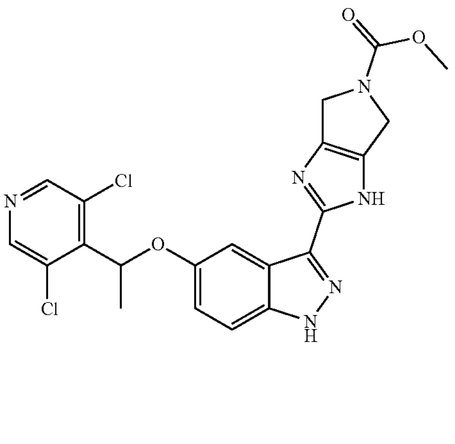

Synthetic Route of Compound 17

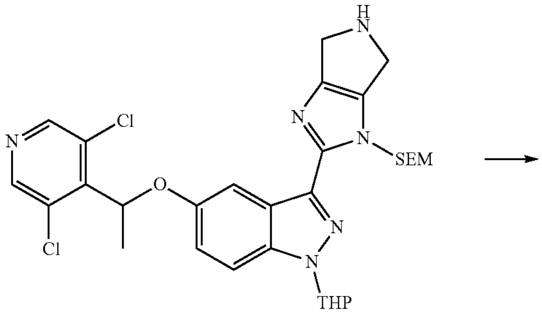

1-9

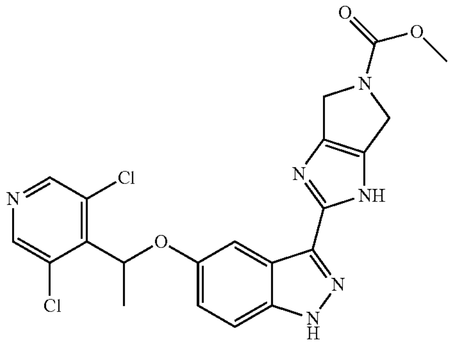

17

Synthesis Method

Synthesis of Compound 17: Methyl 2-(5-(1-(3,5-dichloropyridin-4-yl)ethoxy)-1H-indazol-3-yl)-4,6-dihydropyrrolo[3,4-d]imidazole-5(1H)-carboxylate 1-9 (50.0 mg, 0.08 mmol) was dissolved in 10 ml of dichloromethane, and the system was cooled to 0° C. To the system, triphosgene (23.6 mg, 0.08 mmol) was added and triethylamine (16.1 mg, 0.16 mmol) was added dropwise. It was allowed to react for 1 h. After the reaction is completed, it was quench with water, the resulting mixture was extract with DCM, and the organic phases were combined, washed with saturated saline and concentrated. The concentrate was dissolved in 5 ml of methanol, to which DMAP (9.7 mg, 0.08 mmol) was added. The reaction mixture was heated to 70° C. for reaction. Afther the reaction was complete, the reaction mixture was concentrated, the residue was dissolved in EA, the resulting mixture was washed with water, and the organic phase was dried over anhydrous sodium sulfate. After concentration, the residue was dissolved in 4 ml of methanol, to which 2 ml of concentrated hydrochloric acid was added. It was allowed to react at 50° C. for 5 h. The reaction mixture was concentrated, dissolved in 5 ml of methanol, to which 0.5 ml of ammonia was added, further concentrated, and purified by the preparation plate to obtain the final product 8.2 mg, in a yield of 21.8%.

$^1$H NMR (400 MHz, DMSO) δ 13.11 (s, 1H), 12.62 (s, 1H), 8.58 (s, 2H), 7.66 (d, J=2.4 Hz, 1H), 7.46 (d, J=9.0 Hz, 1H), 7.11-7.08 (m, 1H), 6.03 (q, J=6.6 Hz, 1H), 4.53-4.40 (m, 4H), 3.71 (s, 3H), 1.76 (d, J=6.6 Hz, 3H).

Example 17a: Methyl (R)-2-(5-(1-(3,5-dichloropyridin-4-yl)ethoxy)-1H-indazol-3-yl)-4,6-dihydropyrrolo[3,4-d]imidazole-5(1H)-carboxylate 17a

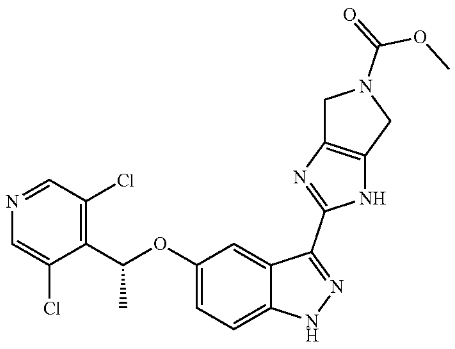

Example 17a was prepared according to the synthetic route of Example 17 using suitable starting materials. lC-MS m/z (ESI) [M+H]+ was calculated for $C_{21}H_{19}Cl_2N_6O_3$ as 473.1; measured as: 473.1.

Example 18: 5-(1-(3,5-dichloropyridin-4-yl)ethoxy)-3-(5-((1-methyl-1H-pyrazol-4-yl)sulfonyl)-1,4,5,6-tetrahydropyrrolo[3,4-d]imidazol-2-yl)-1H-indazole

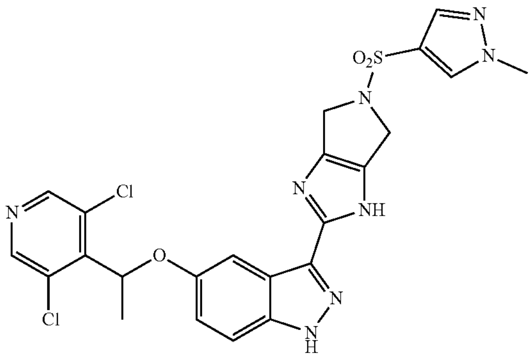

18

Synthetic Route of Compound 18

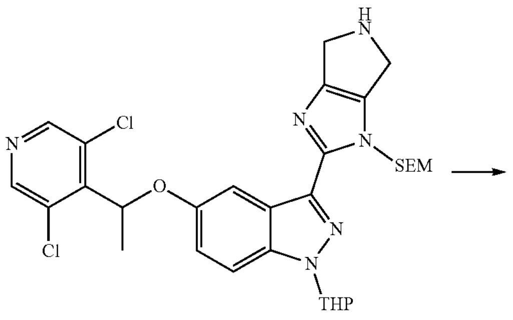

1-9

-continued

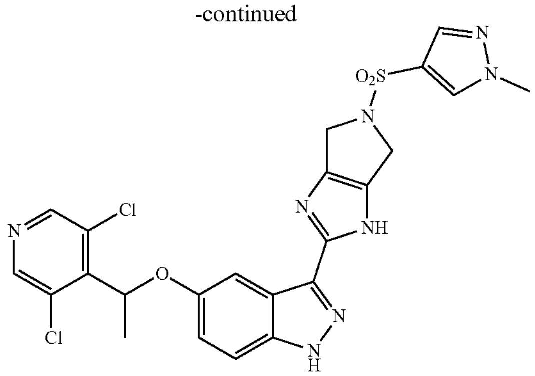

18

Synthesis Method

Synthesis of Compound 18: 5-(1-(3,5-dichloropyridin-4-yl)ethoxy)-3-(5-((1-methyl-1H-pyrazol-4-yl)sulfonyl)-1,4,5,6-tetrahydropyrrolo[3,4-d]imidazol-2-yl)-1H-indazole 1-9 (30.0 mg, 0.04 mmol) was dissolved in 10 ml of DCM, to the system pyridine-4-sulfonyl chloride (9.6 mg, 0.05 mmol) and triethylamine (5.4 mg, 0.05 mmol) were added and the reaction was carried out at room temperature for 1 h. The reaction was quenched with water, the resulting mixture was extracted with DCM, and the organic phases were combined, washed with saturated saline and concentrated. The concentrate was dissolved in 4 ml of methanol, to which 2 ml of concentrated hydrochloric acid was added. It was allowed to react at 50 degrees for 5 h. The reaction mixture was concentrated, dissolved in 5 ml of methanol, to which 0.5 ml of ammonia was added, further concentrated, and purified by a preparative plate to obtain the final product of 5.4 mg, in a yield of 20.3%.

$^1$H NMR (400 MHz, DMSO) δ 8.45 (s, 2H), 8.30 (s, 1H), 7.92 (s, 1H), 7.58 (d, J=2.4 Hz, 1H), 7.43 (d, J=9.1 Hz, 1H), 7.17-7.14 (m, 1H), 6.16 (q, J=6.7 Hz, 1H), 4.58-4.42 (m, 4H), 3.96 (s, 3H), 1.82 (d, J=6.7 Hz, 3H).

Example 19: 5-(1-(3,5-dichloropyridin-4-yl)ethoxy)-3-(1,4,5,6-tetrahydropyrrolo[3,4-d]imidazol-2-yl)-1H-indazole

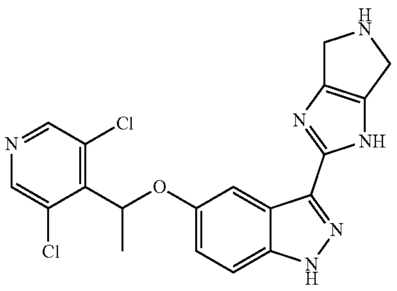

19

Synthetic Route of Compound 19

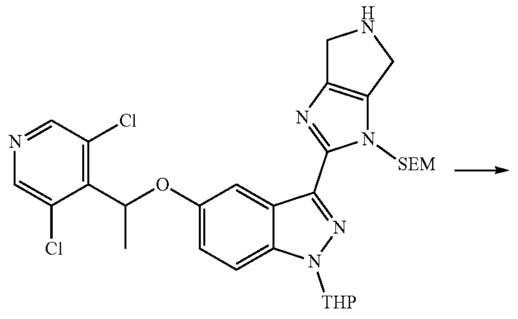

1-9

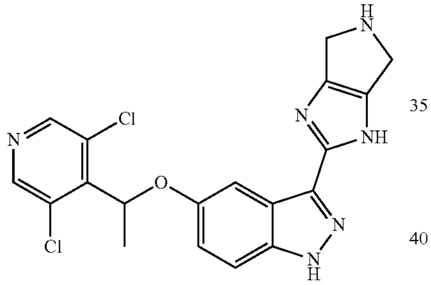

19

Synthesis Method

Synthesis of Compound 19: 5-(1-(3,5-dichloropyridin-4-yl)ethoxy)-3-(1,4,5,6-tetrahydropyrrolo[3,4-d]imidazol-2-yl)-1H-indazole 1-9 (30.0 mg, 0.05 mmol) was dissolved in 4 ml of methanol, and 2 ml of concentrated hydrochloric acid was added to the system. It was allowed to react at 50 degrees for 5 h. The reaction mixture was concentrate, dissolved in 5 ml of methanol, to which 0.5 ml of ammonia was added, further concentrated, and purified by the a preparative plate to obtain the final product 12.0 mg, in a yield of 60.7%.

$^1$H NMR (400 MHz, MeOD) δ 8.46 (s, 2H), 7.63 (d, J=2.4 Hz, 1H), 7.47 (d, J=8.8 Hz, 1H), 7.20-7.17 (m, 1H), 6.17 (q, J=6.6 Hz, 1H), 4.63-4.42 (m, 4H), 1.84 (d, J=6.6 Hz, 3H).

Example 20: 5-(1-(3,5-dichloropyridin-4-yl)ethoxy)-3-(5-((1-methyl-1H-pyrazol-3-yl)sulfonyl)-1,4,5,6-tetrahydropyrrolo[3,4-d]imidazol-2-yl)-1H-indazole

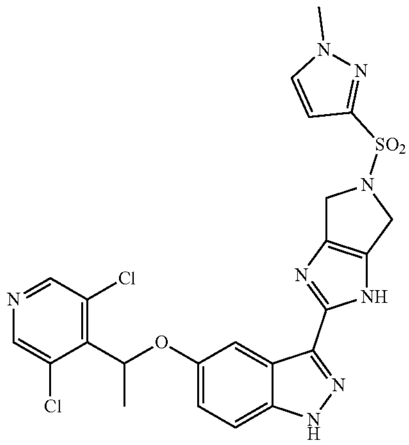

20

Synthetic Route of Compound 20

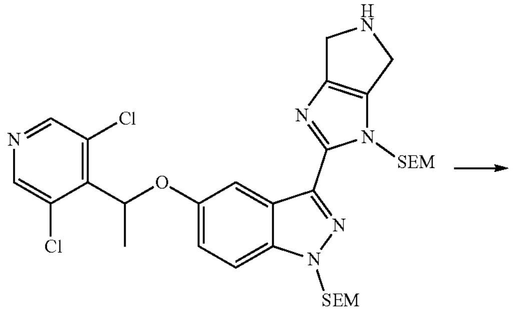

1-9

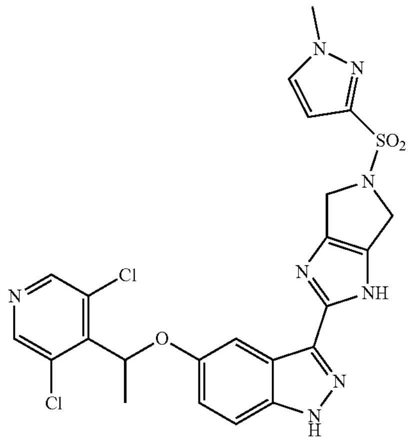

20

Synthesis Method

Synthesis of Compound 20: 5-(1-(3,5-dichloropyridin-4-yl)ethoxy)-3-(5-((1-methyl-1H-pyrazol-3-yl) sulfonyl)-1,4,5,6-tetrahydropyrrolo[3,4-d]imidazol-2-yl)-1H-indazole Intermediates 1-9 (30.0 mg, 0.04 mmol) was dissolved in DCM, and the system was cooled to zero. 1-methyl-1H-pyrazole-3-sulfonyl chloride (8.8 mg, 0.05 mmol) and triethylamine (9.0 mg, 0.09 mmol) were added dropwise to the solution and it was allowed to react at room temperature for 1 h. Water was added to the reaction solution, the resulting mixture was extracted twice with DCM, and the organic phases were combined, washed with saturated saline, dried over sodium sulfate, concentrated and purified by silica plate. The resulting product was dissolved in 2 ml of methanol and 1 ml of concentrated hydrochloric acid. It was allowed to react at 50 degrees for 6 h. The reaction mixture was concentrated, dissolved in 3 ml of methanol, to which 0.5 ml of ammonia was added, further concentrated, and purified on a preparative plate to obtain the final product of 8 mg in a yield of 33.6%.

$^1$H NMR (400 MHz, $CD_3OD$) δ 8.45 (s, 2H), 7.77 (d, J=2.4 Hz, 1H), 7.60 (d, J=2.4 Hz, 1H), 7.43 (d, J=8 Hz, 1H), 7.15 (d, J=8 Hz, 1H), 6.80 (d, J=2.4 Hz, 1H), 6.14-6.19 (m, 1H), 4.56-4.65 (m, 4H), 3.97 (s, 3H), 1.82 (d, J=4 Hz, 3H).

Example 21: 3-(2-(5-(1-(3, 5-dichloropyridin-4-yl) ethoxy)-1H-indazol-3-yl)-4,6-dihydropyrrolo[3,4-d] imidazol-5(1H)-yl)cyclobutan-1-ol

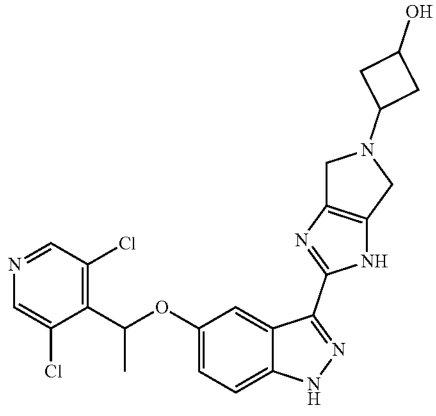

21

Synthetic Route of Compound 21

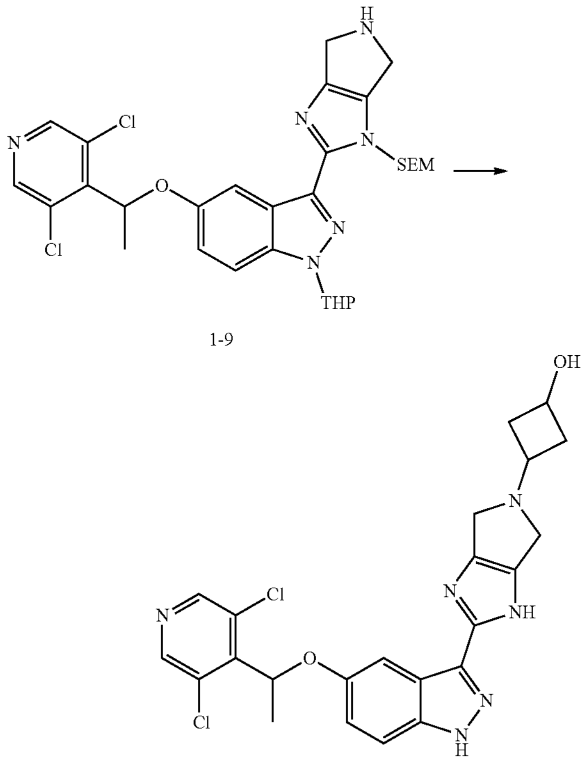

1-9

21

Synthesis Method

Synthesis of Compound 21: 3-(2-(5-(1-(3, 5-dichloropyridin-4-yl)ethoxy)-1H-indazol-3-yl)-4, 6-dihydropyrrolo[3,4-d]imidazol-5(1H)-yl)cyclobutan-1-ol Intermediate 1-9 (30.0 mg, 0.05 mmol) was dissolved in 5 ml dichloromethane, and 3-(benzyloxy)-1-cyclobutanone (10.1 mg, 0.06 mmol) was added, and the resulting mixture was stirred for 20 min at room temperature. Sodium triacetylborohydride (13.1 mg, 0.06 mmol) was added, and it was allowed to react for 2 h at room temperature. Water was added to the reaction solution, the resulting mixture was extracted twice with dichloromethane and the organic phases were combined, washed with saturated saline and dried over anhydrous sodium sulfate. The concentrated crude product was dissolved in 5 ml of methanol, 10% Pd/C (6 mg) was added, and hydrogen gas was replaced 3 times. The reaction was carried out at room temperature for 3 h. The palladium carbon was removed by filtration, and the filtrate was concentrated. The resulting product was dissolved in 2 ml of methanol and 1 ml of concentrated hydrochloric acid, and the reaction was carried out at 50 degrees for 6 h. The reaction mixture was concentrated, dissolved in 3 ml of methanol, to which 0.5 ml of ammonia was added, further concentrated and purified to obtain the final product of 2.7 mg, with a total yield of 11.7% in three steps.

$^1$H NMR (400 MHz, MeOD) δ 8.45 (s, 2H), 7.64 (d, J=4.0 Hz, 1H), 7.45 (d, J=8.0 Hz, 1H), 7.16 (dd, J=4.0 Hz, J=8.0

Hz, 1H), 6.19 (dd, J=8.0 Hz, J=16.0 Hz, 1H), 4.07-4.04 (m, 1H), 3.96 (s, 4H), 3.19-3.15 (m, 1H), 2.67-2.60 (m, 2H), 2.04-1.98 (m, 2H), 1.83 (d, J=8.0 Hz, 3H).

Example 22: 4-(2-(5-(1-(3, 5-dichloropyridin-4-yl) ethoxy)-1H-indazol-3-yl)-4, 6-dihydropyrrolo[3,4-d] imidazol-5(1H)-yl)cyclohexan-1-ol

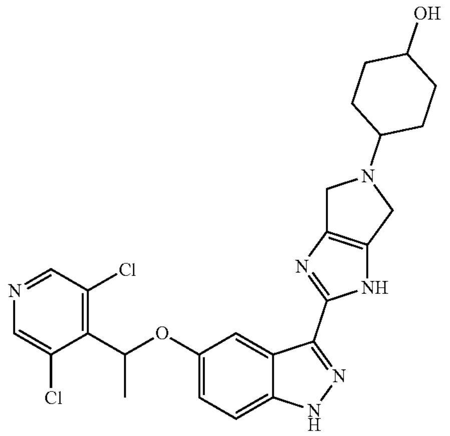

22

Synthetic Route of Compound 22

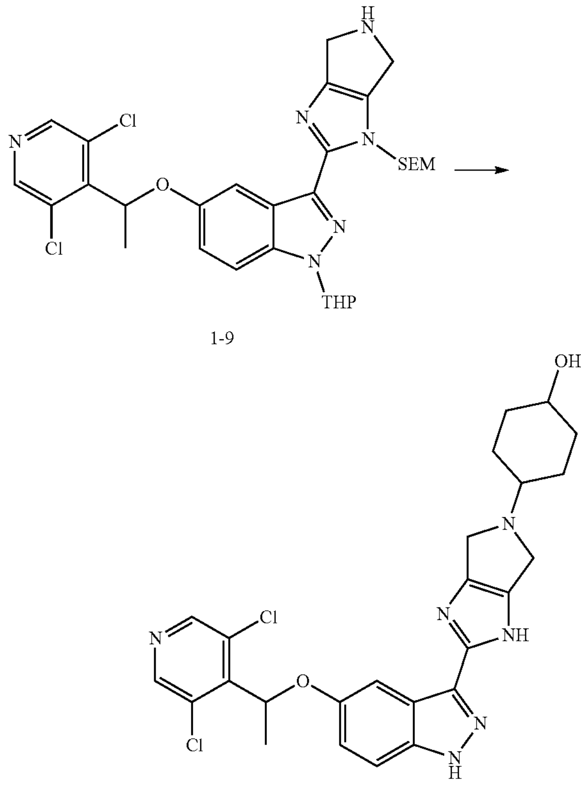

1-9

22

Synthesis Method

Synthesis of Compound 22: 4-(2-(5-(1-(3, 5-dichloropyridin-4-yl)ethoxy)-1H-indazol-3-yl)-4, 6-dihydropyrrolo[3,4-d]imidazol-5(1H)-yl)cyclohexan-1-ol Intermediate 1-9 (30.0 mg, 0.05 mmol) was dissolved in 5 ml of dichloromethane, and 4-hydroxycyclohexanone (8.1 mg, 0.07 mmol) was added. The resulting mixture was stirred for 20 min at room temperature. Sodium triacetylborohydride (15.1 mg, 0.07 mmol) was added. It was allowed to react for 2 h at room temperature. Water was added to the reaction solution, the resulting mixture was extracted twice with dichloromethane, and the organic phases were combined, washed with saturated saline, and dried over anhydrous sodium sulfate. The concentrated product was dissolved in 2 ml of methanol and 1 ml of concentrated hydrochloric acid. It was allowed to react at 50 degrees for 6 h. The reaction mixture was concentrated, dissolved in 3 ml of methanol, to which 0.5 ml of ammonia was added, further concentrated and purified to obtain the final product of 3.8 mg, with a total yield of 15.5% in two steps.

$^1$H NMR (400 MHz, MeOD) δ 8.45 (s, 2H), 7.64 (d, J=4.0 Hz, 1H), 7.43 (d, J=8.0 Hz, 1H), 7.16 (dd, J=4.0 Hz, J=8.0 Hz, 1H), 6.20 (dd, J=8.0 Hz, J=16.0 Hz, 1H), 4.05 (s, 2H), 4.00 (s, 2H), 3.95 (s, 1H), 2.82-2.71 (m, 1H), 2.14-2.13 (m, 1H), 2.06-2.03 (m, 1H), 1.91-1.82 (m, 7H), 1.67-1.64 (m, 2H).

Example 23: Ethyl 2-(5-(1-(3,5-dichloropyridin-4-yl)ethoxy)-1H-indazol-3-yl)-4,6-dihydropyrrolo[3,4-d]imidazole-5(1H)-carboxylate

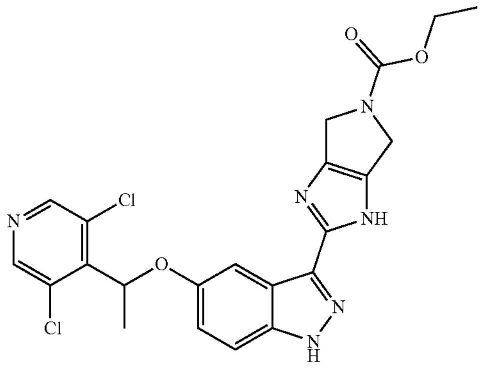

23

Synthetic Route of Compound 23

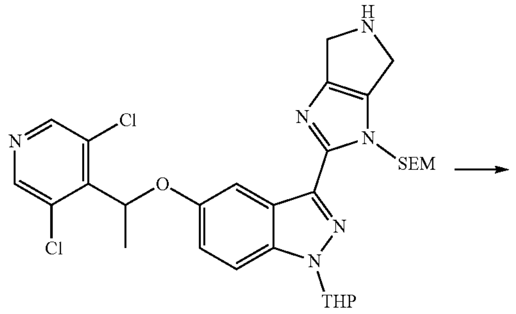

1-9

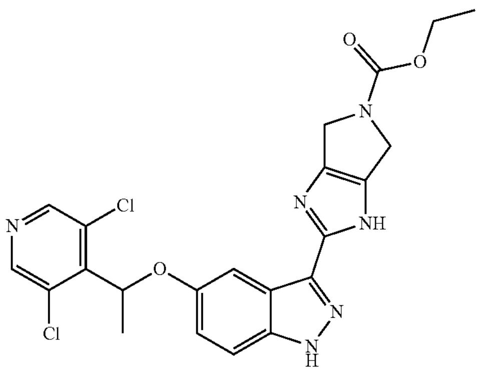

23

Synthesis Method

Synthesis of Compound 23: ethyl 2-(5-(1-(3,5-dichloropyridin-4-yl)ethoxy)-1H-indazol-3-yl)-4,6-dihydropyrrolo[3,4-d]imidazole-5(1H)-carboxylate Triphosgene (28.3 mg, 0.10 mmol) was dissolved in 10 ml of anhydrous dichloromethane and to the system, a solution of Intermediate 1-9 (60 mg, 0.10 mmol) in dichloromethane (5 ml) was added dropwise at 0 degree, followed by slow dropwise addition of anhydrous triethylamine (0.13 ml, 1.00 mmol). The resulting mixture was stirred at room temperature for 10 min, and the reaction solution was concentrated and dissolved in 10 ml of ethanol, added DMAP (11.6 mg, 0.09 mmol) was added and the reaction was carried out at 50 degrees for 2 hours. The reaction was quenched with water, the resulting mixture was extracted twice with DCM, and the organic phases were combined, dried, and concentrated. The concentrate was dissolved in 4 ml of methanol, to which 2 ml of concentrated hydrochloric acid was added. It was allowed to react at 50° C. for 7 h. The reaction mixture was concentrated, dissolved in 5 ml of methanol, to which 0.5 ml of ammonia was added, further concentrated, and purified by a preparative plate to finally obtain a white solid of 25 mg, in a yield of 53.8%. 1C-MS m/z (ESI) [M+H]+ calculated for $C_{22}H_{21}Cl_2N_6O_3$ as 487.1; measured as 487.1.

Example 24: 2-cyanoethyl 2-(5-(1-(3,5-dichloropyridin-4-yl)ethoxy)-1H-indazol-3-yl)-4,6-dihydropyrrolo[3,4-d]imidazole-5(1H)-carboxylate

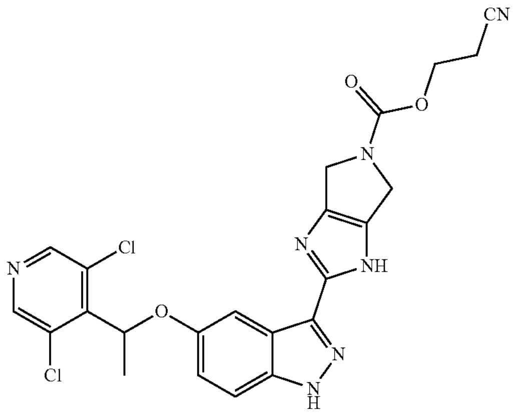

24

Synthetic Route of Compound 24

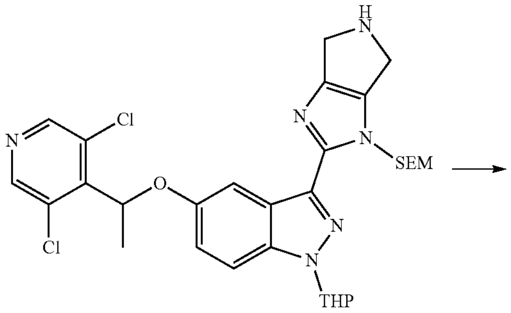

1-9

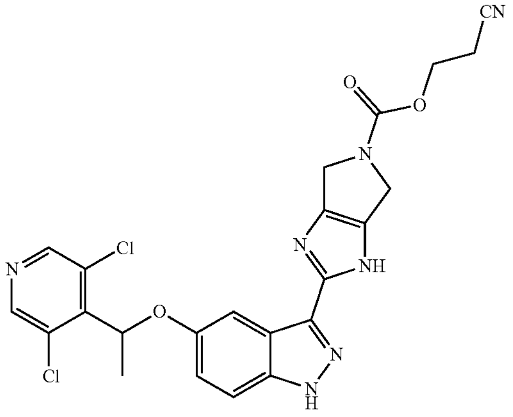

24

Synthesis Method

Synthesis of Compound 24: 2-cyanoethyl 2-(5-(1-(3,5-dichloropyridin-4-yl)ethoxy)-1H-indazol-3-yl)-4,6-dihydropyrrolo[3,4-d]imidazole-5(1H)-carboxylate 1-9 (40.0 mg, 0.06 mmol) was dissolved in 10 ml DCM, and was cooled to 0° C. Under nitrogen protection, triphosgene (20.1 mg, 0.06 mmol) was added, and TEA (19.2 mg, 0.19 mmol) was slowly added dropwise. It was allowed to react for 10 min. The reaction mixture was concentrated. The residue was dissolved in 10 ml of THF, to which 3-hydroxypropionitrile (22.6 mg, 0.32) and DMAP (0.98 mg, 0.01 mmol) were added. It was allowed to react at 50° C. for 2 h. To the reaction solution, water was added and the resulting mixture was extracted with ethyl acetate twice. The organic phases were combined, washed twice with ammonium chloride solution, washed with saturated saline, dried over anhydrous sodium sulfate, and concentrated. The concentrate was dissolved in 6 ml of 1,4-dioxane, to which 3 ml of concentrated hydrochloric acid was added, concentrated and purified by a preparative plate to obtain a final product of 3 mg in a yield of 7.5%. LC-MS m/z (ESI) [M+H]+ for $C_{23}H_{20}C_{l2}N_7O_3$ was calculated as: 512.1; and measured as: 512.1.

Example 25: Cyclopropyl (2-(5-(1-(3, 5-dichloropyridin-4-yl)ethoxy)-1H-indazol-3-yl)-4, 6-dihydropyrrolo[3,4-d]imidazol-5(1H)-yl)ketone

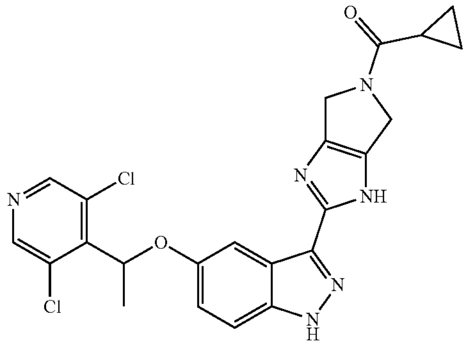

25

Synthetic Route of Compound 25

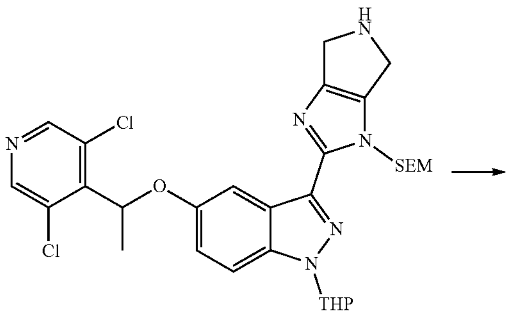

1-9

-continued

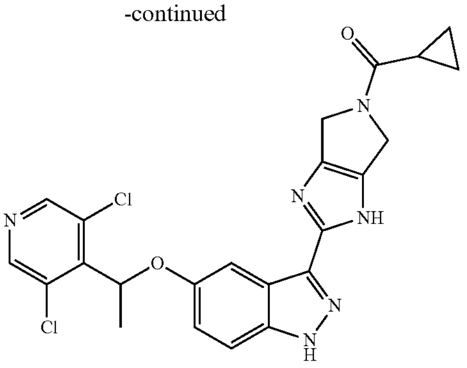

25

Synthesis Method

Synthesis of Compound 25: Cyclopropyl (2-(5-(1-(3, 5-dichloropyridin-4-yl)ethoxy)-1H-indazol-3-yl)-4, 6-dihydropyrrolo[3,4-d]imidazol-5(1H)-yl)ketone Intermediate 1-9 (30.0 mg, 0.05 mmol) was dissolved in 5 ml of dichloromethane, to which triethylamine (14.5 mg, 0.14 mmol) was added. The mixture was cooled to 0° C. Cyclopropyl formyl chloride (5.5 mg, 0.05 mmol) was added. It was allowed to react at room temperature for 1 h. Water was added to the reaction solution, the reaction mixture was extracted twice with dichloromethane, and the organic phases were combined, washed with saturated saline, dired over anhydrous sulfate and concentrated. The crude product was dissolved in 2 ml of methanol and 1 ml of concentrated hydrochloric acid. It was allowed to react for 6 h at 50° C. The reaction mixture was concentrated, dissolved in 3 ml of methanol, to which 0.5 ml of ammonia was added, further concentrated and purified to give a final product of 6.7 mg in a total yield of 28.9% in three steps. LC-MS m/z (ESI) [M+H]+ for $C_{23}H_{21}C_{l2}N_6O_2$ was calculated as. 483.1; measured as: 483.1.

Example 26: (2-(5-(1-(3, 5-dichloropyridin-4-yl)ethoxy)-1H-indazol-3-yl)-4, 6-dihydropyrrolo[3,4-d]imidazol-5(1H)-yl)(3-hydroxycyclobutyl)ketone

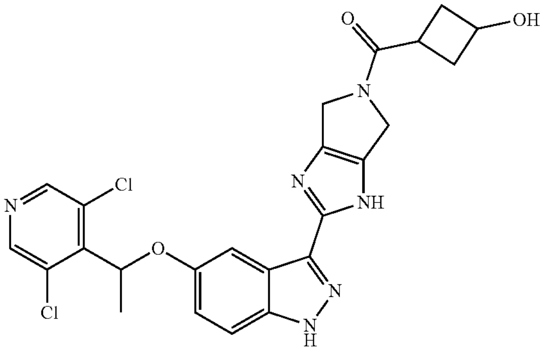

26

Synthetic Route of Compound 26

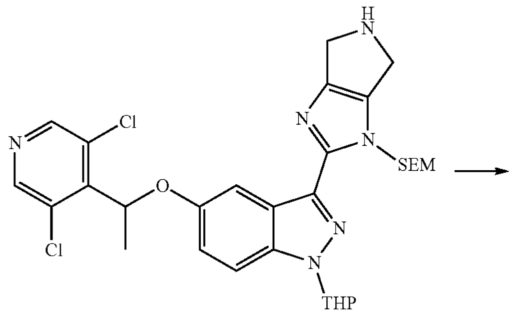

1-9

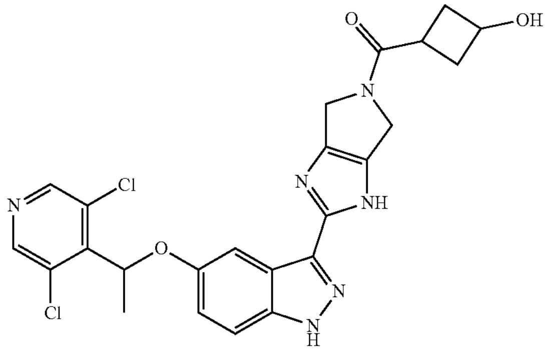

26

Synthesis Method

Synthesis of Compound 26: (2-(5-(1-(3, 5-dichloropyridin-4-yl)ethoxy)-1H-indazol-3-yl)-4, 6-dihydropyrrolo[3,4-d]imidazol-5(1H)-yl)(3-hydroxycyclobutyl) ketone Intermediate 1-9 (30.0 mg, 0.05 mmol) was dissolved in 2 ml DMF and 3-hydroxycyclobutanecarboxylic acid (6.1 mg, 0.05 mmol), HATU (20.0 mg, 0.05 mmol) and DIPEA (12.3 mg, 0.10 mmol) were added. It was allowed to react for 3 h at room temperature. To the reaction solution, water was added and the resulting mixture was extracted twice with EA. The organic phases were combined, washed with saturated saline, dried over anhydrous sodium sulfate, concentrated and purified. The resulting product was dissolved in 2 ml of methanol and 1 ml of concentrated hydrochloric acid. It was allowed to react at 50 degrees for 6 h. The reaction mixture was concentrated, dissolved in 3 ml of methanol, to which 0.5 ml of ammonia was added, further concentrated and purified to give a final product of 4.1 mg, with a total yield of 16.7% in two steps.

$^1$H NMR (400 MHz, MeOD) δ 8.46 (s, 2H), 7.66 (d, J=4.0 Hz, 1H), 7.45 (d, J=8.0 Hz, 1H), 7.16 (dd, J=4.0 Hz, J=8.0 Hz, 1H), 6.19 (dd, J=8.0 Hz, J=16.0 Hz, 1H), 4.71-4.62 (m, 4H), 4.26-4.20 (m, 1H), 2.98-2.92 (m, 1H), 2.63-2.60 (m, 2H), 2.24-2.19 (m, 2H), 1.83 (d, J=4.0 Hz, 3H).

Example 27: 3-(2-(5-(1-(3, 5-dichloropyridin-4-yl)ethoxy)-1H-indazol-3-yl)-4, 6-dihydropyrrolo[3,4-d]imidazol-5(1H)-yl)-3-oxopropionitrile

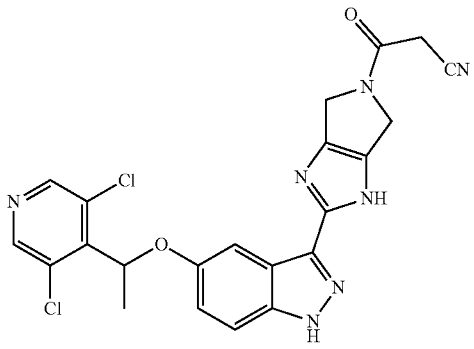

27

Synthetic Route of Compound 27

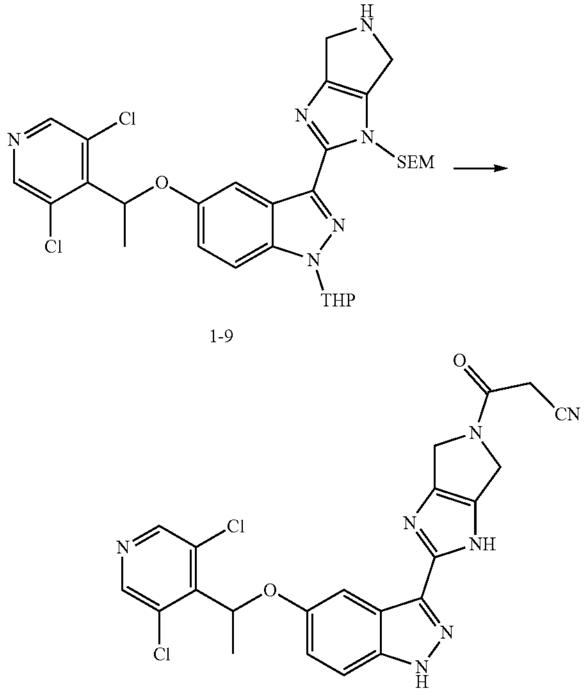

1-9

27

Synthesis Method

Synthesis of Compound 27: 3-(2-(5-(1-(3, 5-dichloropyridin-4-yl)ethoxy)-1H-indazol-3-yl)-4, 6-dihydropyrrolo[3,4-d]imidazol-5(1H)-yl)-3-oxopropionitrile Intermediate 1-9 (25.0 mg, 0.04 mmol) was dissolved in 2 ml DMF, and cyanoacetic acid (4.0 mg, 0.05 mmol), HATU (18.1 mg, 0.05 mmol) and DIPEA (15.3 mg, 0.12 mmol) were added. It was allowed to react for 3 h at room temperature. Water was added to the reaction solution, the resulting mixture was extracted twice with EA and the organic phases were combined, washed with saturated saline, dried over anhydrous sodium sulfate, concentrated and purified. The resulting product was dissolved in 2 ml of methanol and 1 ml of concentrated hydrochloric acid. It was allowed to react at 50° C. for 6 h. The reaction solution was concentrated, dissolved in 3 ml of methanol, to which 0.5 ml of ammonia was added, further concentrated and purified to give a final product of 5.9 mg in a yield of 30.9%.

$^1$H NMR (400 MHz, MeOD) δ 8.46 (s, 2H), 7.64 (d, J=4.0 Hz, 1H), 7.45 (d, J=8.0 Hz, 1H), 7.16 (dd, J=4.0 Hz, J=8.0 Hz, 1H), 6.19 (dd, J=8.0 Hz, J=12.0 Hz, 1H), 4.61 (s, 4H), 3.65 (s, 2H), 1.83 (d, J=4.0 Hz, 3H).

Example 28: 5-(1-(3,5-dichloropyridin-4-yl)ethoxy)-3-(5-(ethylsulfonyl)-1,4,5,6-tetrahydropyrrolo[3,4-d]imidazol-2-yl)-1H-indazole

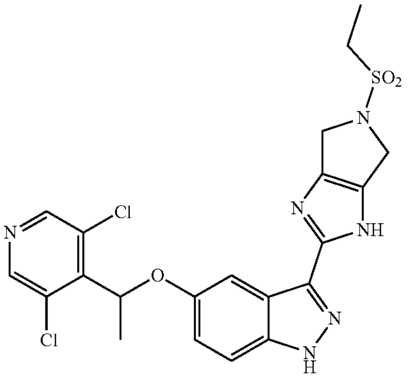

28

Synthetic Route of Compound 28

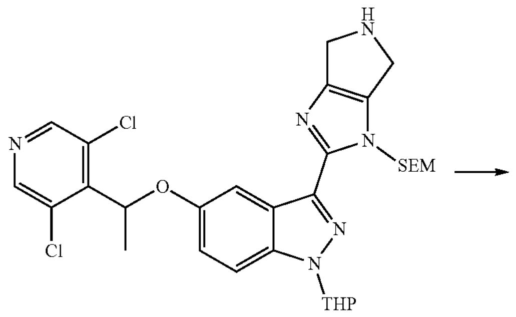

1-9

-continued

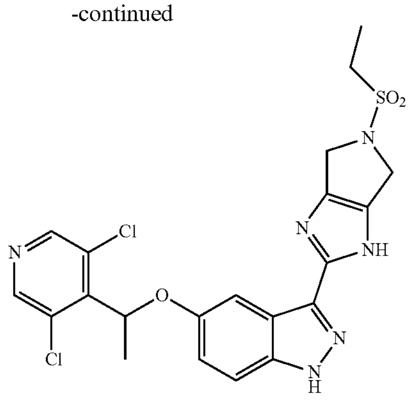

28

Synthesis Method

Synthesis of Compound 28: 5-(1-(3,5-dichloropyridin-4-yl)ethoxy)-3-(5-(ethylsulfonyl)-1,4,5,6-tetrahydropyrrolo[3,4-d]imidazol-2-yl)-1H-indazole Intermediate 1-9 (40.0 mg, 0.06 mmol), TEA (26.1 mg, 0.19 mmol), and 5 ml DCM were added to a reaction vial. The system was cooled to 0° C. Ethyl sulfonyl chloride (11.6 mg, 0.08 mmol) was added dropwise. After the addition was complete, it was allowed to warm to room temperature and to react for 15 min. The reaction was quenched with water, the resulting mixture was extracted twice with DCM, and the organic phases were combined, dried, and concentrated. The concentrated was dissolved in 4 ml methanol, to which 2 ml concentrated hydrochloric acid was added. It was allowed to react at 50° C. for 7 h. The reaction mixture was concentrated, dissolved in 5 ml methanol, to which 0.5 ml ammonia was added, further concentrated, and purified by a preparative plate to finally obtain a white solid of 15 mg, in a yield of 46.3%. LC-MS m/z (ESI) $[M+H]^+$ for $C_{21}H_{21}Cl_2N_6O_3S$ was calculated as: 507.1; and measured as: 507.1.

Example 29: 3-(5-(Cyclopropylsulfonyl)-1,4,5,6-tetrahydropyrrolo[3,4-d]imidazol-2-yl)-5-(1-(3,5-dichloropyridin-4-yl)ethoxy)-1H-indazole

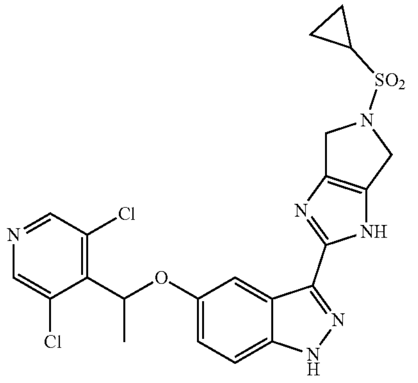

29

Synthetic Route of Compound 29

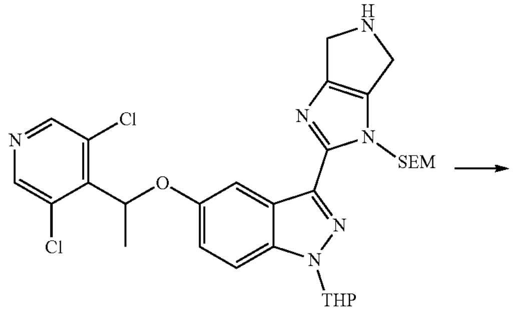

1-9

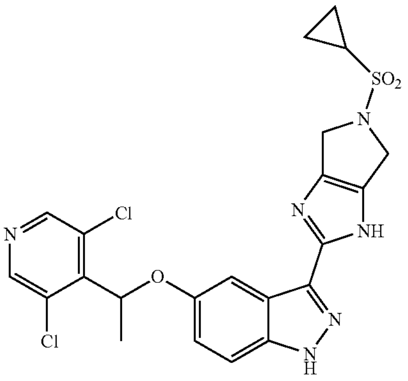

29

Synthesis Method

Synthesis of Compound 29: 3-(5-(cyclopropylsulfonyl)-1,4,5,6-tetrahydropyrrolo[3,4-d]imidazol-2-yl)-5-(1-(3,5-dichloropyridin-4-yl)ethoxy)-1H-indazole Intermediate 1-9 (40.0 mg, 0.06 mmol), TEA (26.2 mg, 0.19 mmol), and 5 ml DCM were added to a reaction vial. The system was cooled to 0° C. and cyclopropane sulfonyl chloride (11.6 mg, 0.08 mmol) was added dropwise. Afther the dropwise addition was complete, it was allowed to warm to room temperature and to react for 15 min. The reaction was quenched with water, the resulting mixture was extracted twice with DCM, and the organic phases were combined, dried, and concentrated. The concentrate was dissolved in 4 ml methanol, to which 2 ml concentrated hydrochloric acid was added. It was allowed to reacteat 50° C. for 7 h. The reaction mixture was concentrated, dissolved in 5 ml methanol, to which 0.5 ml ammonia was added, further concentrated, and purified by a preparative plate to finally obtain a white solid of 14 mg, in a yield of 42.3%. LC-MS m/z (ESI) [M+H]+ for $C_{22}H_{21}C_{l2}N_6O_3S$ was calculated as: 519.1; measured as: 519.1.

Example 30: 5-(1-(3,5-dichloropyridin-4-yl)ethoxy)-3-(5-(isopropylsulfonyl)-1,4,5,6-tetrahydropyrrolo[3,4-d]imidazol-2-yl)-1H-indazole

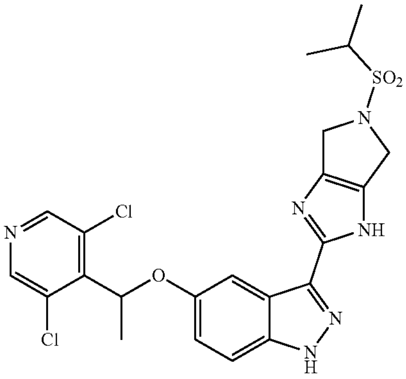

30

Synthetic Route of Compound 30

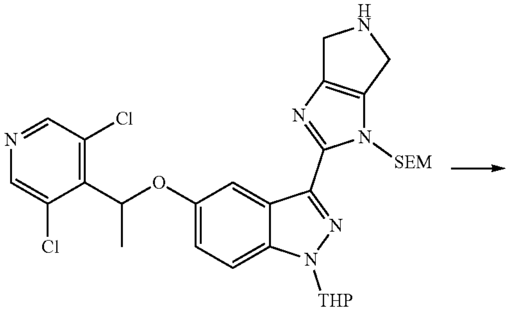

1-9

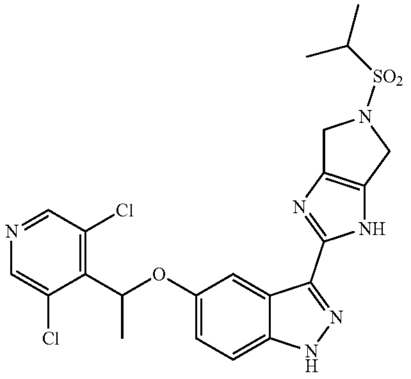

30

Synthesis Method

Synthesis of Compound 30: 5-(1-(3,5-dichloropyridin-4-yl)ethoxy)-3-(5-(isopropylsulfonyl)-1,4,5,6-tetrahydropyrrolo[3,4-d]imidazol-2-yl)-1H-indazole Intermediate 1-9 (40.0 mg, 0.06 mmol), TEA (26.2 mg, 0.19 mmol), and 5 ml DCM were added to a reaction vial.

The system was cooled to 0° C. and isopropylsulfonyl chloride (11.6 mg, 0.08 mmol) was added dropwise. After the addition dropwise was complete, it was allowed to warm to room temperature and to react for 15 min. The reaction was quenched with water, the resulting mixture was extracted twice with DCM, and the organic phases were combined, dried, and concentrated. The concentrate was dissolved in 4 ml of methanol, to which 2 ml of concentrated hydrochloric acid was added. It was allowed to react at 50° C. for 7 h. The reaction mixture was concentrated, dissolved in 5 ml of methanol, to which 0.5 ml of ammonia was added, further concentrated, and purified by a preparative plate, to finally obtain a white solid of 14 mg, in a yield of 42.1%. LC-MS m/z (ESI) $[M+H]^+$ for $C_{22}H_{23}C_{l2}N_6O_3S$ was calculated as: 521.1; measured as: 521.1.

Example 31: 1-(2-(5-(1-(3,5-dichloropyridin-4-yl)ethoxy)-1H-indazol-3-yl)-4,6-dihydropyrrolo[3,4-d]imidazol-5(1H)-yl)-2-(3-hydroxypyrrolidin-1-yl)ethan-1-one

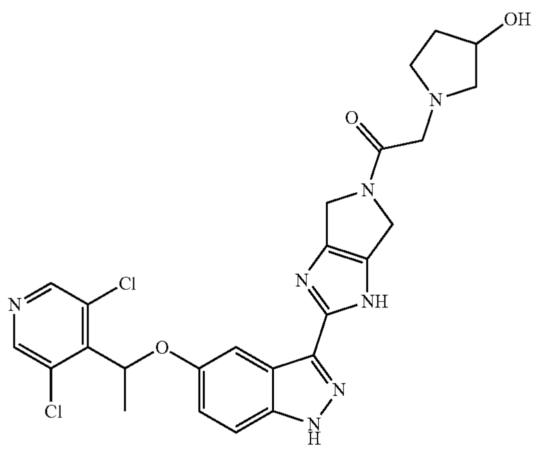

31

Synthetic Route of Compound 31

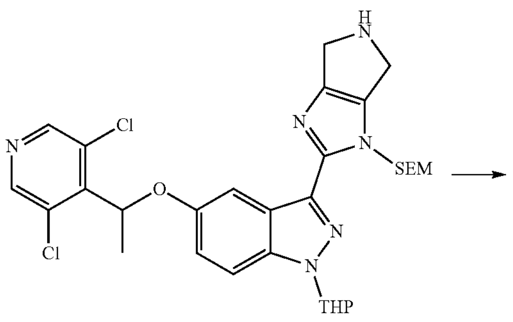

1-9

-continued

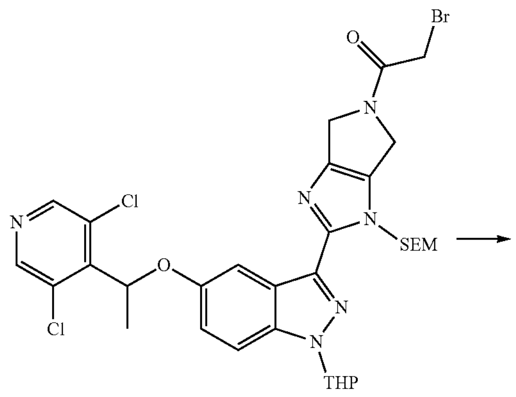

31-1

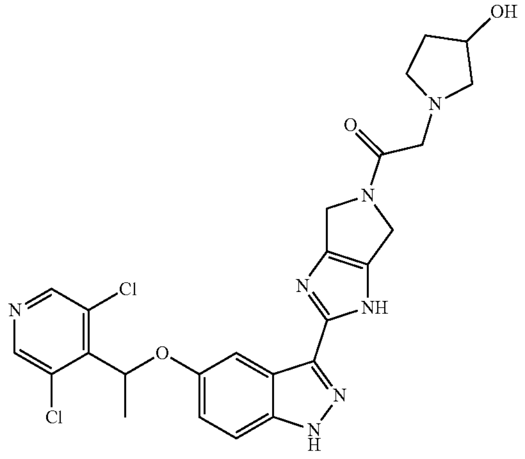

31

Synthesis Method

Synthesis of Intermediate 31-1: 2-bromo-1-(2-(5-(1-(3,5-dichloropyridin-4-yl)ethoxy)-1-((2-(trimethylsilyl)ethoxy)methyl)-1H-indazol-3-yl)-1-(((2-(trimethylsilyl) ethoxy)methyl)-4,6-dihydropyrrolo[3,4-d]imidazol-5(1H)-yl) ethan-1-one Intermediate 1-9 (30 mg, 0.04 mmol) was dissolved in DCM, and the system was cooled to zero. To the solution, bromoacetyl chloride (7.7 mg, 0.05 mmol) and triethylamine (9.0 mg, 0.09 mmol) were added dropwise. It was allowed to react for 1 h at room temperature. Water was added to the reaction solution, the resulting mixture was extracted twice with DCM, and the organic phases were combined, washed with saturated saline, dried over anhydrous sodium sulfate, concentrated and purified on silica gel plate to obtain Intermediate 31-1 of 26 mg, in a yield of 73.5%.

$^1H$ NMR (400 MHz, $CDCl_3$) δ 8.40 (d, J=8 Hz, 2H), 7.81 (s, 1H), 7.49-7.53 (m, 1H), 7.19 (d, J=12 Hz, 1H), 6.12-6.18 (m, 1H), 5.83-6.02 (m, 2H), 5.67-5.72 (m, 1H), 4.71-4.91 (m, 4H), 4.16-4.23 (m, 1H), 4.00 (s, 2H), 3.76-3.78 (m, 1H), 3.57-3.61 (m, 2H), 2.06-2.15 (m, 2H), 1.83 (d, J=4 Hz, 3H), 1.70-1.78 (m, 4H), 1.43 (t, J=6 Hz, 2H).

Synthesis of Compound 31: 1-(2-(5-(1-(3,5-dichloropyridin-4-yl)ethoxy)-1H-indazol-3-yl)-4,6-dihydropyrrolo[3,4-d]imidazol-5(1H)-yl)-2-(3-hydroxypyrrolidin-1-yl)ethan-1-one Intermediate 31-1 (26 mg, 0.03 mmol) was dissolved in acetonitrile and pyrrolidin-3-ol (3.7 mg, 0.04 mmol) and cesium carbonate (31.9 mg, 0.10 mmol) were added to the solution. It was allowed to react at 80 degrees for 1 h. Water was added to the reaction solution, the resulting mixture was extracted twice with ethyl acetate, and the organic phases were combined, washed with saturated saline, dried over anhydrous sodium sulfate and purified by silica gel plate. The resulting product was dissolved in 2 ml of methanol and 1 ml of concentrated hydrochloric acid. It was allowed to react at 50 degrees for 6 h. The reaction mixture was concentrated, dissolved in 3 ml of methanol, to which 0.5 ml of ammonia was added, concentrated, and purified by a preparative plate to obtain a final product of 6 mg, in a yield of 34.0%.

$^1$H NMR (400 MHz, DMSO) δ 13.13 (s, 1H), 12.64 (s, 1H), 8.58 (s, 2H), 7.67 (d, J=4 Hz, 1H), 7.47 (d, J=12 Hz, 1H), 7.10 (d, J=8 Hz, 1H), 6.02-6.07 (m, 1H), 4.80-4.84 (m, 1H), 4.67-4.77 (m, 2H), 4.43-4.49 (m, 2H), 4.23-4.25 (m, 1H), 3.41-3.49 (m, 2H), 2.77-2.96 (m, 2H), 2.58-2.68 (m, 2H), 1.99-2.04 (m, 1H), 1.76 (d, J=4 Hz, 3H), 1.58-1.64 (m, 1H).

Example 32: 1-(2-(2-(5-(1-(3,5-dichloropyridin-4-yl)ethoxy)-1H-indazol-3-yl)-4,6-dihydropyrrolo[3,4-d]imidazol-5(1H)-yl)-2-oxoethyl)pyrrolidine-3-carbonitrile

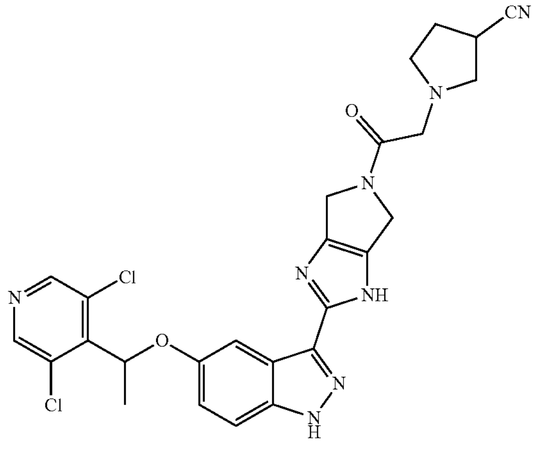

32

Synthetic Route of Compound 32

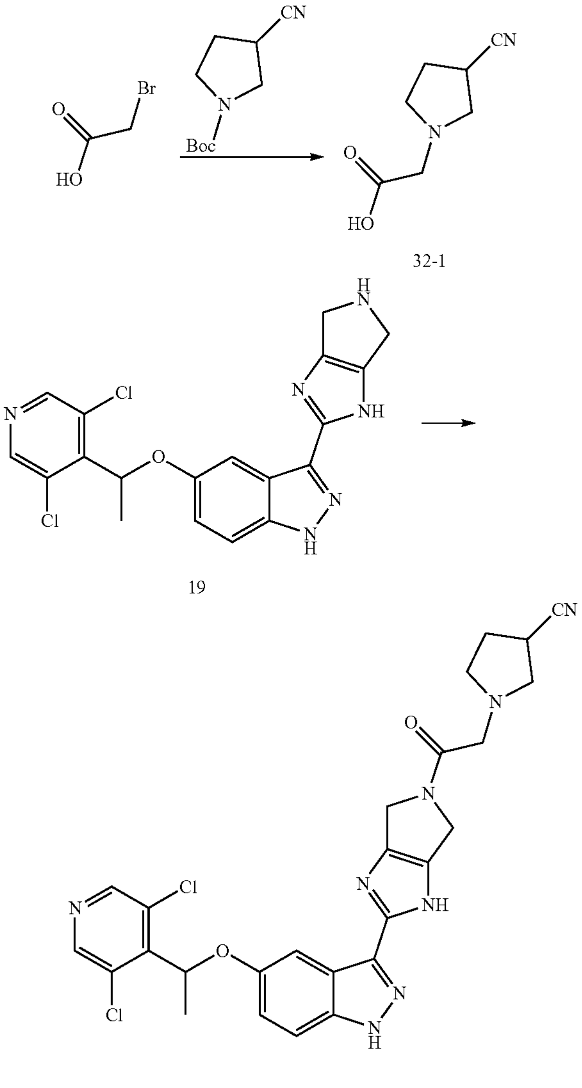

32-1

19

32

Synthesis Method

Synthesis of Intermediate 32-1: 2-(3-cyanopyrrolidin-1-yl)acetic acid

Tert-butyl 3-cyanopyrrolidine-1-carboxylate (100 mg, 0.51 mmol) was dissolved in dichloromethane (2.5 ml), and trifluoroacetic acid (0.5 ml) was added to the solution. It was allowed to react for 2 h at room temperature. The reaction mixture was concentrated. To the concentrate, 2-bromo-acetic acid (70.8 mg, 0.51 mmol) and triethylamine (154.4 mg, 1.53 mmol) were added. It was allowed to react for 4 h at 50° C. Water was added to the raction solution, the resulting mixture was extracted with ethyl acetate twice and the organic phases were combined, washed with saturated saline, dried over anhydrous sodium sulfate, concentrated and purified by silica gel column to give 30 mg of the final product in a yield of 38.2%.

$^1H$ NMR (400 MHz, $CDCl_3$) δ 3.49 (s, 2H), 3.35-3.40 (m, 1H), 3.21-3.25 (m, 1H), 3.05-3.13 (m, 2H), 2.96-3.03 (m, 1H), 2.36-2.45 (m, 1H), 2.23-2.29 (m, 1H).

Synthesis of Compound 32: 1-(2-(2-(5-(1-(3,5-dichloropyridin-4-yl)ethoxy)-1H-indazol-3-yl)-4,6-dihydropyrrolo[3,4-d]imidazol-5(1H)-yl)-2-oxoethyl)pyrrolidine-3-carbonitrile Compound 19 (20 mg, 0.05 mmol) was dissolved in DMF, and to the solution, intermediate 32-1 (8.9 mg, 0.06 mmol), HATU (22.0 mg, 0.06 mmol) and DIPEA (18.6 mg, 0.14 mmol) were added. It was allowed to react at room temperature for 2 h. Water was added to the reaction solution and the resulting mixture was extracted twice with ethyl acetate. The organic phases were combined, washed with saturated saline, dried over anhydrous sodium sulfate, concentrated and purified on silica gel plate to obtain the final product of 6 mg in a yield of 22.6%.

$^1H$ NMR (400 MHz, $CD_3OD$) δ 8.46 (s, 2H), 7.66 (d, J=4 Hz, 1H), 7.45 (d, J=8 Hz, 1H), 7.17 (d, J=8 Hz, 1H), 6.17-6.22 (m, 1H), 4.65-4.80 (m, 4H), 3.59 (s, 2H), 3.25-3.29 (m, 1H), 3.10-3.14 (m, 1H), 2.92-3.03 (m, 2H), 2.82-2.88 (m, 1H), 2.32-2.41 (m, 1H), 2.11-2.19 (m, 1H), 1.83 (d, J=4 Hz, 3H).

Examples 33-35

The compounds of Examples 33 to 35 shown in the table below were prepared according to the synthetic route of Example 1, using suitable starting materials.

| Compound of Examples | $^1$HNMR (400 MHz) | LC-MS Theoretical Calculated values $(M + 1)^+$ | LC-MS Measured values $(M + 1)^+$ |
|---|---|---|---|
| 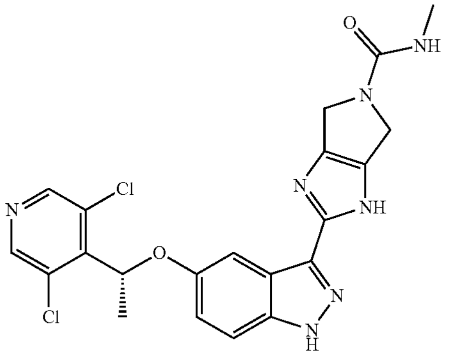 33 (R)-2-(5-(1-(3,5-dichloropyridin-4-yl)ethoxy)-1H-indazol-3-yl)-N-methyl-4,6-dihydropyrrolo[3,4-d]imidazole-5(1H)-carboxamide | ($CD_3OD$) δ 8.45 (s, 2H), 7.65 (d, J = 4.0 Hz, 1H), 7.46 (d, J = 8.0 Hz, 1H), 7.18 (dd, J = 4.0 Hz, J = 8.0 Hz, 1H), 6.20 (dd, J = 12.0 Hz, J = 8.0 Hz, 1H), 4.54 (s, 4H), 2.85 (s, 3H), 1.84 (d, J = 8.0 Hz, 3H). | | |
| 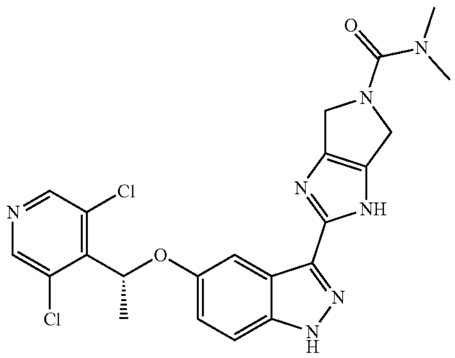 34 (R)-2-(5-(1-(3,5-dichloropyridin-4-yl)ethoxy)-1H-indazol-3-yl)-N,N-dimethyl-4,6-dihydropyrrolo[3,4-d]imidazole-5(1H)-carboxamide | | 486.1 | 486.1 |

-continued

| Compound of Examples | $^1$HNMR (400 MHz) | LC-MS Theoretical Calculated values $(M + 1)^+$ | LC-MS Measured values $(M + 1)^+$ |
|---|---|---|---|
| 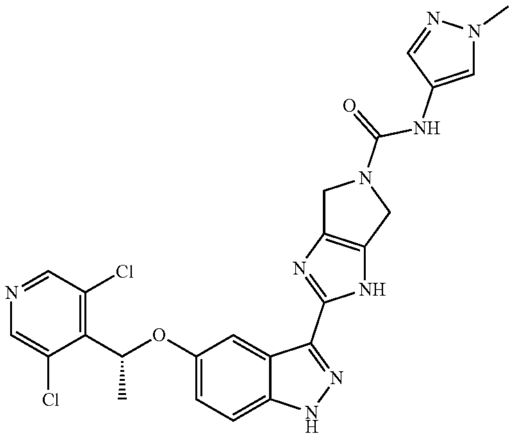<br>35<br>(R)-2-(5-(1-(3,5-dichloropyridin-4-yl)ethoxy)-1H-indazol-3-yl)-N-(1-methyl-1H-pyrazol-4-yl)-4,6-dihydropyrrolo[3,4-d]imidazole-5(1H)-carboxamide | | 538.1 | 538.1 |

Examples 36-39

The compounds of Examples 36 to 39 shown in the table below were prepared according to the synthetic route of Example 3, using suitable starting materials.

| Compound of Examples | $^1$HNMR (400 MHz) | LC-MS Theoretical Calculated values $(M + 1)^+$ | LC-MS Measured values $(M + 1)^+$ |
|---|---|---|---|
| 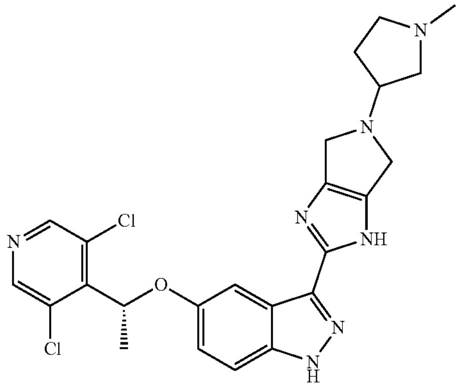<br>36<br>5-((R)-1-(3,5-Dichloropyridin-4-yl)ethoxy)-3-(5-(1-methylpyrrolidin-3-yl)-1,4,5,6-tetrahydropyrrolo[3,4-d]imidazol-2-yl)-1H-indazole | $(CD_3OD)$ δ 8.45 (s, 2H), 7.62 (d, J = 4.0 Hz, 1H), 7.47 (d, J = 12.0 Hz, 1H), 7.17 (d, J = 10.0 Hz, 1H), 6.17-6.22 (m, 1H), 4.04-4.10 (m, 4H), 3.83-3.85 (m, 1H), 3.60-3.65 (m, 2H), 3.30-3.32 (m, 2H), 3.03 (s, 3H), 2.35-2.41 (m, 2H), 1.83 (d, J = 8.0 Hz, 3H). | | |

-continued

| Compound of Examples | $^1$HNMR (400 MHz) | LC-MS Theoretical Calculated values $(M + 1)^+$ | LC-MS Measured values $(M + 1)^+$ |
|---|---|---|---|
| 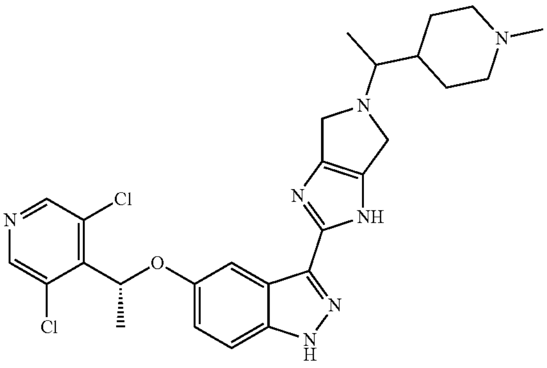 37 5-((R)-1-(3,5-Dichloropyridin-4-yl)ethoxy)-3-(5-(1-(1-methylpiperidin-4-yl)ethyl)-1,4,5,6-tetrahydropyrrolo[3,4-d]imidazol-2-yl)-1H-indazole | (CD3OD) δ 8.46 (s, 2H), 7.64 (d, J = 4.0 Hz, 1H), 7.47 (d, J = 8.0 Hz, 1H), 7.17 (dd, J = 8.0 Hz, J = 8.0 Hz, 1H), 6.20-6.15 (m, 1H), 4.41 (s, 4H), 3.63-3.59 (m, 2H), 3.20-3.13 (m, 2H), 2.91 (s, 3H), 2.18-2.11 (m, 3H), 1.84-1.79 (m, 5H), 1.35-1.30 (m, 4H). | | |
| 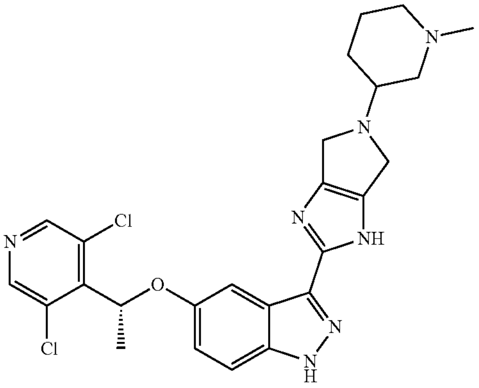 38 5-((R)-1-(3,5-Dichloropyridin-4-yl)ethoxy)-3-(5-(1-methylpiperidin-3-yl)-1,4,5,6-tetrahydropyrrolo[3,4-d]imidazol-2-yl)-1H-indazole | (CD3OD) δ 8.45 (s, 2H), 7.64 (d, J = 4.0 Hz, 1H), 7.46 (d, J = 12.0 Hz, 1H), 7.17 (d, J = 8.0 Hz, J = 4.0 Hz, 1H), 6.21-6.16 (m, 1H), 4.06-3.97 (m, 4H), 3.34-3.32 (m, 2H), 3.11-3.09 (m, 2H), 2.71 (s, 3H), 2.05-2.03 (m, 2H), 1.84-1.82 (m, 4H), 1.35-1.30 (m, 2H). | | |
| 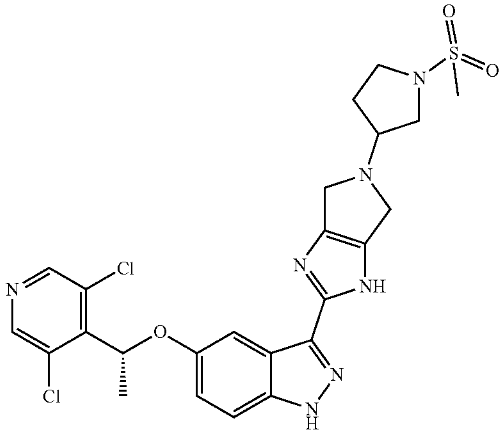 39 | (CD3OD) δ 8.45 (s, 2H), 7.64 (d, J = 2.0 Hz, 1H), 7.44 (d, J = 8.0 Hz, 1H), 7.16 (d, J = 8.0 Hz, 1H), 6.17-6.22 (m, 1H), 3.99-4.03 (m, 4H), 3.55-3.68 (m, 4H), 3.39-3.45 (m, 1H), 2.96 (s, 3H), 2.28-2.32 (m, 1H), 2.06-2.12 (m, 1H), 1.83 (d, J = 8.0 Hz, 3H). | | |

-continued

| Compound of Examples | ¹HNMR (400 MHz) | LC-MS Theoretical Calculated values (M + 1)⁺ | LC-MS Measured values (M + 1)⁺ |
|---|---|---|---|
| 5-((R)-1-(3,5-Dichloropyridin-4-yl)ethoxy)-3-(5-(1-(methylsulfonyl)pyrrolidin-3-yl)-1,4,5,6-tetrahydropyrrolo[3,4-d]imidazol-2-yl)-1H-indazole | | | |

Examples 40-53

The compounds of Examples 40 to 53 shown in the table below were prepared according to the synthetic route of Example 6, using suitable starting materials.

| Compound of Examples | ¹HNMR (400 MHz) | LC-MS Theoretical Calculated values (M + 1)⁺ | LC-MS Measured values (M + 1)⁺ |
|---|---|---|---|
| 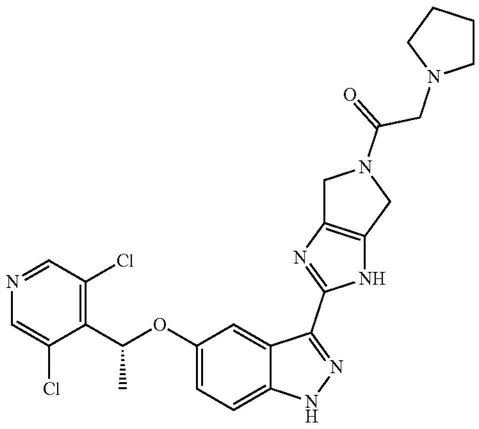 40 (R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(pyrrolidin-1-yl)ethan-1-one | | 526.1 | 526.1 |
| 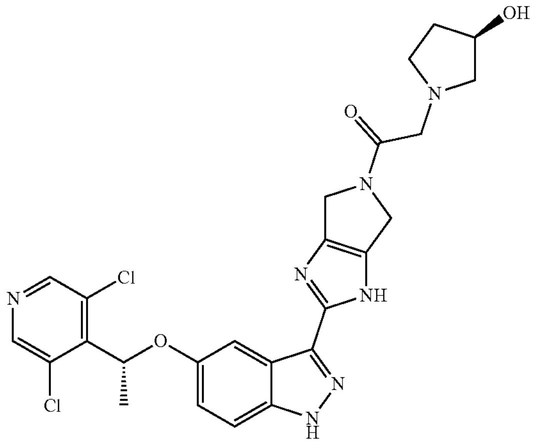 41 | ($CD_3OD$) δ 8.46 (s, 2H), 7.65 (d, J = 4.0 Hz, 1H), 7.47 (d, J = 12.0 Hz, 1H), 7.18 (dd, J = 4.0 Hz, J = 8.0 Hz, 1H), 6.19 (dd, J = 12.0 Hz, J = 8.0 Hz, 1H), 4.76-4.68 (m, 4H), 4.51 (s, 1H), 4.01 (s, 2H), 3.26-3.24 (m, 2H), 3.19-3.11 (m, 2H), 2.29-2.24 (m, 1H), 1.99-1.97 (m, 1H), 1.84 (d, J = 8.0 Hz, 3H). | | |

-continued

| Compound of Examples | $^1$HNMR (400 MHz) | LC-MS Theoretical Calculated values $(M + 1)^+$ | LC-MS Measured values $(M + 1)^+$ |
|---|---|---|---|
| 1-(2-(5-((R)-1-(3,5-Dichloropyridin-4-yl)ethoxy)-1H-indazol-3-yl)-4,6-dihydropyrrolo[3,4-d]imidazol-5(1H)-yl)-2-((R)-3-hydroxypyrrolidin-1-yl)ethan-1-one | | | |
| 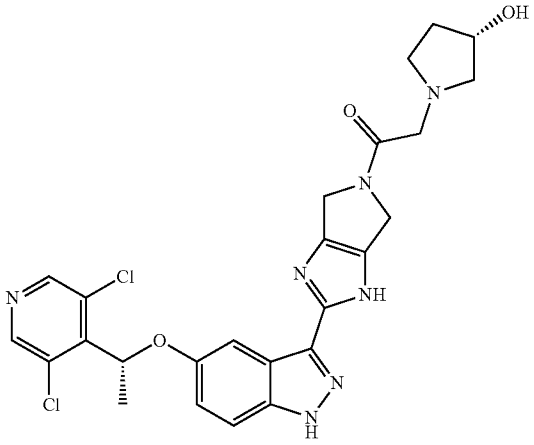 | $(CD_3OD)$ δ 8.46 (s, 2H), 7.65 (d, J = 4.0 Hz, 1H), 7.45 (d, J = 10.0 Hz, 1H), 7.17 (d, J = 8.0 Hz, 1H), 6.16-6.21 (m, 1H), 4.66-4.77 (m, 4H), 4.48-4.51 (m, 1H), 3.98 (s, 2H), 3.30-3.32 (m, 2H), 3.08-3.15 (m, 2H), 2.21-2.28 (m, 1H), 1.93-1.99 (m, 1H), 1.83 (d, J = 4.0 Hz, 3H). | | |
| 42 | | | |
| 1-(2-(5-((R)-1-(3,5-Dichloropyridin-4-yl)ethoxy)-1H-indazol-3-yl)-4,6-dihydropyrrolo[3,4-d]imidazol-5(1H)-yl)-2-((S)-3-hydroxypyrrolidin-1-yl)ethan-1-one | | | |
| 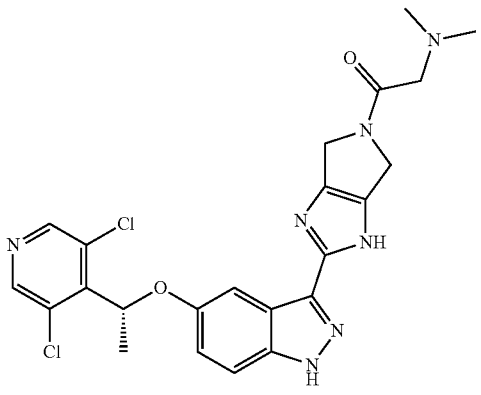 | $(CD_3OD)$ δ 8.46 (s, 2H), 7.65 (d, J = 4.0 Hz, 1H), 7.47 (d, J = 12.0 Hz, 1H), 7.18 (dd, J = 4.0 Hz, J = 8.0 Hz, 1H), 6.20 (dd, J = 12.0 Hz, J = 8.0 Hz, 1H), 4.76-4.68 (m, 4H), 3.77 (s, 2H), 2.67 (s, 6H), 1.84 (d, J = 4.0 Hz, 3H). | | |
| 43 | | | |
| (R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(dimethylamino)ethan-1-one | | | |

-continued
| Compound of Examples | $^1$HNMR (400 MHz) | LC-MS Theoretical Calculated values $(M + 1)^+$ | LC-MS Measured values $(M + 1)^+$ |
|---|---|---|---|
| 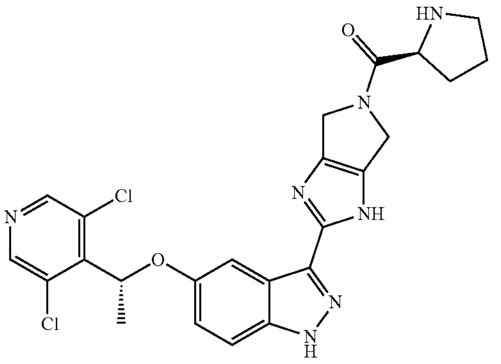 44 3-(5-(L-prolinyl)-1,4,5,6-tetrahydropyrrolo[3,4-d]imidazol-2-yl)-5-((R)-1-(3,5-dichloropyridin-4-yl)ethoxy)-1H-indazole | | 512.1 | 512.1 |
| 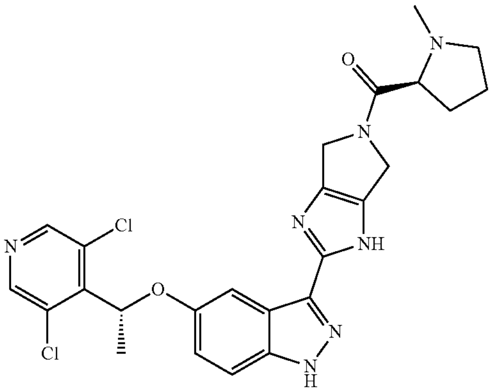 45 5-((R)-1-(3,5-dichloropyridin-4-yl)ethoxy)-3-(5-(methyl-L-prolinyl)-1,4,5,6-tetrahydropyrrolo[3,4-d]imidazol-2-yl)-1H-indazole | | 526.1 | 526.1 |
| 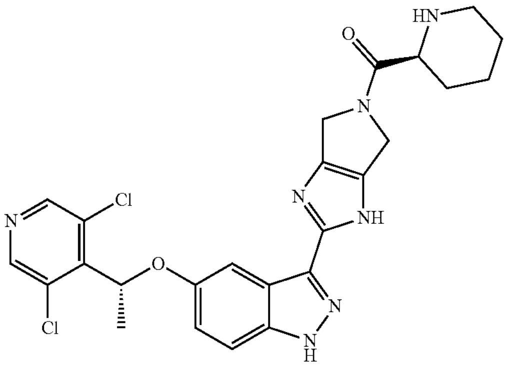 46 | | 526.1 | 526.1 |

-continued

| Compound of Examples | $^{1}$HNMR (400 MHz) | LC-MS Theoretical Calculated values $(M + 1)^+$ | LC-MS Measured values $(M + 1)^+$ |
|---|---|---|---|
| (2-(5-((R)-1-(3,5-dichloropyridin-4-yl)ethoxy)-1H-indazol-3-yl)-4,6-dihydropyrrolo[3,4-d]imidazol-5(1H)-yl)((S)-piperidin-2-yl)ketone | | | |
| 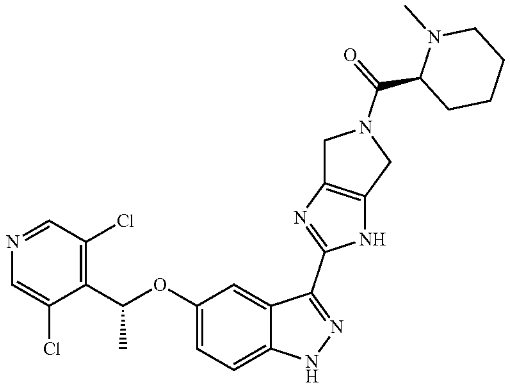 47 (2-(5-((R)-1-(3,5-dichloropyridin-4-yl)ethoxy)-1H-indazol-3-yl)-4,6-dihydropyrrolo[3,4-d]imidazol-5(1H)-yl)((S)-1-methylpiperidin-2-yl)ketone | | 540.1 | 540.1 |
| 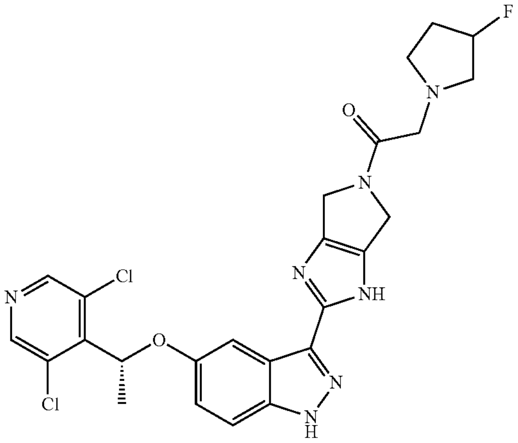 48 1-(2-(5-((R)-1-(3,5-Dichloropyridin-4-yl)ethoxy)-1H-indazol-3-yl)-4,6-dihydropyrrolo[3,4-d]imidazol-5(1H)-yl)-2-(3-fluoropyrrolidin-1-yl)ethan-1-one | ($CD_3OD$) δ 8.44 (s, 2H), 7.63 (d, J = 4.0 Hz, 1H), 7.42 (d, J = 10.0 Hz, 1H), 7.14 (d, J = 10.0 Hz, 1H), 6.14-6.19 (m, 1H), 4.62-4.77 (m, 4H), 3.58-3.63 (m, 3H), 3.01-3.22 (m, 2H), 2.73-2.76 (m, 1H), 2.02-2.25 (m, 3H), 1.81 (d, J = 8.0 Hz, 3H). | | |

-continued

| Compound of Examples | $^1$HNMR (400 MHz) | LC-MS Theoretical Calculated values $(M + 1)^+$ | LC-MS Measured values $(M + 1)^+$ |
|---|---|---|---|
| 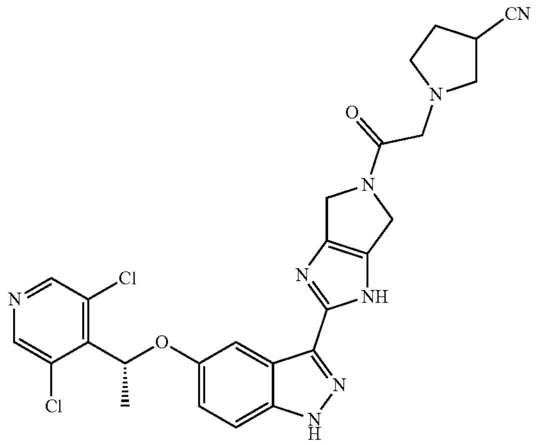 49 1-(2-(2-(5-((R)-1-(3,5-dichloropyridin-4-yl)ethoxy)-1H-indazol-3-yl)-4,6-dihydropyrrolo[3,4-d]imidazol-5(1H)-yl)-2-oxoethyl)pyrrolidine-3-carbonitrile | $(CD_3OD)$ δ 8.46 (s, 2H), 7.66 (s, 1H), 7.45 (d, J = 8 Hz, 1H), 7.17 (d, J = 8 Hz, 1H), 6.17-6.22 (m, 1H), 4.62-4.80 (m, 4H), 3.66 (s, 2H), 3.25-3.29 (m, 1H), 3.19-3.22 (m, 1H), 3.01-3.11 (m, 2H), 2.91-2.94 (m, 1H), 2.33-2.38 (m, 1H), 2.15-2.18 (m, 1H), 1.83 (d, J = 4 Hz, 3H). | | |
| 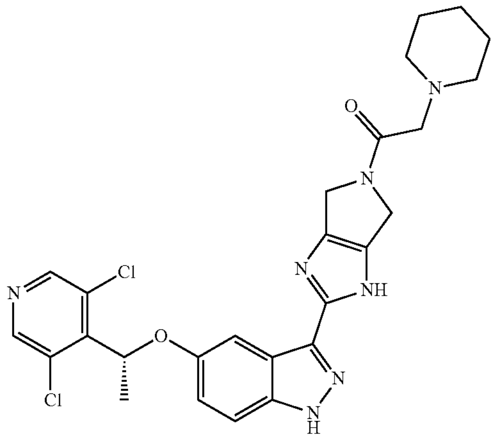 50 (R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(piperidin-1-yl)ethan-1-one | $(CD_3OD)$ δ 8.45 (s, 2H), 7.64 (d, J = 4.0 Hz, 1H), 7.46 (d, J = 8.0 Hz, 1H), 7.16 (d, J = 8.0 Hz, 1H), 6.14-6.19 (m, 1H), 4.69-4.76 (m, 4H), 4.26 (s, 2H), 3.34-3.40 (m, 4H), 1.92-1.98 (m, 4H), 1.82 (d, J = 8.0 Hz, 3H), 1.72-1.75 (m, 2H). | | |

-continued

| Compound of Examples | $^{1}$HNMR (400 MHz) | LC-MS Theoretical Calculated values $(M + 1)^+$ | LC-MS Measured values $(M + 1)^+$ |
|---|---|---|---|
| 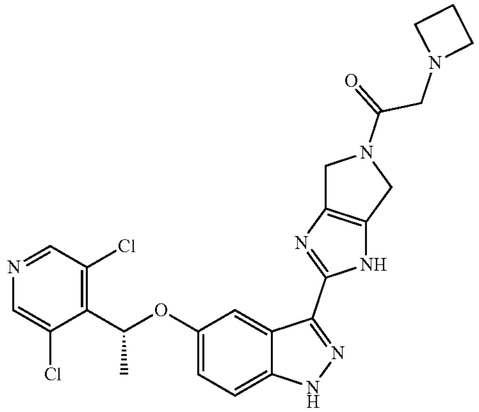 51 (R)-2-(Azetidin-1-yl)-1-(2-(5-(1-(3,5-dichloropyridin-4-yl)ethoxy)-1H-indazol-3-yl)-4,6-dihydropyrrolo[3,4-d]imidazol-5(1H)-yl)ethan-1-one | ($CD_3OD$) δ 8.45 (s, 2H), 7.65 (d, J = 4.0 Hz, 1H), 7.47 (d, J = 8.0 Hz, 1H), 7.17 (dd, J = 4.0 Hz, J = 8.0 Hz, 1H), 6.19-6.17 (m, 1H), 4.73-4.67 (m, 4H), 4.44 (s, 2H), 4.33-4.29 (m, 4H), 2.63-2.59 (m, 2H), 1.84 (d, J = 8.0 Hz, 3H). | | |
| 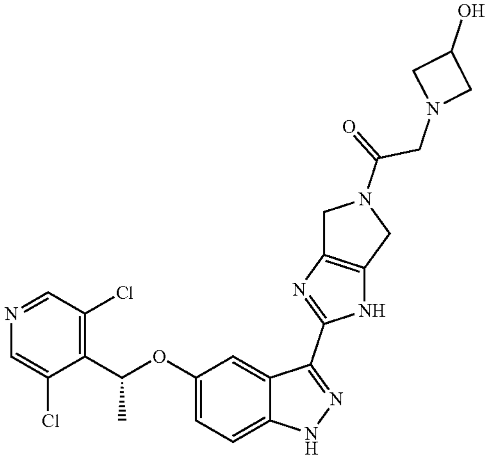 52 (R)-1-(2-(5-(1-(3,5-Dichloropyridin-4-yl)ethoxy)-1H-indazol-3-yl)-4,6-dihydropyrrolo[3,4-d]imidazol-5(1H)-yl)-2-(3-hydroxyazetidin-1-yl)ethan-1-one | ($CD_3OD$) δ 8.46 (s, 2H), 7.65 (d, J = 2.0 Hz, 1H), 7.46 (d, J = 10.0 Hz, 1H), 7.17 (d, J = 8.0 Hz, 1H), 6.16-6.21 (m, 1H), 4.64-4.72 (m, 4H), 4.57-4.61 (m, 1H), 4.17-4.21 (m, 2H), 4.00 (s, 2H), 3.59-3.63 (m, 2H), 1.83 (d, J = 4.0 Hz, 3H). | | |

-continued

| Compound of Examples | $^1$HNMR (400 MHz) | LC-MS Theoretical Calculated values $(M + 1)^+$ | LC-MS Measured values $(M + 1)^+$ |
|---|---|---|---|
| 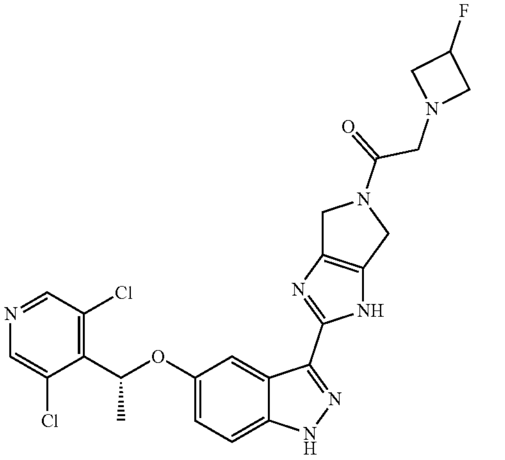 53 (R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(3-fluoroazetidin-1-yl)ethan-1-one | $(CD_3OD)$ δ 8.43 (s, 2H), 7.63 (d, J = 4.0 Hz, 1H), 7.43 (d, J = 8.0 Hz, 1H), 7.15 (d, J = 8.0 Hz, 1H), 6.14-6.19 (m, 1H), 4.62-4.70 (m, 4H), 4.20-4.29 (m, 2H), 3.98-4.04 (m, 2H), 3.63 (s, 2H), 3.47-3.48 (m, 1H), 1.82 (d, J = 4.0 Hz, 3H). | | |

Examples 54-55

The compounds of Examples 54 to 55 shown in the table below were prepared according to the synthetic route of Example 17 using suitable starting materials.

| Compound of Examples | $^1$HNMR (400 MHz) | LC-MS Theoretical Calculated values $(M + 1)^+$ | LC-MS Measured values $(M + 1)^+$ |
|---|---|---|---|
| 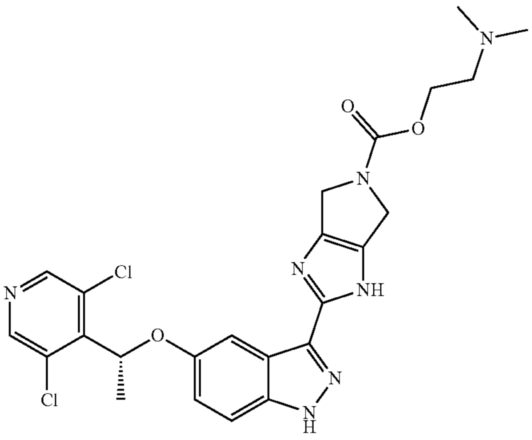 54 2-(dimethylamino)ethyl(R)-2-(5-(1-(3,5-dichloropyridin-4-yl)ethoxy)-1H-indazol-3-yl)-4,6-dihydropyrrolo[3,4-d]imidazole-5(1H)-carboxylate | | 530.1 | 530.1 |

-continued

| Compound of Examples | $^1$HNMR (400 MHz) | LC-MS Theoretical Calculated values $(M + 1)^+$ | LC-MS Measured values $(M + 1)^+$ |
|---|---|---|---|
| 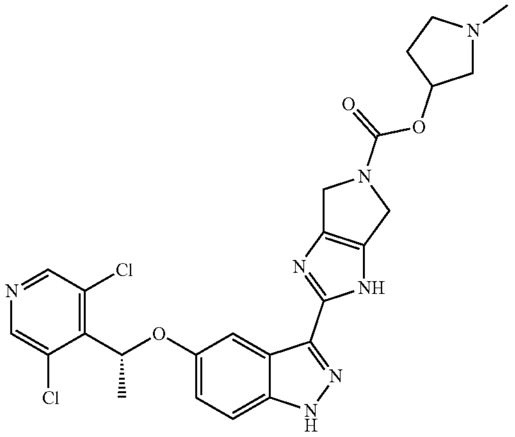<br>55<br>1-Methylpyrrolidin-3-yl 2-(5-((R)-1-(3,5-dichloropyridin-4-yl)ethoxy)-1H-indazol-3-yl)-4,6-dihydropyrrolo[3,4-d]imidazole-5(1H)-carboxylate | | 542.1 | 542.1 |

Assay I: Determination of Inhibitory Activity Against FGFR Mutants

1. Reagents and Equipment

| Materials and reagents | Manufacturer | Cat. No. |
|---|---|---|
| HTRF KinEASE-TK kit | Cisbio | 62TK0PEC |
| FGFR1 V561M | Signalchem | F04-13G |
| FGFR2 V564F | Signalchem | F05-12FG |
| VEGFR2 | Carna | 08-191 |
| FGFR3 V555M | Signalchem | F06-12GG |
| MgCl2 | Sigma | M1028 |
| ATP | Promega | V910B |
| DTT | Sigma | D0632 |
| DMSO | Sigma | D8418-1L |
| Infigratinib (NVP-BGJ398) | MCE | HY-13311 |

| Instruments and Equipment | Manufacturer | Cat. No. or Model No. |
|---|---|---|
| 384-well plate, white, low volume, round-bottom | Greiner | Sep. 20, 4046 |
| 96-well polypropylene plate | Nunc | Apr. 26, 2584 |
| Microplate low-speed centrifuge | Xiang Zhi | TD5B |
| Biotek Enzyme Labeler | Biotek | Synergy 4 |

2. Experimental Steps 2.1 Preparation of 1× Kinase Reaction Buffer:

1× Kinase reaction buffer was formulated with 1× volume of 5× kinase reaction buffer and 4× volume of water; 5 mM $MgCl_2$; and 1 mM DTT.

2.2 Reaction Conditions

| Kinase | ATP Km [μM] | ATP working concentration [μM] | Substrate TK [μM] |
|---|---|---|---|
| FGFR1 V561M | 4.24 | 5 | 1 |
| FGFR2 V564F | 13.81 | 10 | 1 |
| FGFR3 V555M | 18.02 | 20 | 1 |
| VEGFR2 | 5.92 | 5 | 1 |

2.3 Screening of Compounds:

1. Diluting a compound 4-fold in a dilution plate with DMSO, with a starting compound concentration of 2 mM.

2. Diluting the compound 40-fold into 1× kinase reaction buffer and shaking it on a shaker for 20 minutes.

3. Formulating 2×FGFR1 V561M/FGFR2 V564F/FGFR3 K650E/VEGFR2 with 1× of enzyme reaction buffer.

4. Adding 2 μl FGFR1 V561M/FGFR2 V564F/FGFR3 K650E/VEGFR2 kinase (formulated in step 3) to each well of the reaction plate.

5. Adding 1 μl of the compound diluted in buffer to each well, sealing the plate with a sealing membrane and centrifuging the plate at 1000 g for 30 seconds and leaving it at room temperature for 10 minutes.

6. Formulating 2.5×TK-substrate-biotin and ATP mixture with 1× enzyme reaction buffer and adding 2 μl of K-substrate-biotin/ATP mixture to the reaction plate.

7. Sealing the plate with a sealing membrane and centrifuging the plate at 1000 g for 30 seconds and allowing it to react at room temperature for 50 minutes.

8. Formulating 4× Sa-XL 665 (250 nM) with HTRF assay buffer.

9. Adding 5 μl Sa-XL 665 and 5 μl TK-Antibody-Cryptate to each well, centrifuging it at 1000 g for 30 seconds, and allowing it to react for 1 hour at room temperature.

10. Reading fluorescence signals at 615 nm (Cryptate) and 665 nm (XL665) with Biotek.

3. Data Analysis 3.1 Calculation of the ratio for each well: the ratio was calculated as 665/615 nm.

3.2 The inhibition rate was calculated as follows: inhibition rate of compound (% inh)=100%−(compound−positive control)/(negative control−positive control)*100%. The positive control was 10,000 nM Infigratinib, and the negative control was 0.5% DMSO.

3.3 Calculation of IC50 and plotting of inhibition curves for the compounds.

The IC50 (half inhibition concentration) of a compound was obtained using the following non-linear fitting equation, wherein data analysis was performed using Graphpad 6.0 software.

$$Y = \text{Bottom} + (\text{Top} - \text{Bottom})/(1 + 10\string^((\text{Log}IC50 - X) * \text{Hill Slope}))$$

X: log value of compound concentration; and Y: inhibition rate (% inh)

3.4 Validation of results

Data were exported from Envision and analyzed manually. The ratios were converted to inhibition rates and IC50 was calculated by Prism GraphPad 6.0 from the inhibition rates. IC50 was calculated again by the ratios to verify accuracy of the results.

3.5 Quality control

Z-factor>0.5; and S/B>2

Positive control IC50 was within 3 times of the average value

4. Results

TABLE 1

Inhibition of FGFR mutants by compounds

| Compounds | IC50 (nM) FGFR1 V561M | FGFR2 V564F | FGFR3 V555M | VEGFR2 |
|---|---|---|---|---|
| Infigratinib | 10.1 | 485 | 77 | 99 |
| 1 | 0.26 | 0.34 | 0.34 | 1 |
| 2 | 0.21 | 0.1 | 0.05 | 2.6 |
| 3 | 0.65 | 0.25 | 0.67 | 5.4 |
| 4 | 0.31 | 0.19 | 0.16 | 17.6 |
| 5 | 0.58 | 0.36 | 0.23 | 0.75 |
| 6 | 0.38 | 0.11 | 0.12 | 3.1 |
| 7 | 1.6 | 3.1 | 4.0 | 42.9 |
| 8 | 0.33 | 0.36 | 0.45 | 2.1 |
| 9 | 0.41 | 0.27 | 0.16 | 5.6 |
| 10 | 0.2 | 0.33 | 0.35 | 2.4 |
| 11 | 0.46 | 1.3 | 1.1 | 25.6 |
| 12 | 1.2 | 0.29 | 0.21 | 14.2 |
| 13 | 0.46 | 0.31 | 0.22 | 5.5 |
| 14 | 0.11 | 0.09 | 0.03 | 6.1 |
| 15 | 3.6 | 2.0 | 2.0 | 67 |
| 16 | 0.39 | 0.22 | 0.35 | 22.1 |
| 17 | 1.2 | 0.74 | 0.21 | 49 |
| 18 | 2.2 | 1.2 | NA | 19.6 |
| 19 | 0.6 | 0.59 | 0.76 | 31 |
| 20 | 1.8 | 1.7 | NA | 13.3 |
| 21 | 0.97 | 0.66 | 0.64 | 26 |
| 22 | 1.8 | 0.76 | 0.91 | 11.7 |
| 23 | 1.2 | 0.48 | 1.3 | 85 |
| 24 | 2.4 | 1.4 | 4.6 | 27.5 |

TABLE 1-continued

Inhibition of FGFR mutants by compounds

| Compounds | IC50 (nM) FGFR1 V561M | FGFR2 V564F | FGFR3 V555M | VEGFR2 |
|---|---|---|---|---|
| 25 | 0.98 | 0.41 | 0.26 | 10 |
| 26 | 0.38 | 0.17 | 0.13 | 7.1 |
| 27 | 0.94 | 0.16 | 0.40 | 37.5 |
| 28 | 1.6 | 0.3 | 0.52 | 30 |
| 29 | 1.2 | 1.6 | 0.7 | 64 |
| 30 | 0.4 | 0.3 | 0.6 | 96 |
| 31 | 0.67 | 0.15 | 0.10 | 14 |
| 32 | 1.1 | 1.2 | 0.19 | 3.7 |
| 33 | 1.3 | 0.45 | 0.46 | 6.3 |
| 34 | 0.46 | 0.29 | 0.27 | 1.7 |
| 36 | 1.9 | 0.61 | 0.31 | 27.5 |
| 37 | 3.9 | 0.68 | 0.58 | 49.3 |
| 38 | 0.75 | 0.19 | 0.15 | 15.7 |
| 39 | NA | 1.3 | 1.4 | 60.5 |
| 40 | 0.39 | 0.32 | 0.26 | 4.7 |
| 41 | 0.26 | 0.23 | 0.10 | 2.4 |
| 42 | 1.0 | 0.18 | 0.33 | 10.3 |
| 43 | 0.26 | 0.13 | 0.35 | 3.3 |
| 44 | 0.82 | 0.32 | 0.43 | 5.3 |
| 45 | 0.81 | 0.36 | 0.18 | 7.6 |
| 46 | 0.65 | 0.29 | 0.33 | 9.9 |
| 47 | 0.29 | 0.21 | 0.14 | 2.5 |
| 48 | NA | 0.084 | 0.33 | 11.1 |
| 49 | NA | 0.017 | 0.19 | 6.7 |
| 50 | 1.2 | 0.21 | 0.35 | 8.4 |
| 51 | 0.74 | 0.21 | 0.16 | 14.2 |
| 52 | 0.87 | 0.16 | 0.14 | 13.6 |
| 53 | 6.4 | 0.82 | 1.9 | 45.5 |
| 54 | 0.55 | 0.15 | 0.11 | 3.3 |
| 55 | 5.1 | 0.34 | 0.87 | 13.4 |

Each example compound showed good inhibitory activity against FGFR1 V561M, FGFR2 V564F, and FGFR3 V555M, while exhibiting relatively weak inhibitory activity against VEGFR2.

Assay II: Determination of Inhibitory Activity Against Wild-Type FGFR

1. Reagents and Equipment

| Materials and reagents | Manufacturer | Cat. No. |
|---|---|---|
| HTRF KinEASE-TK kit | Cisbio | 62TK0PEC |
| FGFR1 | Carna | 08-133 |
| FGFR2 | Carna | 08-134 |
| FGFR3 | Carna | 08-135 |
| MgCl2 | Sigma | M1028 |
| ATP | Promega | V910B |
| DTT | Sigma | D0632 |
| DMSO | Sigma | D8418-1L |
| Infigratinib (NVP-BGJ398) | MCE | HY-13311 |
| **Instruments and Equipment** | **Manufacturer** | **Cat. No. or Model No.** |
| 384-well plate, white, low volume, round-bottom | Greiner | Sep. 20, 4046 |
| 96-well polypropylene plate | Nunc | Apr. 26, 2584 |
| Microplate low-speed centrifuge | Xiang Zhi | TD5B |
| Biotek Enzyme Labeler | Biotek | Synergy 4 |

2. Experimental Steps PGP-5T 2.1 Preparation of 1× Kinase Reaction Buffer:

1× Kinase reaction buffer was formulated with 1× volume of 5× kinase reaction buffer and 4× volume of water; 5 mM $MgCl_2$; and 1 mM DTT.

2.2 Reaction Conditions

| Kinase | ATP Km [μM] | ATP working concentration [μM] | Substrate TK [μM] |
|---|---|---|---|
| FGFR1 | 28.3 | 50 | 1 |
| FGFR2 | 36.47 | 50 | 1 |
| FGFR3 | 67.28 | 50 | 1 |

2.3 Screening of Compounds:

1. Diluting a compound 4-fold in a dilution plate with DMSO, with a starting compound concentration of 2 mM.

2. Diluting the compound 40-fold into 1× kinase reaction buffer and shaking it on a shaker for 20 minutes.

3. Formulating 2×FGFR1/FGFR2/FGFR3 with 1× of enzyme reaction buffer.

4. Adding 2 μl FGFR1/FGFR2/FGFR3 kinase (formulated in step 3) to each well of the reaction plate.

5. Adding 1 μl of the compound diluted in buffer to each well, sealing the plate with a sealing membrane and centrifuging the plate at 1000 g for 30 seconds and leaving it at room temperature for 10 minutes.

6. Formulating 2.5×TK-substrate-biotin and ATP mixture with 1× enzyme reaction buffer and add 2 μl of K-substrate-biotin/ATP mixture to the reaction plate.

7. Sealing the plate with a sealing membrane and centrifuging the plate at 1000 g for 30 seconds and allowing it to react at room temperature for 50 minutes.

8. Formulating 4× Sa-XL 665 (250 nM) with HTRF assay buffer.

9. Adding 5 μl Sa-XL 665 and 5 μl TK-Antibody-Cryptate to each well, centrifuging it at 1000 g for 30 seconds, and allowing it to react for 1 hour at room temperature.

10. Reading fluorescence signals at 615 nm (Cryptate) and 665 nm (XL665) with Biotek.

3. Data Analysis 3.1 Calculation of the ratio for each well: the ratio was calculated as 665/615 nm.

3.2 The inhibition rate was calculated as follows: inhibition rate of compound (% inh)=100%−(compound−positive control)/(negative control−positive control)*100%. The positive control was 10,000 nM Infigratinib, and the negative control was 0.5% DMSO.

3.3 Calculation of IC50 and plotting of inhibition curves for the compounds.

The IC50 (half inhibition concentration) of a compound was obtained using the following non-linear fitting equation, wherein data analysis was performed using Graphpad 6.0 software.

$$Y = \text{Bottom} + (\text{Top} - \text{Bottom})/(1 + 10\text{^}((\text{Log}IC50 - X) * \text{Hill Slope}))$$

X: log value of compound concentration; and Y: inhibition rate (% inh)

3.4 Validation of results

Data were exported from Envision and analyzed manually. The ratios were converted to inhibition rates and IC50 was calculated by Prism GraphPad 6.0 from the inhibition rates. IC50 was calculated again by the ratios to verify accuracy of the results.

3.5 Quality control

Z-factor>0.5; and S/B>2

Positive control IC50 was within 3 times of the average value

4. Results

TABLE 2

Inhibition of wild FGFR by compounds

| Compounds | $IC_{50}$ (nM) FGFR1 | FGFR2 | FGFR3 |
|---|---|---|---|
| Infigratinib | 0.38 | 1.2 | 2.3 |
| 1 | 2.7 | 2.9 | 4.1 |
| 5 | 1.8 | 2.1 | 3.8 |
| 8 | 4.1 | 2.8 | 4.5 |
| 10 | 3.1 | 2.2 | 3.4 |
| 11 | 1.7 | 0.95 | 0.6 |

Each tested compound showed similar or better inhibitory activity against wild-type FGFR1/FGFR2/FGFR3 compared with Infigratinib.

Although specific embodiments of the present disclosure have been illustrated and described, it does not mean that these embodiments illustrate and describe all possible implementation forms of the present disclosure. More precisely, the language used in this specification are only descriptive words and not restrictive. It will be obvious to those skilled in the art that various kinds of changes and modifications can be made without departing from the general scope of the present disclosure. Therefore, the appended claims are intended to include all these changes and modifications within the scope of the present disclosure.

What is claimed is:

1. A compound of Formula (I),

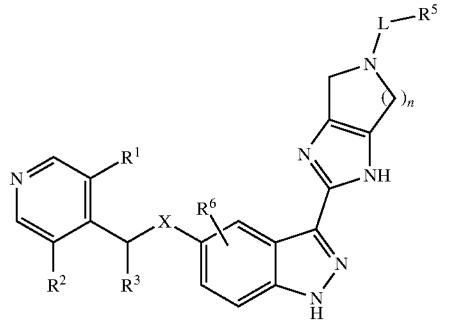

(I)

or an optical isomer thereof, a geometric isomer thereof, a tautomer thereof or a mixture of various isomers, or a pharmaceutically acceptable salt thereof, wherein $R^1$ and $R^2$ are each independently selected from H, halogen, —CN, OH, —$NO_2$, —$NR^7R^8$, $C_{1-4}$ alkyl, $C_{1-4}$ haloalkyl, $C_{1-4}$ alkoxy, $C_{3-6}$ alicyclic group, and 4-6 membered heteroalicyclic group; and $R^3$ is selected from H, $C_{1-4}$ alkyl, $C_{1-4}$ haloalkyl, $C_{1-4}$ alkoxy, $C_{3-6}$ alicyclic group, and 4-6 membered heteroalicyclic group; and 1, 2 or 3 $R^6$(s) are present in formula (I), and each $R^6$ is independently selected from H, halogen, —CN, —OH, —$NO_2$, —$NR^7R^8$, $C_{1-4}$ alkyl, $C_{1-4}$ haloalkyl, $C_{1-4}$ alkoxy, $C_{3-6}$ alicyclic group, and 4-6 membered heteroalicyclic group; and X is O, S or ($NR^4$) in which $R^4$ is selected from H, $C_{1-4}$ alkyl, $C_{1-4}$ haloalkyl, $C_{1-4}$ alkoxy, $C_{3-6}$ alicyclic group, and 4-6 membered heteroalicyclic group; and $R^7$ and $R^8$, at each occurrence, are each independently selected from H, $C_{1-6}$ alkyl, $C_{1-4}$ haloalkyl, and $C_{1-4}$ alkoxy, or $R^7$ and $R^8$ and the atom(s) attached thereto together form a 3-6-membered ring; and n=1, 2 or 3; and L is (C=O), (O=S=O), ((C=O)—$CH_2$) or a bond; and $R^5$ is selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ alicyclic group, 3-10 membered heteroalicyclic group, $C_{6-12}$ bicyclic alicyclic group, 6-12 membered bicyclic heteroalicyclic group, $C_{8-15}$ tricyclic alicyclic group, 8-15 membered tricyclic heteroalicyclic group, $C_{5-8}$ aryl, 5-10 membered heteroaryl, $C_{7-11}$ bicyclic aryl, 7-11 membered bicyclic heteroaryl, —$C_{1-4}$ alkyl-($C_{3-7}$ alicyclic group), —$C_{1-4}$ alkyl-(3-10 membered heteroalicyclic group), —$C_{1-4}$ alkyl-($C_{6-12}$ bicyclic alicyclic group), —$C_{1-4}$ alkyl-(6-12 membered bicyclic heteroalicyclic group), —$C_{1-4}$ alkyl-($C_{8-15}$ tricyclic alicyclic group), —$C_{1-4}$ alkyl-(8-15 membered tricyclic heteroalicyclic group), —$C_{1-4}$ alkyl-($C_{5-8}$ aryl), —$C_{1-4}$ alkyl-(5-10 membered heteroaryl), —$N(R^{10})(R^{11})$, —$N(R^{10})(C(=O)R^{11})$, —$N(R^{10})(C(=O)—OR^{11})$, —$N(R^{12})(C(=O)—N(R^{10})(R^{11}))$, —C(=O)—$N(R^{10})(R^{11})$, —C(=O)—$R^{12}$, —C(=O)—$OR^{12}$, —OC(=O)$R^{12}$, —$N(R^{10})(S(=O)_2R^{11})$, —$S(=O)_2$—$N(R^{10})(R^{11})$, —$SR^{12}$, and —$OR^{12}$, wherein the —S—$C_{1-4}$ alkyl, $C_{1-6}$ alkyl, $C_{1-6}$ alkoxy, $C_{1-6}$ haloalkoxy, $C_{2-8}$ alkenyl, $C_{2-8}$ alkynyl, $C_{3-7}$ alicyclic group, 3-10 membered heteroalicyclic group, $C_{6-12}$ bicyclic alicyclic group, 6-12 membered bicyclic heteroalicyclic group, $C_{8-15}$ tricyclic alicyclic group, 8-15 membered tricyclic heteroalicyclic group, $C_{5-8}$ aryl, 5-7 membered heteroaryl, $C_{7-11}$ bicycloaryl, 7-11 membered bicyclic heteroaryl, —$C_{1-4}$ alkyl-($C_{3-7}$ alicyclic group), —$C_{1-4}$ alkyl-(3-10 membered heteroalicyclic group), —$C_{1-4}$ alkyl-($C_{6-12}$ bicyclic alicyclic group), —$C_{1-4}$ alkyl-(6-12 membered bicyclic heteroalicyclic group), —$C_{1-4}$ alkyl-($C_{8-15}$ tricyclic alicyclic group), —$C_{1-4}$ alkyl-(8-15 membered tricyclic heteroalicyclic group), —$C_{1-4}$ alkyl-($C_{5-8}$ aryl), and —$C_{1-4}$ alkyl-(5-10 membered heteroaryl) are each optionally substituted with 0, 1, 2, 3 or 4 $R^{5a}$; and $R^{5a}$ is independently selected from halogen, —OH, —$NO_2$, —CN, —$SF_5$, —SH, —S—$C_{1-4}$ alkyl, oxo, $C_{1-4}$ alkyl, $C_{1-4}$ haloalkyl, $C_{1-4}$ alkoxy, $C_{1-4}$ haloalkoxy, $C_{2-8}$ alkenyl, $C_{2-8}$ alkynyl, $C_{3-7}$ alicyclic group, 3-10 membered heteroalicyclic group, $C_{5-8}$ aryl, 5-7 membered heteroaryl, —$N(R^{13})(R^{14})$, —$N(R^{13})(C(=O)R^{14})$, —$N(R^{13})(C(=O)—OR^{14})$, —$N(R^{15})(C(=O)—N(R^{13})(R^{14}))$ —C(=O)—$N(R^{13})(R^{14})$, —C(=O)—$R^{15}$, —C(=O)—$OR^{15}$, —OC(=O)$R^{15}$, —$N(R^{13})(S(=O)_2R^{14})$, —$S(=O)_2$—$N(R^{13})(R^{14})$, —$SR^{15}$, and —$OR^{15}$; and $R^{10}$, $R^1$, $R^{12}$, $R^{13}$, $R^{14}$ and $R^{15}$, at each occurrence, are each independently selected from H, $C_{1-6}$ alkyl, $C_{1-6}$ haloalkyl, $C_{3-7}$ alicyclic group, 3-10 membered heteroalicyclic group, $C_{5-8}$ aryl, 5-7 membered heteroaryl, $C_{7-11}$ bicycloaryl, 7-11 membered bicyclic heteroaryl, —$C_{1-4}$ alkyl-($C_{3-7}$ alicyclic group), —$C_{1-4}$ alkyl-(3-10 membered heteroalicyclic group), —$C_{1-4}$ alkyl-($C_{6-12}$ bicyclic alicyclic group), —$C_{1-4}$ alkyl-(6-12 membered bicyclic heteroalicyclic group), —$C_{1-4}$ alkyl-($C_{8-15}$ tricyclic alicyclic group), —$C_{1-4}$ alkyl-(8-15 membered tricyclic heteroalicyclic group), —$C_{1-4}$ alkyl-($C_{5-8}$ aryl), and —$C_{1-4}$ alkyl-(5-10 membered heteroaryl), wherein each substituent listed in the group is optionally substituted with 0, 1, 2, 3, or 4 substituents each independently selected from a group consisting of: halogen, —OH, —$NH_2$, —$NH(CH_3)$, —$N(CH_3)_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ alicyclic group, 3-10 membered heteroalicyclic group, $C_{5-8}$ aryl, 5-7 membered heteroaryl, $C_{7-11}$ bicycloaryl, 7-11 membered bicyclic heteroaryl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—$N(C_{1-4}\ alkyl)_2$, $C_{1-4}$ haloalkyl, $C_{1-4}$ alkoxy and $C_{1-4}$ haloalkoxy;

or $R^{10}$, $R^{11}$, and the atom(s) attached thereto together form a 3-14-membered ring;

or $R^{13}$, $R^{14}$, and the atom(s) attached thereto together form a 3-14-membered ring.

2. The compound or, or an optical isomer thereof, a geometric isomer thereof, a tautomer thereof or a mixture of various isomers, or a pharmaceutically acceptable salt thereof, or according to claim 1, wherein n is 1 or 2.

3. The compound, or an optical isomer thereof, a geometric isomer thereof, a tautomer thereof or a mixture of various isomers, or a pharmaceutically acceptable salt thereof, according to claim 1, wherein the compound of formula (I) has the following structure:

(II)

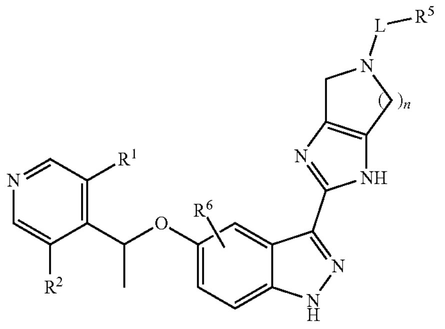

in which $R^1$, $R^2$, $R^5$, $R^6$, L and n are the same as what are defined in claim 1.

4. The compound, or an optical isomer thereof, a geometric isomer thereof, a tautomer thereof or a mixture of various isomers, or a pharmaceutically acceptable salt thereof, according to claim 1, wherein $R^1$ and $R^2$ are each independently selected from H, F, $C_1$ and Br.

5. The compound, or an optical isomer thereof, a geometric isomer thereof, a tautomer thereof or a mixture of various isometers, or a pharmaceutically accepable salt thereof, according to claim 1, wherein the compound of formula (I) has the following structure of formula (III) or formula (IV):

(III)

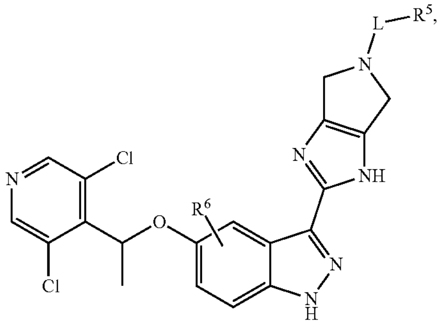

(IV)

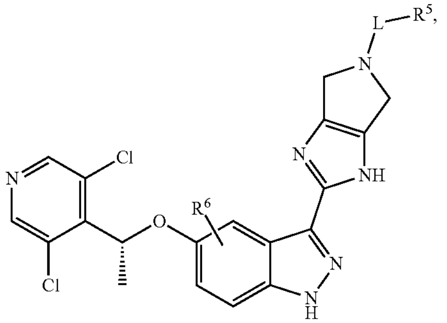

in which L, $R^5$ and $R^6$ are the same as what are defined in claim 1.

6. The compound, or an optical isomer thereof, a geometric isomer thereof, a tautomer thereof or a mixture of various isometers, or a pharmaceutically acceptable salt thereof, according to claim 1, wherein $R^6$ is H.

7. The compound, or an optical isomer thereof, a geometric isomer thereof, a tautomer thereof or a mixture of various isometers, or a pharmaceutically acceptable salt thereof, according to claim 1, wherein $R^5$ is selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{3-6}$ alicyclic group, 4-6 membered heteroalicyclic group, $C_{5-8}$ aryl, 5-10 membered heteroaryl, —$C_{1-4}$ alkyl-($C_{3-7}$ alicyclic group), —$C_{1-4}$ alkyl-(3-10 membered heteroalicyclic group), —$C_{1-4}$ alkyl-($C_{5-8}$ aryl), —$C_{1-4}$ alkyl-(5-10 membered heteroaryl), —N($R^{10}$)($R^{11}$), wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{3-6}$ alicyclic group, 4-6 membered heteroalicyclic group, $C_{5-8}$ aryl, 5-10 membered heteroaryl, —$C_{1-4}$ alkyl-($C_{3-7}$ alicyclic group), —$C_{1-4}$ alkyl-(3-10 membered heteroalicyclic group), —$C_{1-4}$ alkyl-($C_{5-8}$ aryl), and —$C_{1-4}$ alkyl-(5-10 membered heteroaryl) are each optionally substituted with 0, 1, 2, 3 or 4 $R^{5a}$; and $R^{5a}$ is independently selected from halogen, —OH, —$NO_2$, —CN, oxo, $C_{1-4}$ alkyl, $C_{1-4}$ haloalkyl, $C_{1-4}$ alkoxy, $C_{1-4}$ haloalkoxy, $C_{3-7}$ alicyclic group, 3-10 membered heteroalicyclic group, $C_{5-8}$ aryl, 5-7 membered heteroaryl; and $R^{10}$, $R^{11}$ and $R^{12}$, $R^{13}$, $R^{14}$ and $R^{15}$, at each occurrence, are each independently selected from H, $C_{1-6}$ alkyl, $C_{1-6}$ haloalkyl, $C_{3-7}$ alicyclic group, 3-10 membered heteroalicyclic group wherein each substituent listed in the group is optionally substituted with 0, 1, 2, 3, or 4 substituents each independently selected from a group consisting of: halogen, —OH, —$NH_2$, oxo, $C_{1-4}$ alkyl, $C_{1-4}$ hydroxyalkyl, $C_{1-4}$ haloalkyl, $C_{1-4}$ alkoxy and $C_{1-4}$ haloalkoxy; or $R^{10}$, $R^{11}$, and the atom(s) attached thereto together form a 3-8-membered ring.

8. The compound, or an optical isomer thereof, a geometric isomer thereof, a tautomer thereof or a mixture of various isometers, or a pharmaceutically acceptable salt thereof, according to claim 1, wherein $R^5$ is selected from H, halogen, —OH, methyl, ethyl, propyl, butyl, pentyl, hexyl, methoxy, ethoxy, propoxy, butoxy, pentyloxy, hexyloxy, cyclopropyl, cyclobutyl, cyclopentyl, cyclohexyl, cycloheptyl, phenyl, piperazinyl, piperidinyl, morpholinyl, pyrrolidinyl, pyrrolyl, morpholinyl, pyridinyl, and pyrazolyl, wherein the methyl, ethyl, propyl, butyl, pentyl, hexyl, methoxy, ethoxy, propoxy, butoxy, pentyloxy, hexyloxy, cyclopropyl, cyclobutyl, cyclopentyl, cyclohexyl, cycloheptyl, phenyl, piperazinyl, piperidinyl, morpholinyl, pyrrolidinyl, pyrrolyl, morpholinyl, pyridinyl, and pyrazolyl are each optionally substituted with 1 or 2 $R^{5a}$, and $R^{5a}$ is independently selected from halogen, —OH, —$NO_2$, —CN, oxo, $C_{1-4}$ alkyl, $C_{1-4}$ haloalkyl, and $C_{1-4}$ alkoxy.

9. A compound selected from:

(2-(5-(1-(3,5-dichloropyridin-4-yl)ethoxy)-1H-indazol-3-yl)-4,6-dihydropyrrolo[3,4-d]imidazol-5(1H)-yl)(4-methylpiperazin-1-yl)ketone;

5-(1-(3,5-dichloropyridin-4-yl)ethoxy)-3-(5-((1-methylpiperidin-4-yl)methyl)-1,4,5,6-tetrahydropyrrolo[3,4-d]imidazol-2-yl)-1H-indazole;

5-(1-(3,5-dichloropyridin-4-yl)ethoxy)-3-(5-(1-methylpiperidin-4-yl)-1,4,5,6-tetrahydropyrrolo[3,4-d]imidazol-2-yl)-1H-indazole;

2-(5-(1-(3,5-dichloropyridin-4-yl)ethoxy)-1H-indazol-3-yl)-5-(1-methylpiperidin-4-yl)-4,5,6,7-tetrahydro-3H-imidazo[4,5-c]pyridine;

(2-(5-(1-(3,5-dichloropyridin-4-yl)ethoxy)-1H-indazol-3-yl)-3,4,6,7-tetrahydro-5H-imidazo[4,5-c]pyridin-5-yl)(4-methylpiperazin-1-yl)ketone;

(2-(5-(1-(3,5-dichloropyridin-4-yl)ethoxy)-1H-indazol-3-yl)-4,6-dihydropyrrolo[3,4-d]imidazol-5(1H)-yl)(1-methylpiperidin-4-yl)ketone;

5-(1-(3,5-dichloropyridin-4-yl)ethoxy)-3-(5-(pyridin-3-ylsulfonyl)-1,4,5,6-tetrahydropyrrolo[3,4-d]imidazol-2-yl)-1H-indazole;

(2-(5-(1-(3,5-dichloropyridin-4-yl)ethoxy)-1H-indazol-3-yl)-4,6-dihydropyrrolo[3,4-d]imidazol-5(1H)-yl)(morpholinyl)ketone;

(2-(5-(1-(3,5-dichloropyridin-4-yl)ethoxy)-1H-indazol-3-yl)-4,6-dihydropyrrolo[3,4-d]imidazol-5(1H)-yl)((R)-pyrrolidin-3-yl)ketone;

(2-(5-(1-(3,5-dichloropyridin-4-yl)ethoxy)-1H-indazol-3-yl)-4,6-dihydropyrrolo[3,4-d]imidazol-5(1H)-yl)((S)-3-hydroxypyrrolidin-1-yl)ketone;

5-(1-(3,5-dichloropyridin-4-yl)ethoxy)-3-(5-methyl-1,4,5,6-tetrahydropyrrolo[3,4-d]imidazol-2-yl)-1H-indazole;

4-(2-(2-(5-(1-(3,5-dichloropyridin-4-yl)ethoxy)-1H-indazol-3-yl)-4,6-dihydropyrrolo[3,4-d]imidazol-5(1H)-yl)ethyl)morpholine;

1-(2-(5-(1-(3,5-dichloropyridin-4-yl)ethoxy)-1H-indazol-3-yl)-4,6-dihydropyrrolo[3,4-d]imidazol-5(1H)-yl)-2-morpholinoethan-1-one;

1-(2-(5-(1-(3,5-dichloropyridin-4-yl)ethoxy)-1H-indazol-3-yl)-4,6-dihydropyrrolo[3,4-d]imidazol-5(1H)-yl)-2-(dimethylamino)ethan-1-one;

2-(2-(5-(1-(3,5-dichloropyridin-4-yl)ethoxy)-1H-indazol-3-yl)-4,6-dihydropyrrolo[3,4-d]imidazol-5(1H)-yl)ethan-1-ol;

5-(1-(3,5-dichloropyridin-4-yl)ethoxy)-3-(5-(methylsulfonyl)-1,4,5,6-tetrahydropyrrolo[3,4-d]imidazol-2-yl)-1H-indazole;

(R)-5-(1-(3,5-dichloropyridin-4-yl)ethoxy)-3-(5-(methylsulfonyl)-1,4,5,6-tetrahydropyrrolo[3,4-d]imidazol-2-yl)-1H-indazole;

Methyl 2-(5-(1-(3,5-dichloropyridin-4-yl)ethoxy)-1H-indazol-3-yl)-4,6-dihydropyrrolo [3,4-d]imidazole-5(1H)-carboxylate;

Methyl (R)-2-(5-(1-(3,5-dichloropyridin-4-yl)ethoxy)-1H-indazol-3-yl)-4,6-dihydropyrrolo [3,4-d]imidazole-5(1H)-carboxylate;

5-(1-(3,5-dichloropyridin-4-yl)ethoxy)-3-(5-((1-methyl-1H-pyrazol-4-yl)sulfonyl)-1,4,5,6-tetrahydropyrrolo[3,4-d]imidazol-2-yl)-1H-indazole;

5-(1-(3,5-dichloropyridin-4-yl)ethoxy)-3-(1,4,5,6-tetrahydropyrrolo[3,4-d]imidazol-2-yl)-1H-indazole;

5-(1-(3,5-dichloropyridin-4-yl)ethoxy)-3-(5-((1-methyl-1H-pyrazol-3-yl)sulfonyl)-1,4,5,6-tetrahydropyrrolo[3,4-d]imidazol-2-yl)-1H-indazole;

3-(2-(5-(1-(3,5-dichloropyridin-4-yl)ethoxy)-1H-indazol-3-yl)-4, 6-dihydropyrrolo[3,4-d]imidazol-5(1H)-yl)cyclobutan-1-ol;

4-(2-(5-(1-(3,5-dichloropyridin-4-yl)ethoxy)-1H-indazol-3-yl)-4, 6-dihydropyrrolo[3,4-d]imidazol-5(1H)-yl)cyclohexan-1-ol;

Ethyl 2-(5-(1-(3,5-dichloropyridin-4-yl)ethoxy)-1H-indazol-3-yl)-4,6-dihydropyrrolo [3,4-d]imidazole-5(1H)-carboxylate;

2-Cyanoethyl 2-(5-(1-(3,5-dichloropyridin-4-yl)ethoxy)-1H-indazol-3-yl)-4,6-dihydropyrrolo[3,4-d]imidazole-5(1H)-carboxylate;

Cyclopropyl (2-(5-(1-(3,5-dichloropyridin-4-yl)ethoxy)-1H-indazol-3-yl)-4,6-dihydropyrrolo[3,4-d]imidazol-5(1H)-yl)ketone;

(2-(5-(1-(3, 5-dichloropyridin-4-yl)ethoxy)-1H-indazol-3-yl)-4,6-dihydropyrrolo[3,4-d]imidazol-5(1H)-yl)(3-hydroxycyclobutyl)ketone;

3-(2-(5-(5-(1-(3,5-dichloropyridin-4-yl)ethoxy)-1H-indazol-3-yl)-4,6-dihydropyrrolo [3,4-d]imidazol-5(1H)-yl)-3-oxopropane-carbonitrile;

5-(1-(3,5-dichloropyridin-4-yl)ethoxy)-3-(5-(ethylsulfonyl)-1,4,5,6-tetrahydropyrrolo[3,4-d]imidazol-2-yl)-1H-indazole;

3-(5-(cyclopropylsulfonyl)-1,4,5,6-tetrahydropyrrolo[3,4-d]imidazol-2-yl)-5-(1-(3,5-dichloropyridin-4-yl) ethoxy)-1H-indazole;

5-(1-(3,5-dichloropyridin-4-yl)ethoxy)-3-(5-(isopropylsulfonyl)-1,4,5,6-tetrahydropyrrolo[3,4-d]imidazol-2-yl)-1H-indazole;

1-(2-(5-(1-(3,5-dichloropyridin-4-yl)ethoxy)-1H-indazol-3-yl)-4,6-dihydropyrrolo[3,4-d]imidazol-5(1H)-yl)-2-(3-hydroxypyrrolidin-1-yl)ethan-1-one;

1-(2-(2-(5-(1-(3,5-dichloropyridin-4-yl)ethoxy)-1H-indazol-3-yl)-4,6-dihydropyrrolo [3,4-d]imidazol-5(1H)-yl)-2-oxoethyl)pyrrolidine-3-carbonitrile;

(R)-2-(5-(1-(3,5-dichloropyridin-4-yl)ethoxy)-1H-indazol-3-yl)-N-methyl-4,6-dihydropyrrolo[3,4-d]imidazole-5(1H)-carboxamide;

(R)-2-(5-(1-(3,5-dichloropyridin-4-yl)ethoxy)-1H-indazol-3-yl)-N,N-dimethyl-4,6-dihydropyrrolo[3,4-d]imidazole-5(1H)-carboxamide;

(R)-2-(5-(1-(3,5-dichloropyridin-4-yl)ethoxy)-1H-indazol-3-yl)-N-(1-methyl-1H-pyrazol-4-yl)-4,6-dihydropyrrolo[3,4-d]imidazole-5(1H)-carboxamide;

5-((R)-1-(3,5-dichloropyridin-4-yl)ethoxy)-3-(5-(1-methylpyrrolidin-3-yl)-1,4,5,6-tetrahydropyrrolo[3, 4-d] imidazol-2-yl)-1H-indazole;

5-((R)-1-(3,5-dichloropyridin-4-yl)ethoxy)-3-(5-(1-(1-methylpiperidin-4-yl)ethyl)-1,4,5,6-tetrahydropyrrolo [3,4-d]imidazol-2-yl)-1H-indazole;

5-((R)-1-(3,5-dichloropyridin-4-yl)ethoxy)-3-(5-(1-methylpiperidin-3-yl)-1,4,5,6-tetrahydropyrrolo[3,4-d]imidazol-2-yl)-1H-indazole;

5-((R)-1-(3,5-dichloropyridin-4-yl)ethoxy)-3-(5-(1-(methylsulfonyl)pyrrolidin-3-yl)-1,4,5,6-tetrahydropyrrolo[3,4-d]imidazol-2-yl)-1H-indazole;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(pyrrolidin-1-yl)ethan-1-one;

1-(2-(5-((R)-1-(3,5-dichloropyridin-4-yl)ethoxy)-1H-indazol-3-yl)-4,6-dihydropyrrolo[3,4-d]imidazol-5(1H)-yl)-2-((R)-3-hydroxypyrrolidin-1-yl)ethan-1-one;

1-(2-(5-((R)-1-(3,5-dichloropyridin-4-yl)ethoxy)-1H-indazol-3-yl)-4,6-dihydropyrrolo[3,4-d]imidazol-5(1H)-yl)-2-((S)-3-hydroxypyrrolidin-1-yl)ethan-1-one;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(dimethylamino)ethan-1-one;

3-(5-(L-prolyl)-1,4,5,6-tetrahydropyrrolo[3,4-d]imidazol-2-yl)-5-((R)-1-(3,5-dichloropyridin-4-yl)ethoxy)-1H-indazole;

5-((R)-1-(3,5-dichloropyridin-4-yl)ethoxy)-3-(5-(methyl-L-prolyl)-1,4,5,6-tetrahydropyrrolo[3,4-d]imidazol-2-yl)-1H indazole;

(2-(5-((R)-1-(3,5-dichloropyridin-4-yl)ethoxy)-1H-indazol-3-yl)-4,6-dihydropyrrolo[3,4-d]imidazol-5(1H)-yl)((S)-piperidin-2-yl)ketone;

(2-(5-((R)-1-(3,5-dichloropyridin-4-yl)ethoxy)-1H-indazol-3-yl)-4,6-dihydropyrrolo[3,4-d]imidazol-5(1H)-yl)((S)-1-methylpiperidin-2-yl)ketone;

1-(2-(5-((R)-1-(3,5-dichloropyridin-4-yl)ethoxy)-1H-indazol-3-yl)-4,6-dihydropyrrolo[3,4-d]imidazol-5(1H)-yl)-2-(3-fluoropyrrolidin-1-yl)ethan-1-one;

1-(2-(2-(5-((R)-1-(3,5-dichloropyridin-4-yl)ethoxy)-1H-indazol-3-yl)-4,6-dihydropyrrolo[3,4-d]imidazol-5(1H)-yl)-2-oxyethyl)pyrrolidine-3-carbonitrile;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(piperidin-1-yl)ethan-1-one;

(R)-2-(azetidin-1-yl)-1-(2-(5-(1-(3,5-dichloropyridin-4-yl)ethoxy)-1H-indazol-3-yl)-4,6-dihydropyrrolo[3,4-d] imidazol-5(1H)-yl)ethan-1-one;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(3-hydroxyazetidin-1-yl)ethan-1-one;

(R)-1-(2-(5-(1-(3,5-dichloropyridin-4-yl)ethoxy)-1H-indazol-3-yl)-4,6-dihydropyrrolo[3,4-d]imidazol-5(1H)-yl)-2-(3-fluoroazetidin-1-yl)ethan-1-one;

2-(dimethylamino)ethyl (R)-2-(5-(1-(3,5-dichloropyridin-4-yl)ethoxy)-1H-indazol-3-yl)-4,6-dihydropyrrolo [3,4-d]imidazole-5(1H)-carboxylate;

1-methylpyrrolidin-3-yl 2-(5-((R)-1-(3,5-dichloropyridin-4-yl)ethoxy)-1H-indazol-3-yl)-4,6-dihydropyrrolo [3,4-d]imidazole-5(1H)-carboxylate;

or an optical isomer thereof, a geometric isomer thereof, a tautomer thereof or a mixture of various isomers, or a pharmaceutically acceptable salt thereof.

10. A pharmaceutical composition comprising the compound according to claim 1, or an optical isomer thereof, a geometric isomer thereof, a tautomer thereof or a mixture of various isomers, or a pharmaceutically acceptable salt thereof, and one or more pharmaceutically acceptable carriers, adjuvants, or excipients.

11. A method of treating diseases or conditions associated with FGFR, said method comprising administering to a patient in need thereof a therapeutically effective amount of the compound according to claim 1, or an optical isomer thereof, a geometric isomer thereof, a tautomer thereof or a mixture of various isomers, or a pharmaceutically acceptable salt thereof.

12. The method according to claim 11, wherein the diseases or conditions associated with FGFR are selected from cancers, skeletal disorders or chondrocyte disorders, hypophosphatemia disorders and fibrotic diseases.

13. The method according to claim 12, wherein the diseases or conditions associated with FGFR are selected from hepatocellular carcinoma, breast cancer, bladder cancer, colorectal cancer, melanoma, mesothelioma, lung cancer, prostate cancer, membrane adenocarcinoma, testicular cancer, thyroid cancer, squamous cell carcinoma, glioblastoma, neuroblastoma, uterine cancer, and rhabdomyosarcoma.

14. The method according to claim 11, wherein the diseases or conditions associated with FGFR are diseases and conditions that are resistant to FGFR inhibitors that do not target gatekeeper mutants of FGFR due to gatekeeper mutations in FGFR.

15. A method of treating diseases or conditions associated with FGFR, said method comprising administering to a patient in need thereof a therapeutically effective amount of the pharmaceutical composition according to claim 10.

16. The method according to claim 15, wherein the diseases or conditions associated with FGFR are selected from cancers, skeletal disorders or chondrocyte disorders, hypophosphatemia disorders and fibrotic diseases.

17. The method according to claim 16, wherein the diseases or conditions associated with FGFR are selected from hepatocellular carcinoma, breast cancer, bladder cancer, colorectal cancer, melanoma, mesothelioma, lung cancer, prostate cancer, membrane adenocarcinoma, testicular cancer, thyroid cancer, squamous cell carcinoma, glioblastoma, neuroblastoma, uterine cancer, and rhabdomyosarcoma.

18. The method according to claim 15, wherein the diseases or conditions associated with FGFR are diseases and conditions that are resistant to FGFR inhibitors that do not target gatekeeper mutants of FGFR due to gatekeeper mutations in FGFR.

* * * * *